United States Patent
Kambe et al.

(10) Patent No.: US 9,978,975 B2
(45) Date of Patent: May 22, 2018

(54) ORGANIC ELECTROLUMINESCENCE DEVICE

(71) Applicant: Sony Corporation, Minato-ku, Tokyo (JP)

(72) Inventors: Emiko Kambe, Tokyo (JP); Masato Nakamura, Tokyo (JP); Masakazu Funahashi, Sodegaura (JP); Hiroshi Yamamoto, Sodegaura (JP); Sayaka Mizutani, Sodegaura (JP)

(73) Assignee: JOLED INC, Tokyo (JP)

( * ) Notice: Subject to any disclaimer, the term of this patent is extended or adjusted under 35 U.S.C. 154(b) by 721 days.

(21) Appl. No.: 14/387,824

(22) PCT Filed: Mar. 22, 2013

(86) PCT No.: PCT/JP2013/001947
§ 371 (c)(1),
(2) Date: Sep. 24, 2014

(87) PCT Pub. No.: WO2013/145667
PCT Pub. Date: Oct. 3, 2013

(65) Prior Publication Data
US 2015/0069351 A1 Mar. 12, 2015

(30) Foreign Application Priority Data
Mar. 29, 2012 (JP) .................. 2012-076217

(51) Int. Cl.
| | |
|---|---|
| *C07D 487/14* | (2006.01) |
| *C07C 255/35* | (2006.01) |
| *C07D 471/04* | (2006.01) |
| *C07C 255/37* | (2006.01) |
| *C09K 11/06* | (2006.01) |
| *H01L 51/50* | (2006.01) |
| *H01L 51/52* | (2006.01) |
| *H01L 51/00* | (2006.01) |

(Continued)

(52) U.S. Cl.
CPC .......... *H01L 51/504* (2013.01); *C07C 255/34* (2013.01); *C07C 255/35* (2013.01); *C07C 255/37* (2013.01); *C07C 255/41* (2013.01); *C07C 255/50* (2013.01); *C07C 255/61* (2013.01); *C07C 261/04* (2013.01); *C07D 471/04* (2013.01); *C07D 487/14* (2013.01); *H01L 51/0072* (2013.01); *H01L 51/5068* (2013.01); *H01L 51/5076* (2013.01); *H01L 51/5092* (2013.01); *H01L 51/5234* (2013.01); *C07C 2103/40* (2013.01); *C07C 2103/52* (2013.01); *C07C 2103/54* (2013.01); *C09K 11/06* (2013.01); *C09K 2211/1011* (2013.01); *H01L 51/0051* (2013.01); *H01L 51/0052* (2013.01)

(58) Field of Classification Search
None
See application file for complete search history.

(56) References Cited

U.S. PATENT DOCUMENTS

| | | | |
|---|---|---|---|
| 6,137,223 A | 10/2000 | Hung et al. | |
| 2005/0098207 A1 | 5/2005 | Matsumoto et al. | |

(Continued)

FOREIGN PATENT DOCUMENTS

| | | |
|---|---|---|
| EP | 2371812 A1 | 10/2011 |
| JP | 2000-058265 A | 2/2000 |

(Continued)

OTHER PUBLICATIONS

European Search Report for EP Application No. 13767954.4 dated Jun. 19, 2017, 7 pages.

(Continued)

*Primary Examiner* — Samantha L Shterengarts
(74) *Attorney, Agent, or Firm* — Sheridan Ross P.C.

(57) ABSTRACT

An organic electroluminescence device including: an anode; one or more organic thin film layers including an emitting layer; a donor-containing layer; an acceptor-containing layer; and a light-transmissive cathode in this order, wherein the donor-containing layer comprises a compound represented by the following formula (I) or (II):

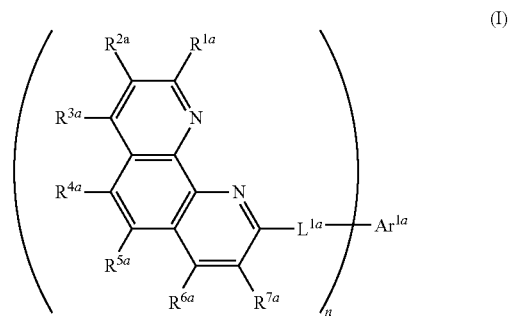

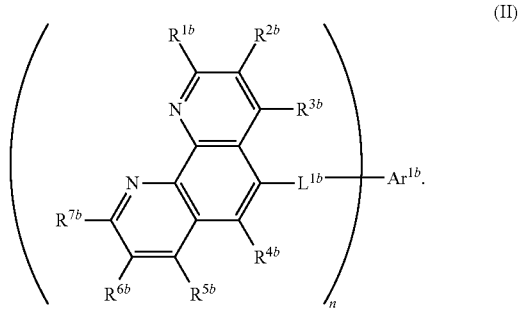

14 Claims, 1 Drawing Sheet

(51) Int. Cl.
*C07C 255/50* (2006.01)
*C07C 255/61* (2006.01)
*C07C 261/04* (2006.01)
*C07C 255/34* (2006.01)
*C07C 255/41* (2006.01)

(56) References Cited

U.S. PATENT DOCUMENTS

2009/0128024 A1 5/2009 Fukuoka et al.
2010/0108990 A1 5/2010 Hosokawa et al.
2011/0284827 A1 11/2011 Morishita et al.
2012/0012820 A1 1/2012 Endo et al.
2012/0280214 A1 11/2012 Makino et al.

FOREIGN PATENT DOCUMENTS

| | | |
|---|---|---|
| JP | 2005-166637 A | 6/2005 |
| JP | 2012-022953 A | 2/2012 |
| JP | 2012-049088 A | 3/2012 |
| WO | WO-2007/018004 A1 | 2/2007 |
| WO | WO-2007/123061 A1 | 11/2007 |
| WO | WO-2007/130047 A1 | 11/2007 |
| WO | WO-2010/073348 A1 | 7/2010 |

OTHER PUBLICATIONS

International Search Report issued in PCT/JP2013/001947 dated Jun. 25, 2013.
International Preliminary Report on Patentability and Written Opinion of the International Searching Authority issued in Application No. PCT/2013/001947, dated Oct. 9, 2014.

ORGANIC ELECTROLUMINESCENCE DEVICE

CROSS REFERENCE TO RELATED APPLICATIONS

The present application is a National Stage of International Application No. PCT/JP2013/001947 filed on Mar. 22, 2013, which claims the benefit of Japanese Appln. No. 2012-076217 filed Mar. 29, 2012, the entire disclosures of which are incorporated herein by reference.

TECHNICAL FIELD

The invention relates to an organic electroluminescence device in which a light-transmissive electrode is used as a cathode.

BACKGROUND ART

An organic electroluminescence (EL) device is a self-emission device utilizing the principle that light is emitted by the recombination energy of holes injected from an anode and electrons injected from a cathode. In order to outcouple the light generated by recombination to the outside of the device, in general, a conductive film having light transmittance is used in one or both of an anode and a cathode.

As such a conductive film, an indium-tin-oxide film (Indium-Tin-Oxide: ITO) is preferably used. Since ITO has a work function of about 5 eV, it is preferable to be used as an anode. On the other hand, ITO is not suited to be used as a cathode, since difference in affinity level with surrounding layers such as an electron-transporting layer is large.

Therefore, in an organic EL device in which light is outcoupled from a cathode, it has been proposed that formation of an electron-injecting layer formed of a mixture of a metal having a small work function such as cesium (Cs) and an electron-transporting organic material between an organic emitting layer and an electrode formed of a transparent conductive film. Due to such a configuration, electron-injection properties of a cathode are enhanced.

Many of transparent conductive films represented by ITO are made of a metal oxide, and formed by a sputtering method using argon (Ar) or oxygen ($O_2$) as a process gas. At this time, the electron-injecting layer containing the above-mentioned metal having a small work function is decomposed and oxidized, resulting in lowering in electron-injection properties. As a result, problems arise that the driving voltage of a device is increased, current leakage occurs, device life is shortened, or the like.

In order to solve the problem, an organic EL device using copper phthalocyanine as the underlayer of the transparent conductive film has been disclosed (see Patent Document 1).

An organic EL device in which a stacked body of a layer obtained by contacting an organic metal complex compound containing at least one of ions of small-work-function metals having a work function of 4.0 eV or less and a heat-reductive metal such as aluminum (Al) and a layer formed of molybdenum oxide, porphyrin or the like is formed in an electron-transporting part and a transparent conductive film is formed thereon (see Patent Document 2, FIG. 19).

Further, an organic EL device is disclosed in which a donor-containing layer, an acceptor-containing layer and a cathode are provided in this sequence and the donor-containing layer contains at least one selected from a donor metal, a donor metal compound and a donor metal complex (see Patent Document 3).

However, when comparing with a device using a cathode of a metal having a small work function formed by deposition, this device has a problem that the efficiency of a device is deteriorated and the life of a device is shortened.

RELATED ART DOCUMENTS

Patent Documents

Patent Document 1: JP-A-2000-58265
Patent Document 2: JP-A-2005-166637
Patent Document 3: WO2007/123061

SUMMARY OF THE INVENTION

An object of the invention is to provide an organic EL device that enables light to be outcoupled from a cathode and has a high luminous efficiency and can be driven at a lower voltage.

According to one embodiment of the invention, the following organic EL device is provided.

1. An organic electroluminescence device comprising:
   an anode;
   one or more organic thin film layers including an emitting layer;
   a donor-containing layer;
   an acceptor-containing layer; and
   a light-transmissive cathode in this order,
   wherein the donor-containing layer comprises a compound represented by the following formula (I) or (II):

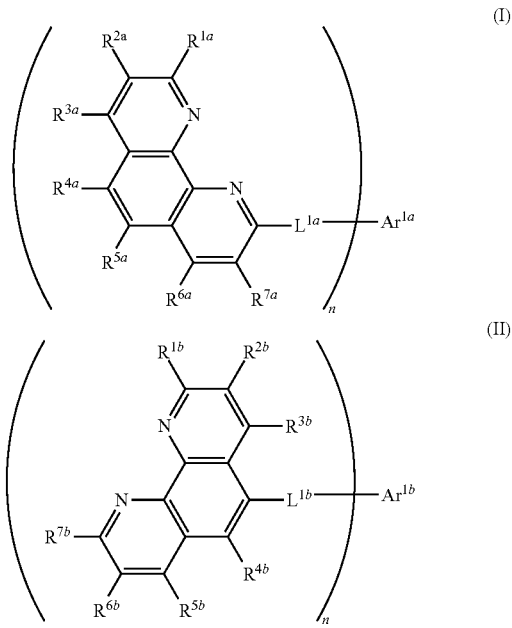

wherein in the formulas,
$R^{1a}$ to $R^{7a}$ and $R^{1b}$ to $R^{7b}$ are independently a hydrogen atom, a substituted or unsubstituted aryl group including 6 to 60 carbon atoms that form a ring (hereinafter referred to as "ring carbon atoms"), a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 ring carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group that is substituted with a substituted or unsubstituted aryl group including 6 to 50 ring carbon atoms, a halogen atom, a cyano group, a nitro group, a hydroxyl group or a carboxyl group, and adjacent groups of $R^{1a}$ to $R^{7a}$ or adjacent groups of $R^{1b}$ to $R^{7b}$ may be bonded each other to form a ring;

$L^{1a}$ and $L^{1b}$ are independently a single bond or a linkage group;

$Ar^{1a}$ and $Ar^{1b}$ are independently a substituted or unsubstituted aromatic group including 6 to 60 carbon atoms; and n is an integer of 1 to 4, and when n is 2 or more, the groups having a phenanthroline skeleton in parentheses may be the same or different from each other.

According to the invention, it is possible to provide an organic EL device that enables light to be outcoupled from a cathode and has a high luminous efficiency and can be driven at a lower voltage.

MODE FOR CARRYING OUT THE INVENTION

The organic EL device according to one aspect of the invention comprises an anode, one or more organic thin film layers including an emitting layer, a donor-containing layer, an acceptor-containing layer and a light-transmissive electrode in this sequence.

Figure 1:
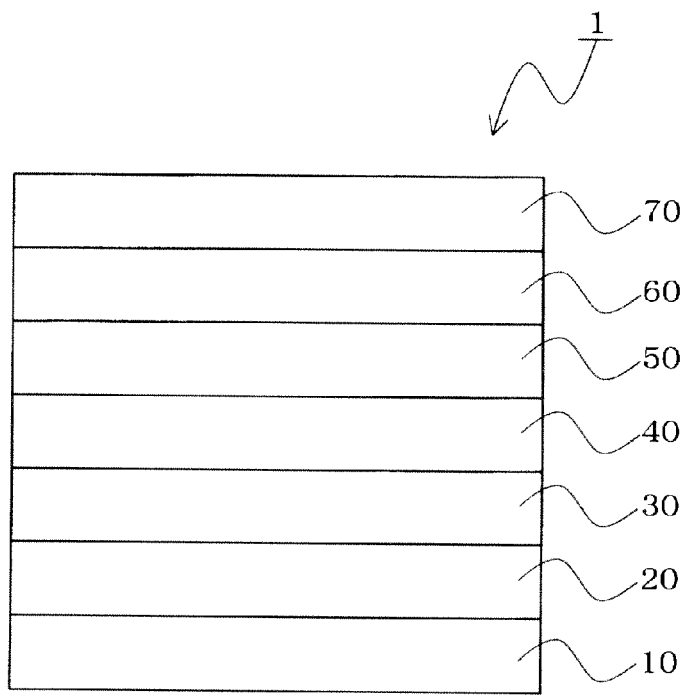
FIG. 1 is a view showing a layer configuration of one embodiment of the organic EL device according to one aspect of the invention.

FIG. 1 shows a device configuration of the organic EL device according to the invention.

An organic device 1 has a device configuration in which an anode 10, a hole-injecting layer 20, a hole-transporting layer 30, an emitting layer 40, a donor-containing layer 50, an acceptor-containing layer 60 and a light-transmissive cathode 70 are stacked in this sequence.

In the invention, the acceptor-containing layer 60 is a layer which draws electrons from the cathode 70 (accepts electrons) and transfers the electrons into the donor-containing layer 50. In conventional organic EL devices, for injecting electrons from a cathode into an organic substance, a material having a small work function is used as a cathode. In the invention, by providing the acceptor-containing layer 60, if a material having a large work function such as ITO is employed as a cathode, an increase in driving voltage can be suppressed.

The donor-containing layer 50 is a layer which draws electrons from the acceptor-containing layer 60 and injects the electrons into the emitting layer 40 (donates electrons). By providing the donor-containing layer 50, receiving electrons from the acceptor-containing layer 60 are facilitated, thereby to lower the driving voltage, and allow for high efficiency and prolonged life.

In this device 1, acceptors contained in the acceptor-containing layer 60 draw electrons from an interface with the cathode 70. Since the acceptor-containing layer 60 has electron-transporting properties, the electrons are trans-ported from this interface to the acceptor-containing layer 60 in the direction toward the donor-containing layer 50. Further, the electrons are injected from the donor-containing layer 50 in the direction toward the emitting layer 40. On the other hand, holes are injected from the anode 10 to the hole-injecting layer 20 and the hole-transporting layer 30, and further into the emitting layer 40. In the emitting layer 40, injected holes and injected electrons are recombined to emit light.

In an organic EL device according to one aspect of the invention, by providing a donor-containing layer 50, a large difference in affinity level between an emitting layer 40 and an acceptor-containing layer 60 can be eliminated.

If the donor-containing layer 50 is not present, since the difference in affinity level between the acceptor-containing layer 60 and the emitting layer 40 is large, a high voltage is required to be applied. For this reason, in this device configuration, even if an electrode is subjected to negative bias, the device cannot emit successfully.

In the invention, by providing an acceptor-containing layer 60 and a donor-containing layer 50 between a cathode 70 and an emitting layer 40, transporting electrons are facilitated, thereby to obtain an organic emitting device capable of being driven at a lower voltage and having a high efficiency and a prolonged life.

The invention is characterized in that the donor-containing layer comprises a compound represented by the following formula (I) or (II).

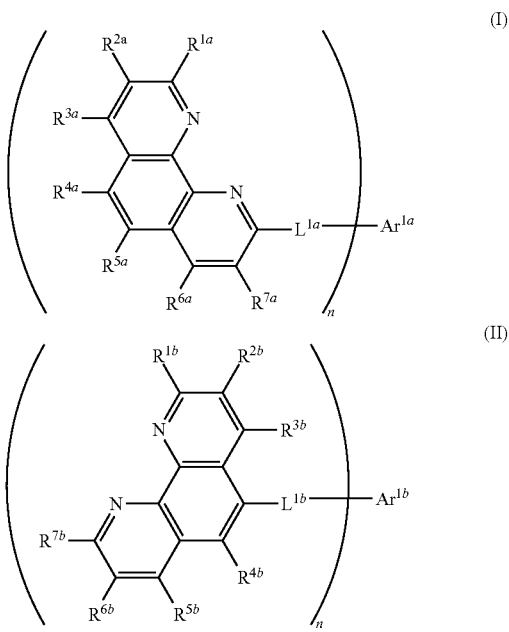

Although the compound represented by the formula (I) or (II) is an organic compound, they have resistant to damage caused by sputtering. Therefore, if a transparent electrode layer such as ITO is formed as a cathode, it is possible to suppress the deterioration of organic thin film layers including an emitting layer.

The compounds represented by the formulas (I) and (II) will be explained below.

In the above-mentioned formulas (I) and (II), $R^{1a}$ to $R^{7a}$ and $R^{1b}$ to $R^{7b}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 ring carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group substituted with a substituted or unsubstituted aryl group including 6 to 50 ring carbon atoms, a halogen atom, a cyano group, a nitro group, a hydroxyl group or a carboxyl group.

Adjacent groups of $R^{1a}$ to $R^{7a}$ or adjacent groups of $R^{1b}$ to $R^{7b}$ may be bonded each other to form a ring. Examples of the ring include a benzene ring, a naphthalene ring, a pyrazine ring, a pyridine ring, a furan ring or the like.

$L^{1a}$ and $L^{1b}$ are independently a single bond or a linkage group. As the linkage group, a substituted or unsubstituted aromatic group including 6 to 20 ring carbon atoms, a substituted or unsubstituted alkylene group including 1 to 8 carbon atoms and a substituted or unsubstituted heterocyclic ring can be given. Specifically, a substituted or unsubstituted benzene ring group, a substituted or unsubstituted naphthalene ring group, a substituted or unsubstituted methylene group or a substituted or unsubstituted pyridine ring group are preferable.

$Ar^{1a}$ and $Ar^{1b}$ are independently a substituted or unsubstituted aromatic group including 6 to 60 carbon atoms.

n is 1 to 4, and when n is 2 or more, the groups having a phenanthroline skeleton in parentheses may be the same or different.

As the compound represented by the formula (I) or (II), compounds represented by the following formula (I-a), (I-b), (II-a) or (II-b) are preferable

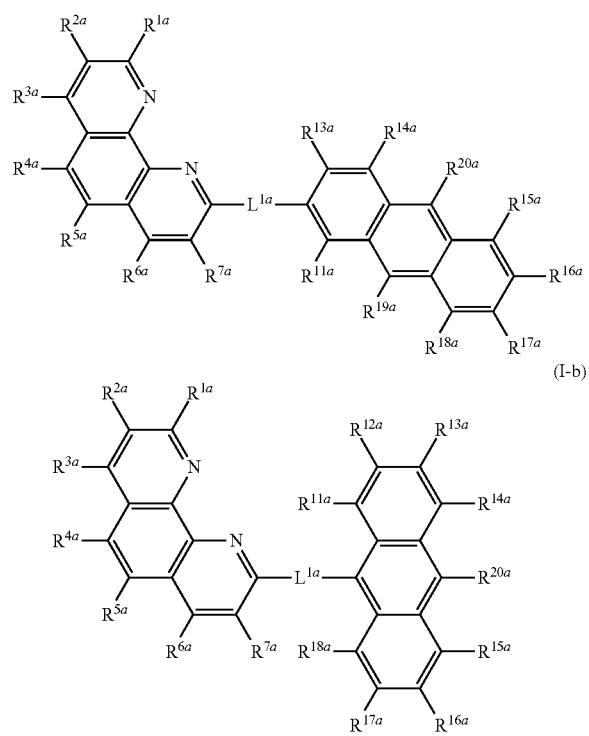

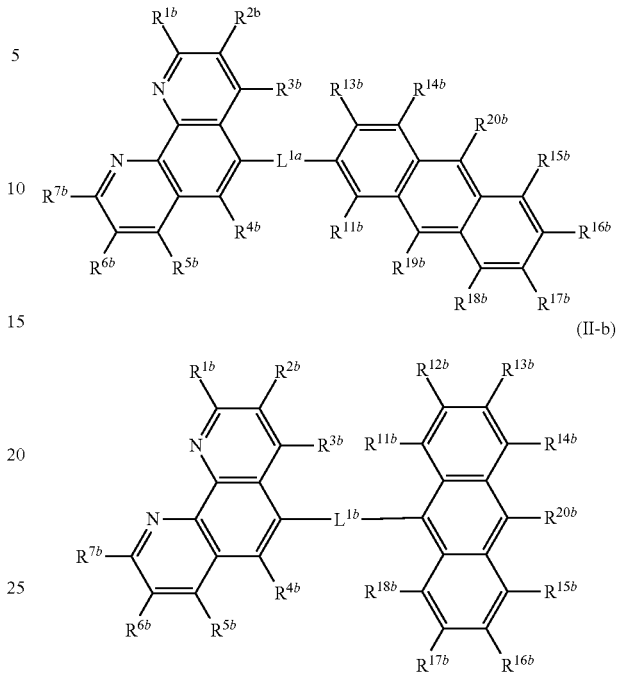

Due to the presence of a group having a phenanthroline skeleton and a group having an anthracene skeleton, it becomes possible to have both a function as an electron acceptor and a transporting function as an electron-transporting layer. Further, deposition stability or film forming property is improved.

In the formulas (I-a), (I-b), (II-a) and (II-b), $R^{1a}$ to $R^{7a}$, $R^{1b}$ to $R^{7b}$ and $L^{1a}$ and $L^{1b}$ are independently the same groups as $R^{1a}$ to $R^{7a}$, $R^{1b}$ to $R^{7b}$ and $L^{1a}$ and $L^{1b}$ in the formulas (I) and (II).

$R^{11a}$ to $R^{20a}$ and $R^{11b}$ to $R^{20b}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 ring carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 5 to 50 ring carbon atoms, a substituted or unsubstituted alkoxycarbonyl group including 2 to 50 carbon atoms, an amino group substituted with a substituted or unsubstituted aryl group including 6 to 50 ring carbon atoms, a halogen atom, a cyano group, a nitro group, a hydroxyl group or a carboxyl group.

Adjacent groups of $R^{11a}$ to $R^{20a}$ or adjacent groups of $R^{11b}$ or $R^{20b}$ may be bonded each other to form a ring. Examples of the ring include a benzene ring, a naphthalene ring, a pyrazine ring, a pyridine ring, a furan ring or the like.

Hereinbelow, an explanation will be made on examples of each group in the above-mentioned formula (I) or the like.

In this specification, the aryl group includes a monocyclic aromatic hydrocarbon ring group and a fused aromatic hydrocarbon ring group in which a plurality of hydrocarbon rings are fused. The heteroaryl group includes a monocyclic heteroaromatic ring group, a heterofused aromatic ring group in which a plurality of heteroaromatic rings are fused and a heterofused aromatic ring group in which an aromatic hydrocarbon ring and a heteroaromatic ring are fused.

The "unsubstituted" in the "substituted or unsubstituted . . ." means substitution by a hydrogen atom. The hydrogen atom in the compound according to one aspect of the invention includes isomers different in number of neutrons, i.e. protium, deuterium and tritium.

The ring carbon atoms (nucleus carbons) mean carbon atoms that constitute an aromatic ring. The ring atoms (nucleus atoms) mean carbon atoms and hetero atoms that constitute a heterocyclic ring (including a saturated ring, an unsaturated ring and an aromatic heterocyclic ring).

The aryl group including 6 to 60 ring carbon atoms is preferably an aryl group including 6 to 30, particularly preferably 6 to 20, carbon atoms. Examples thereof include phenyl, fluorenyl, naphthyl, anthryl, phenanthryl, chrysenyl, pyrenyl, triphenylenyl, fluoranthenyl or the like.

As the aromatic group indicated by $Ar^{1a}$ and $Ar^{1b}$, the aryl group mentioned above and a divalent or larger group obtained by removing a hydrogen atom from the aryl group can be given.

As $R^{1a}$ to $R^{7a}$ and $R^{1b}$ to $R^{7b}$ in the formulas (I) and (II), hydrogen, phenyl and naphthyl are preferable.

As the alkyl group including 1 to 50 carbon atoms, a linear or branched alkyl group can be given. The alkyl group is preferably one including 1 to 20, more preferably 1 to 12 and particularly preferably 1 to 8 carbon atoms. Examples include methyl, ethyl, propyl, butyl, pentyl and hexyl.

As the cycloalkyl group including 3 to 50 ring carbon atoms, cyclopentyl, cyclohexyl or the like can be given.

The aralkyl group including 7 to 50 ring carbon atoms is expressed as —Y—Z. As examples of Y, examples of alkylene corresponding to examples of the above-mentioned alkyl group can be given. As examples of Z, examples of the above-mentioned aryl group can be given. The aryl part of the aralkyl group preferably includes 6 to 30 carbon atoms. The alkyl part preferably includes 1 to 10 carbon atoms, with 1 to 6 being particularly preferable. The alkyl part is a benzyl group, a phenylethyl group or a 2-phenylpropane-2-yl group, for example.

The alkoxy group including 1 to 50 carbon atoms is expressed as —OY. As examples of Y, examples of the above-mentioned alkyl group can be given. The alkoxy group preferably includes 1 to 20, more preferably 1 to 12, and particularly preferably 1 to 8 carbon atoms. The alkoxy group is methoxy, ethoxy, propoxy, butoxy or the like, for example.

The aryloxy group including 6 to 50 ring carbon atoms is expressed as —OY. As examples of Y, examples of the above-mentioned aryl group can be given. The aryloxy group preferably includes 6 to 20, more preferably 6 to 16, and particularly preferably 6 to 12 carbon atoms. The aryloxy group is phenyloxy, 2-naphthyloxy or the like, for example.

The arylthio group including 6 to 50 ring carbon atoms is expressed as —SY. As examples of Y, examples of the above-mentioned aryl group can be given. The arylthio group preferably includes 6 to 20, more preferably 6 to 16, and particularly preferably 6 to 12 carbon atoms. The arylthio group is phenylthio or the like, for example.

The alkoxycarbonyl group including 2 to 50 carbon atoms preferably includes 2 to 20, more preferably 2 to 16, and particularly preferably 2 to 12 carbon atoms. The alkoxycarbonyl group is methoxycarbonyl, ethoxycarbonyl or the like, for example.

As the amino group substituted with the substituted or unsubstituted aryl group including 6 to 50 ring carbon atoms, diarylamino, alkylarylamino and arylamino can be given. As examples of the alkyl group and the aryl group that are bonded to the nitrogen atom, the aryl group and the alkyl group mentioned above can be given. The amino group is preferably includes 6 to 20, more preferably 6 to 12, and particularly preferably 6 carbon atoms. The amino group is diphenylamino or the like, for example.

As the halogen atom, a fluorine atom, a chlorine atom and a bromine atom can be given. A fluorine atom is preferable.

The substituents of each of the above-mentioned groups are independently a linear or branched alkyl group including 1 to 20 carbon atoms, a linear or branched alkenyl group including 2 to 20 carbon atoms, a cycloalkyl group including 3 to 20 ring carbon atoms, a trialkylsilyl group that respectively includes an alkyl group including 1 to 20 carbon atoms, a silyl group having an aryl group or alkyl group including 6 to 24 ring carbon atoms, an alkylarylsilyl group having an alkyl group including 1 to 20 carbon atoms and an aryl group including 6 to 24 ring carbon atoms, an aryl group including 6 to 24 ring carbon atoms, a heteroaryl group including 5 to 24 atoms that form a ring (hereinafter referred to as "ring atoms"), an alkoxy group including 1 to 20 carbon atoms, a halogen atom or a cyano group. Specifically, the aryl group, alkyl group, cycloalkyl group, heteroaryl group, alkoxy group, halogen atom or cyano group mentioned above can be given. Further, these groups may have similar substituents.

As the alkenyl group, a substituent having an unsaturated bond within a molecule of the above-mentioned alkyl group can be mentioned.

As the silyl group having an aryl group, a triarylsilyl group, an alkylarylsilyl group and a trialkylsilyl group can be given.

As examples of preferable substituents, methyl, ethyl, propyl, isopropyl, butyl, sec-butyl, tert-butyl, cyclohexyl, phenyl, 1-naphthyl, 2-naphthyl, trimethylsilyl and triphenylsilyl can be given.

The specific examples of the compound represented by the formulas (I) and (II) are shown below. The invention is not restricted to these compounds.

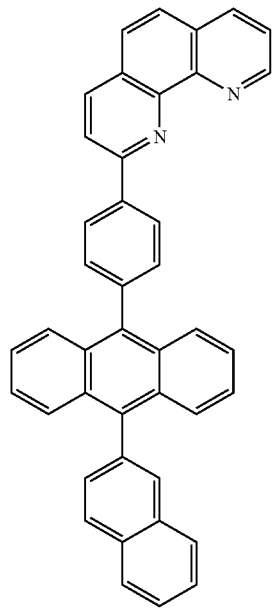 (B-1)
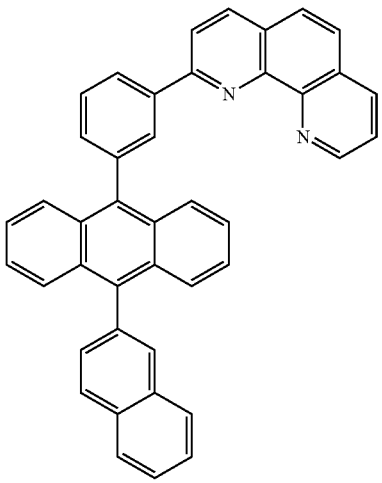 (B-2)
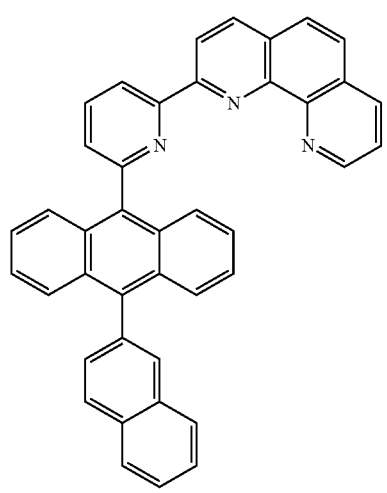 (B-3)
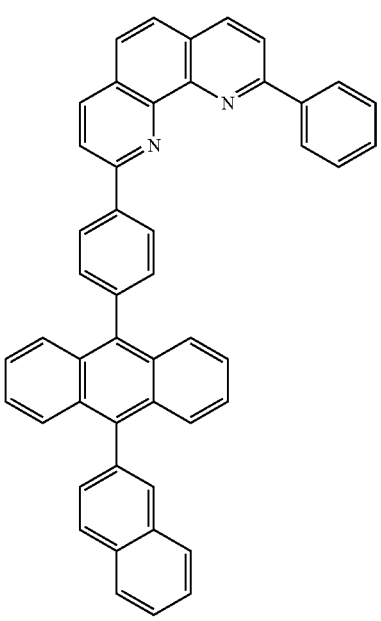 (B-4)

-continued
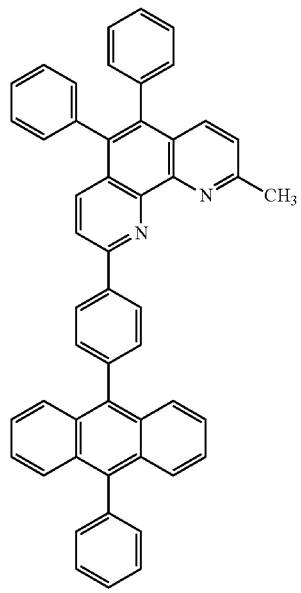
(B-5)
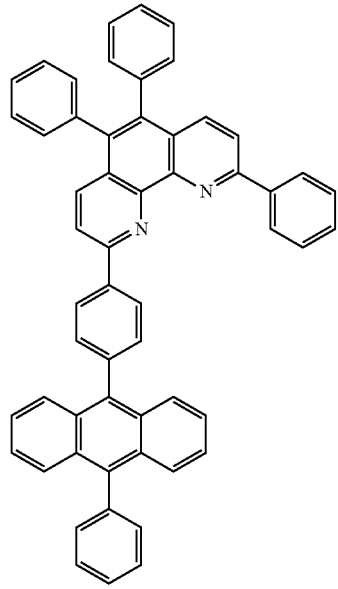
(B-6)
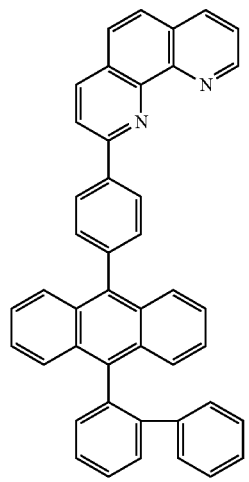
(B-7)
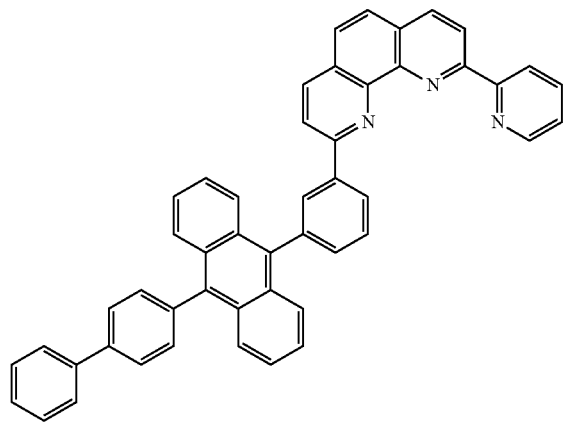
(B-8)
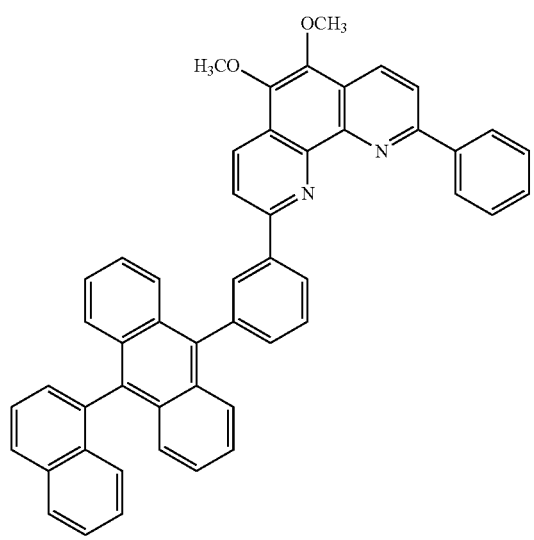
(B-9)
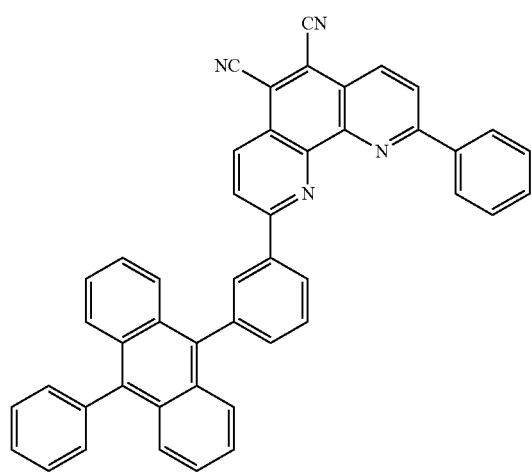
(B-10)

-continued
(B-11)
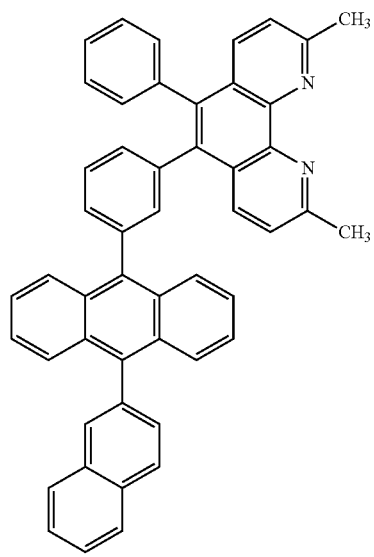
(B-12)
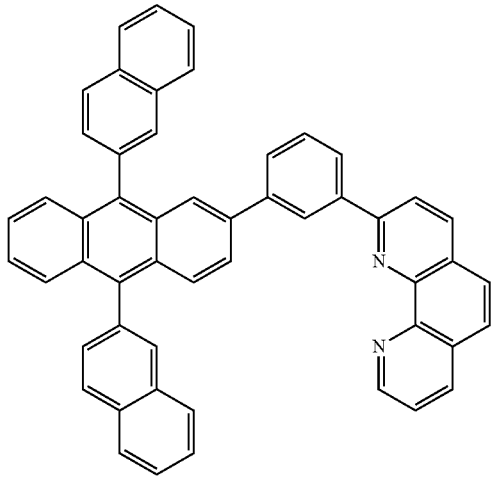
(B-13)
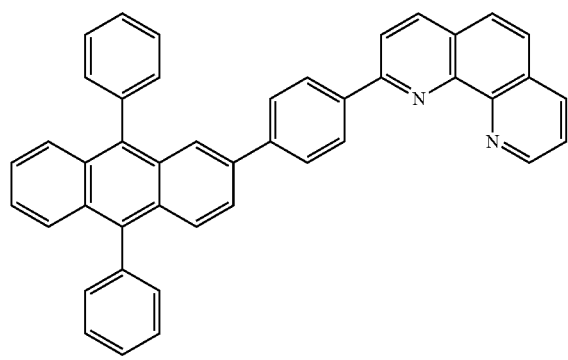
(B-14)
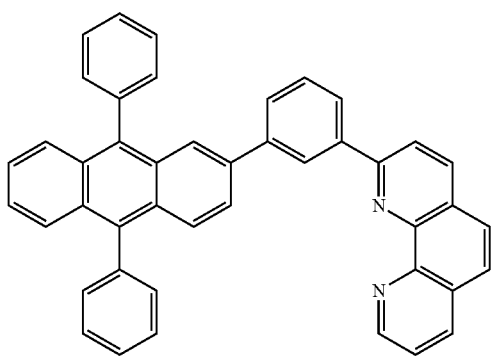
(B-15)
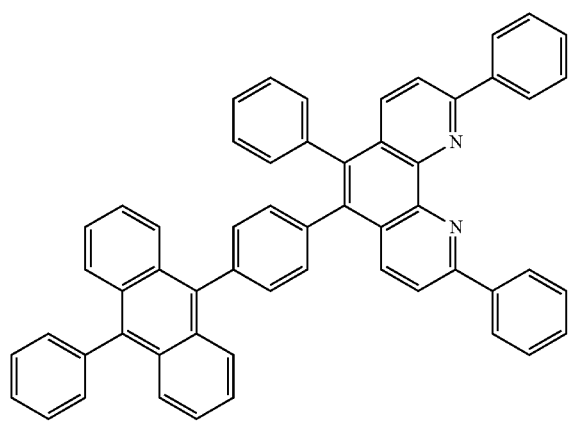
(B-16)
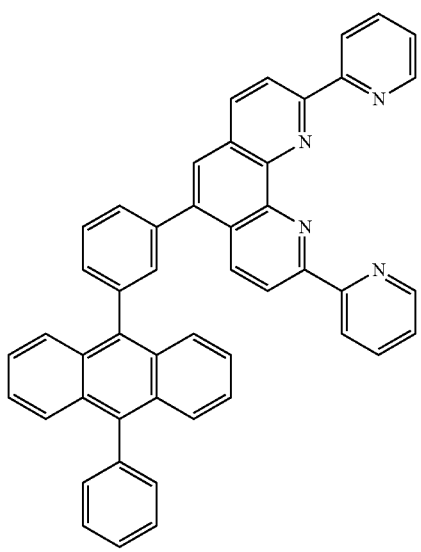

-continued
(B-17)
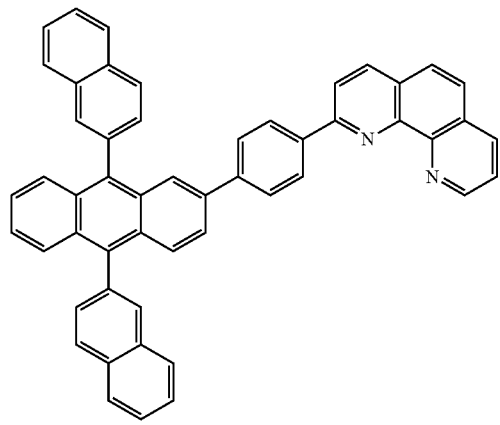
(B-18)
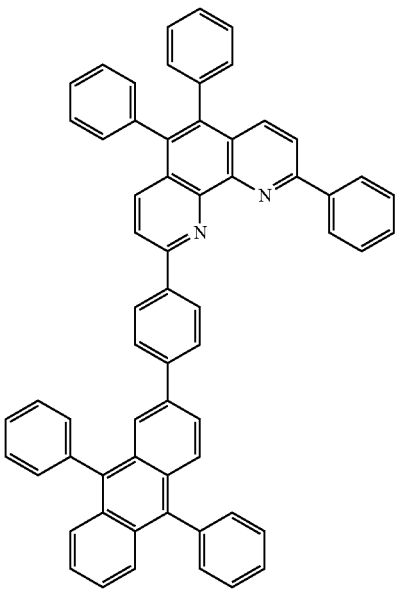
(B-19)
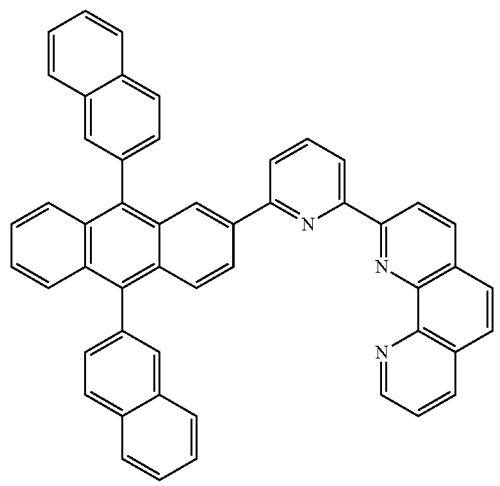
(B-20)
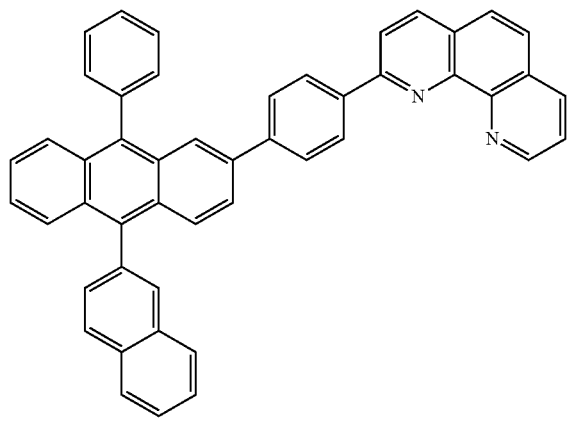
(B-21)
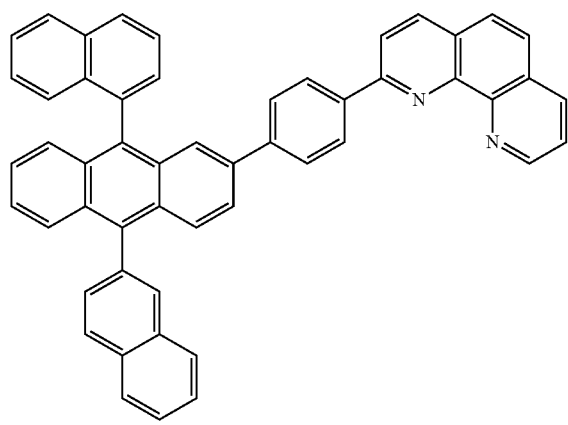
(B-22)
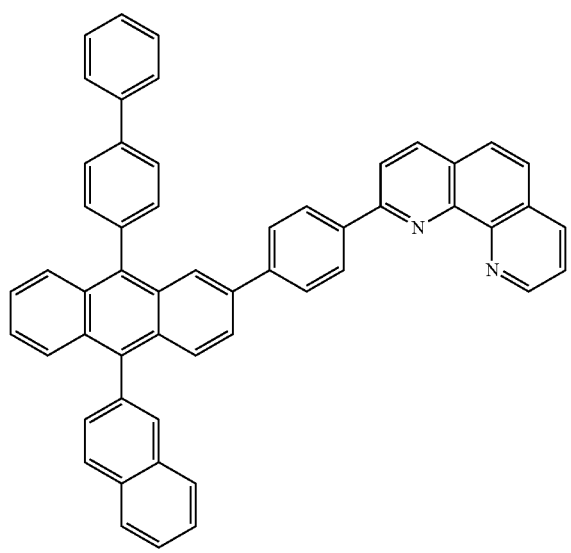

-continued
(B-23)
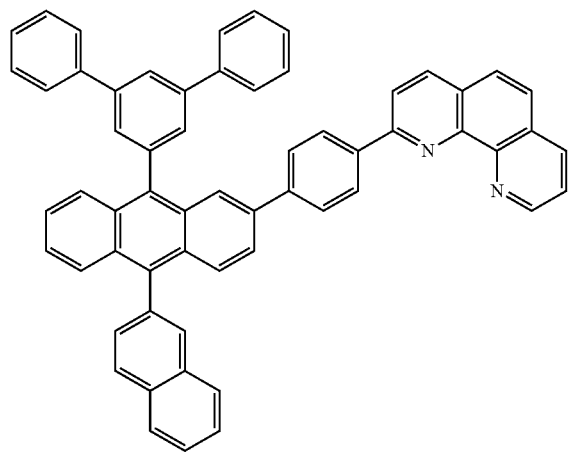
(B-24)
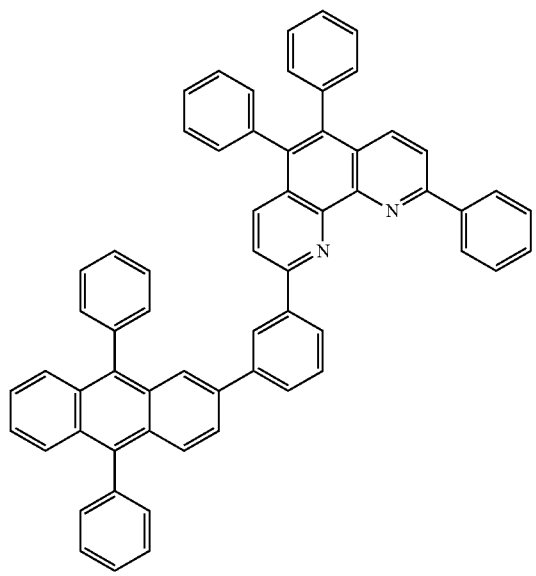
(B-25)
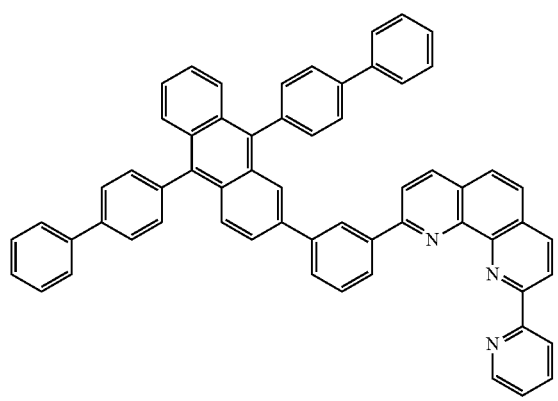
(B-26)
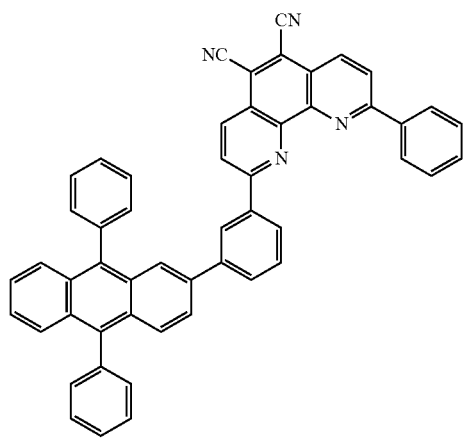
(B-27)
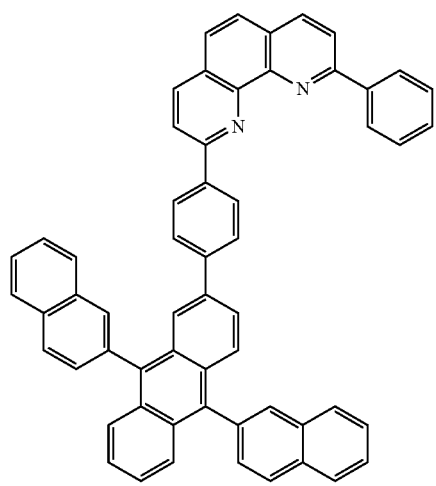
(B-28)
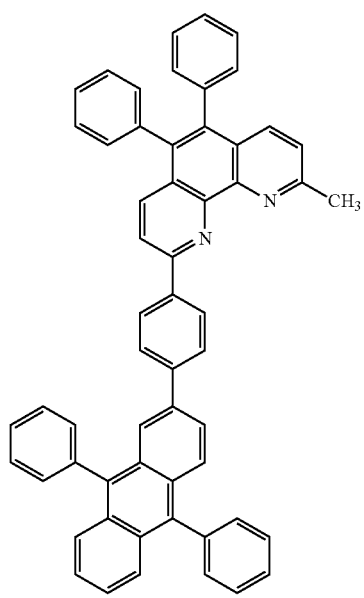

-continued
(B-29)
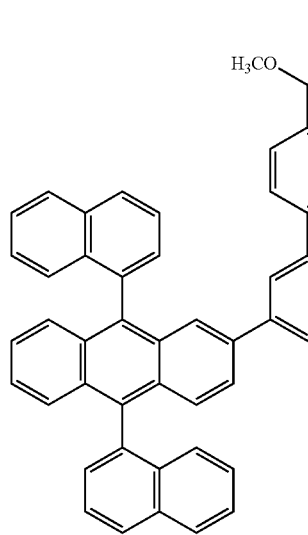
(B-30)
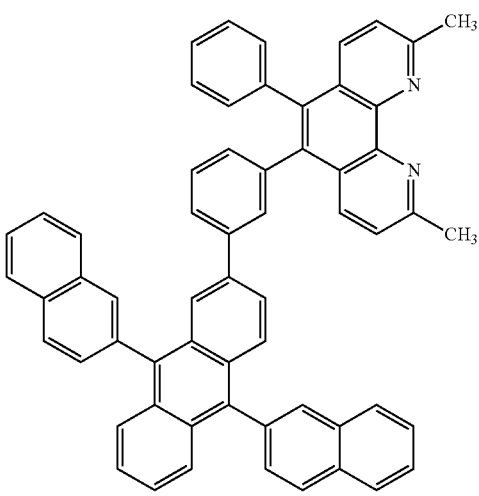
(B-31)
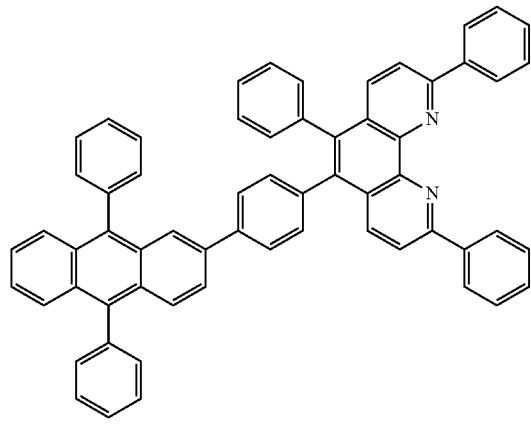
(B-32)
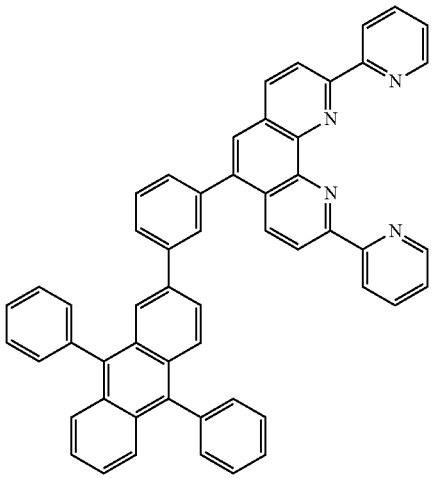
(B-33)
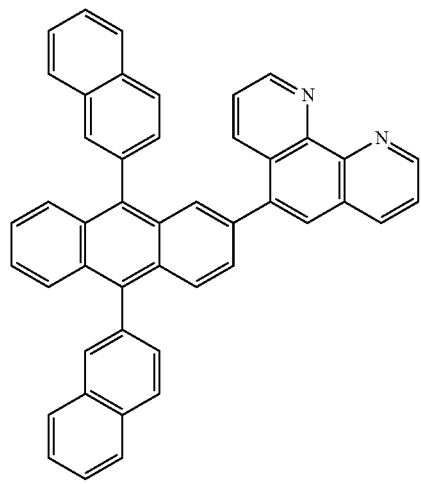
(B-34)
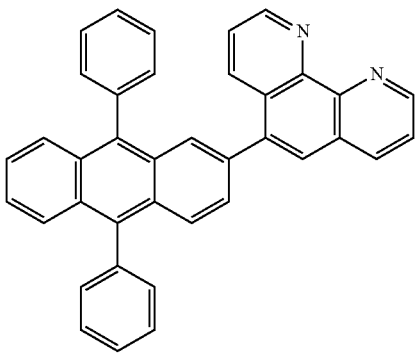

-continued
(B-35)
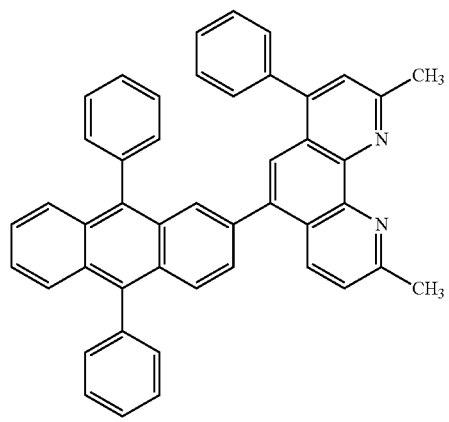
(B-36)
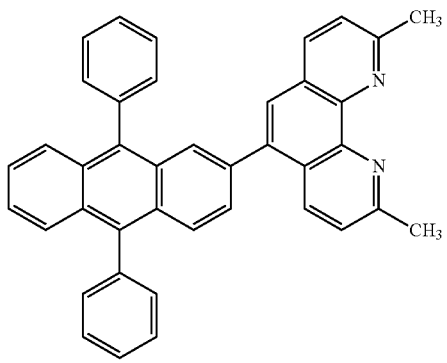
(B-37)
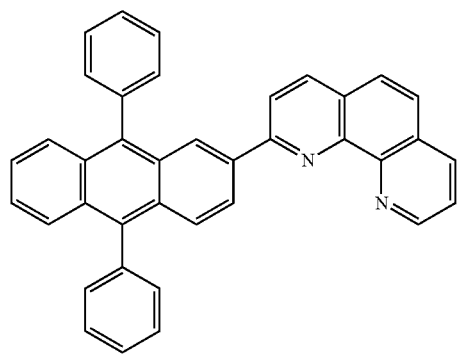
(B-38)
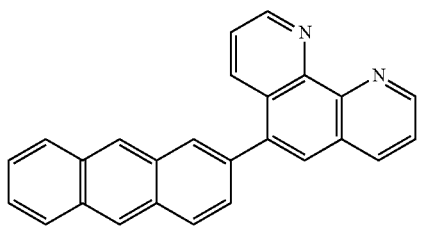
(B-39)
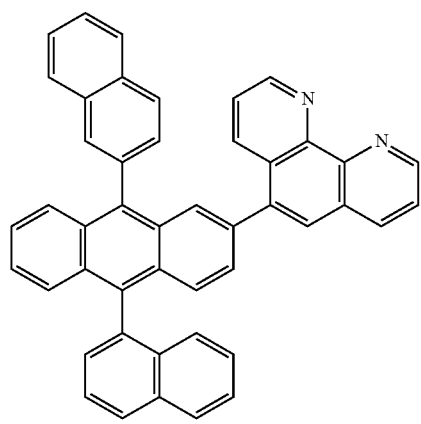
(B-40)
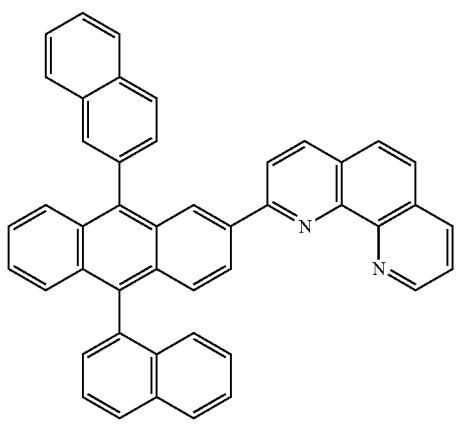
(B-41)
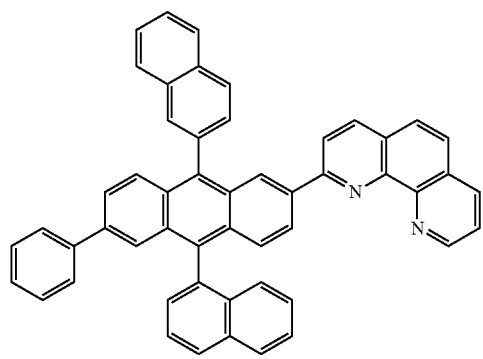
(B-42)
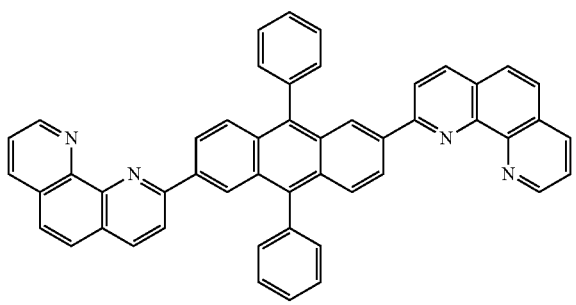

(B-43)
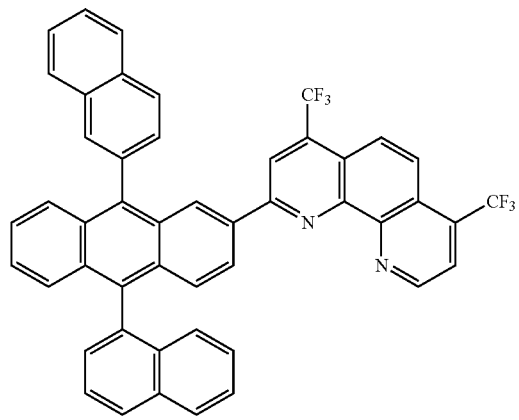
(B-44)
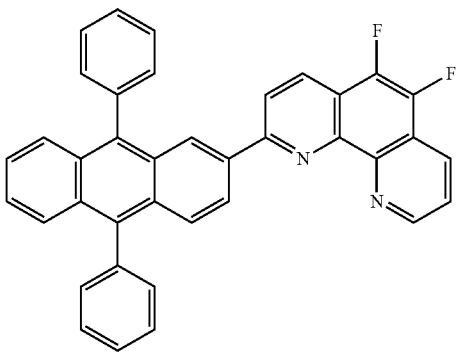
(B-45)
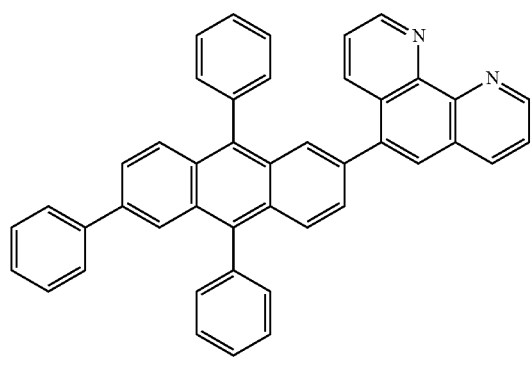
(B-46)
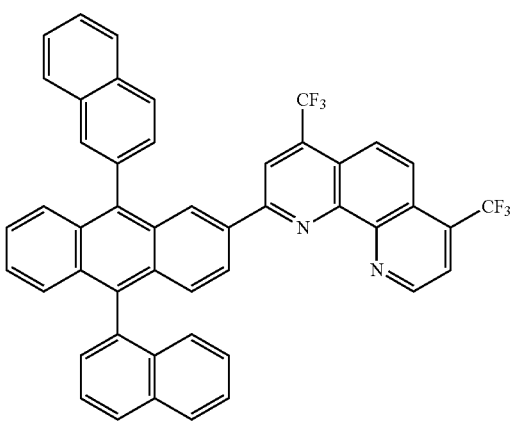
(B-47)
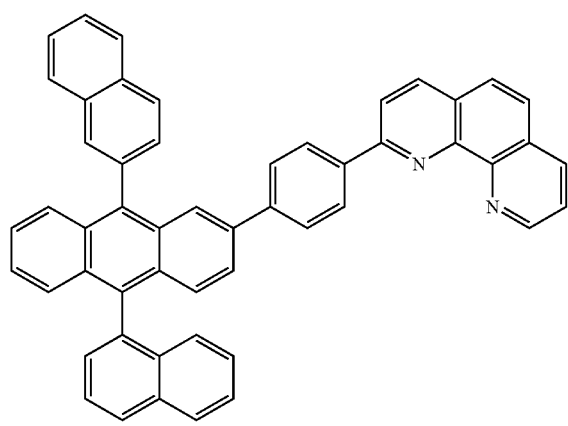
(B-48)
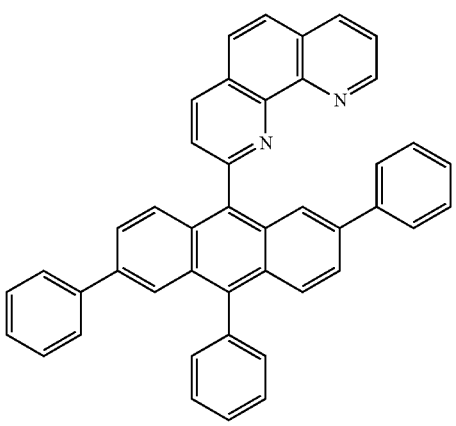

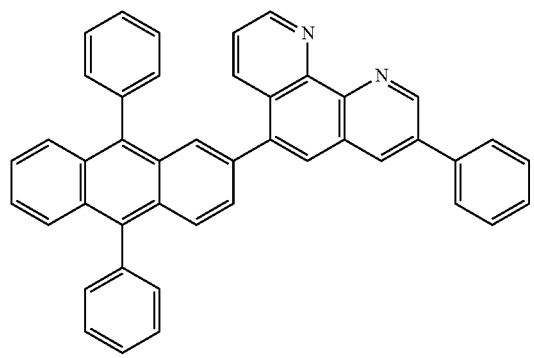
(B-49)
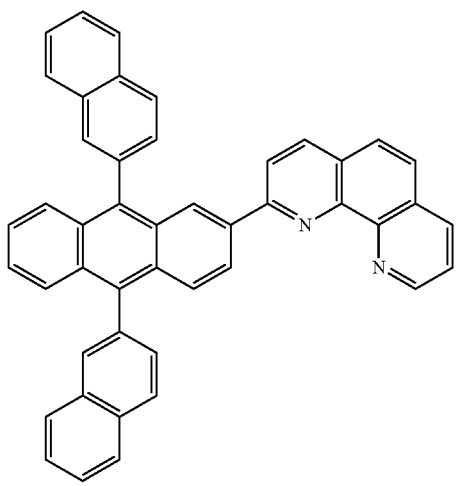
(B-50)
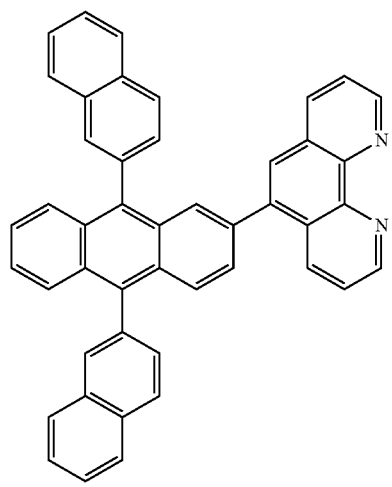
(B-51)
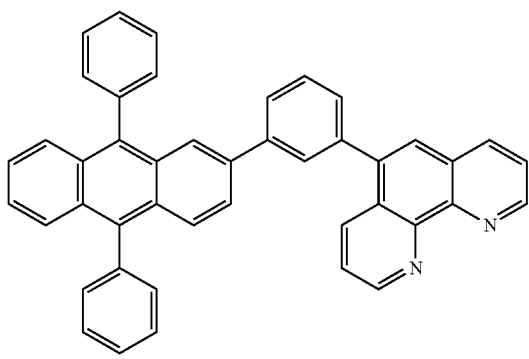
(B-52)
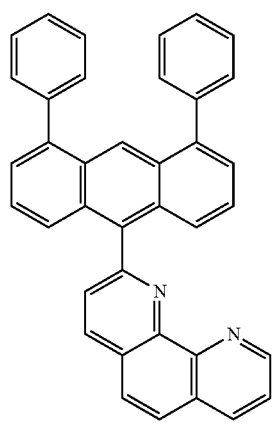
(B-53)
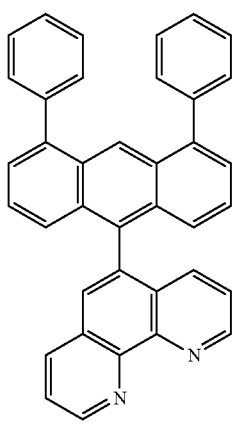
(B-54)

(B-55)
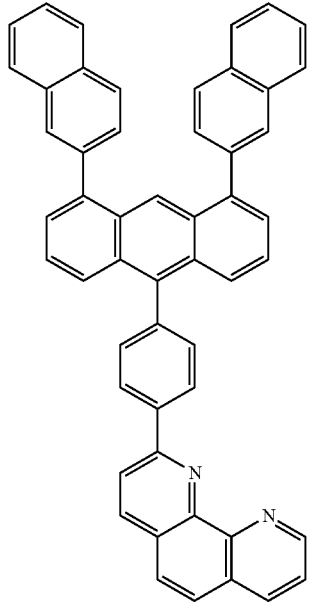
(B-56)
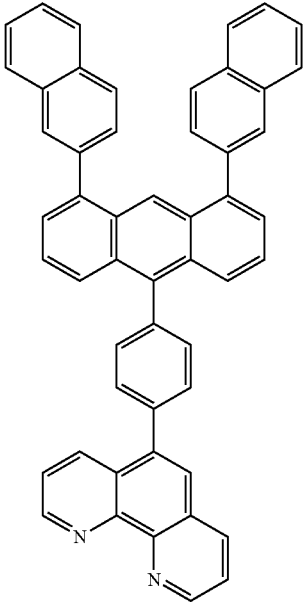
(B-57)
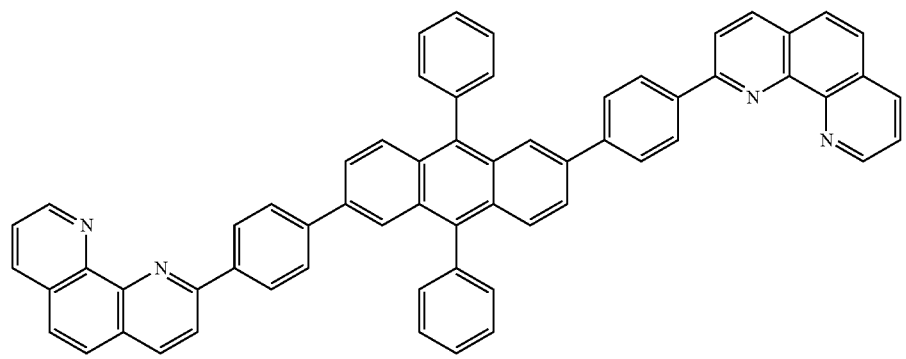
(B-58)
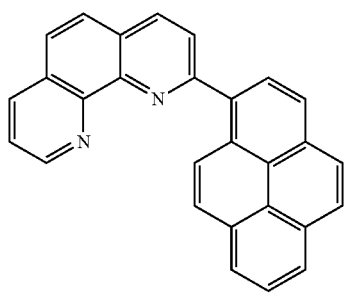
(B-59)
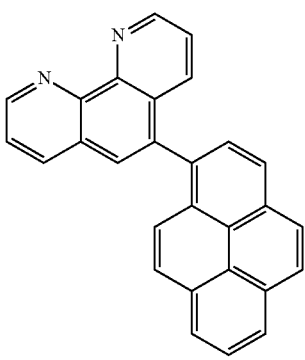

-continued
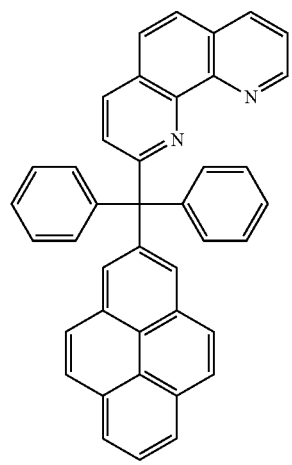
(B-60)
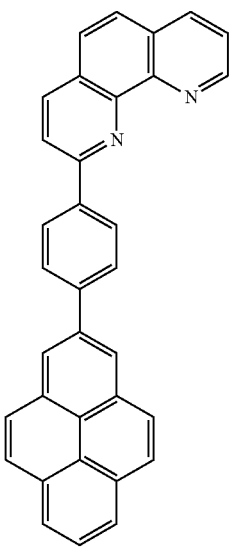
(B-61)
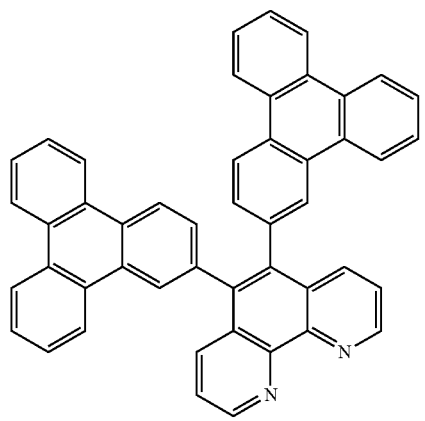
(B-62)
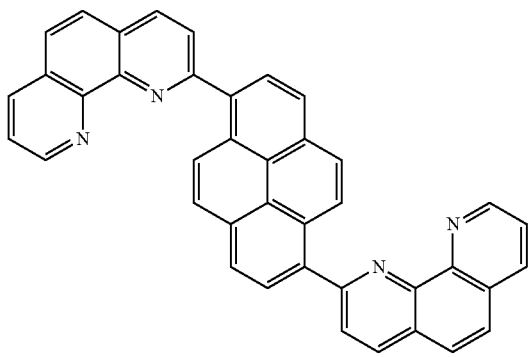
(B-63)
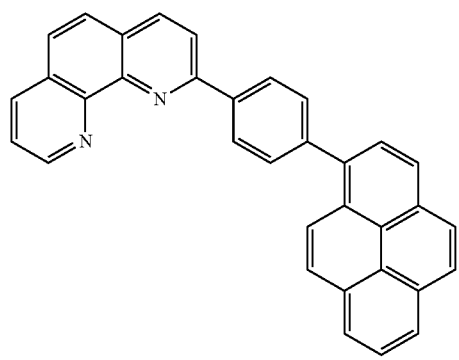
(B-64)
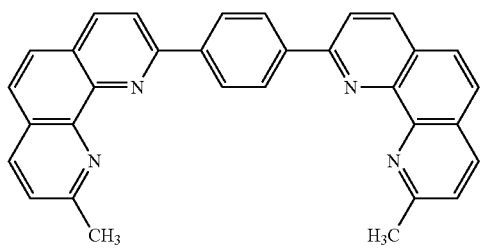
(B-65)
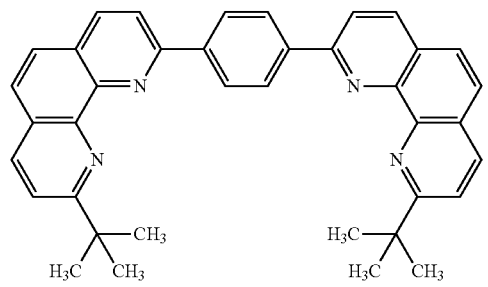
(B-66)
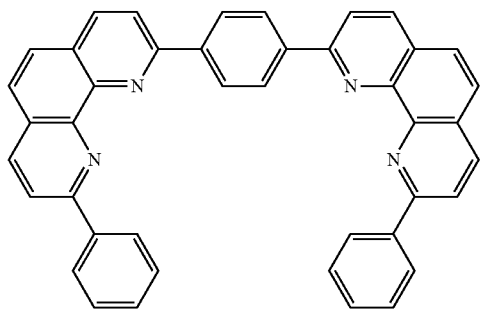
(B-67)

-continued
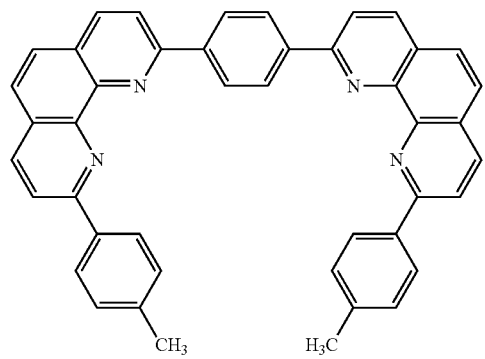
(B-68)
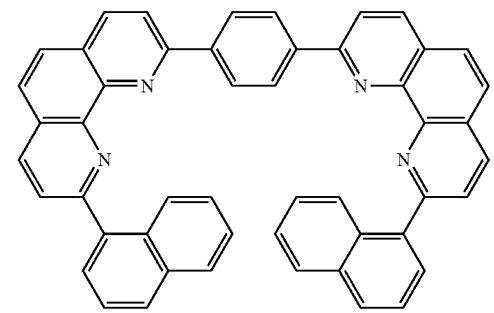
(B-69)
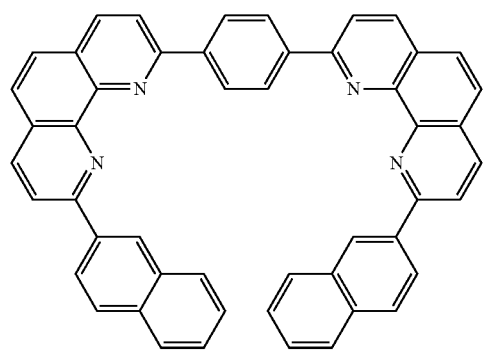
(B-70)
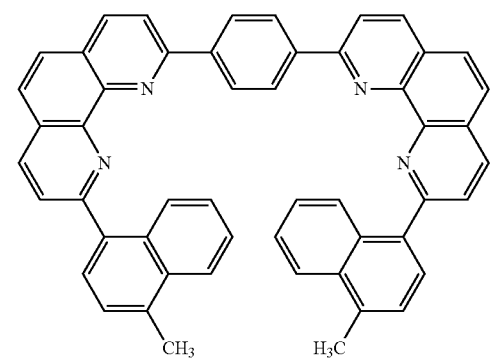
(B-71)
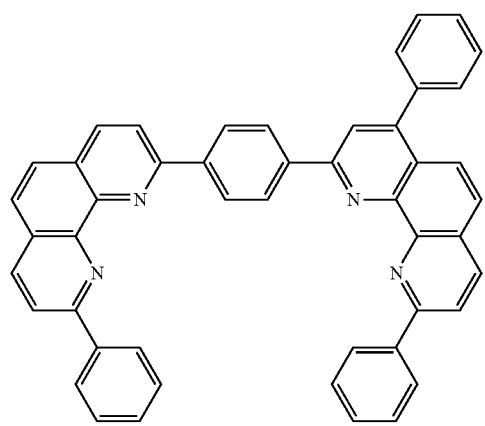
(B-72)
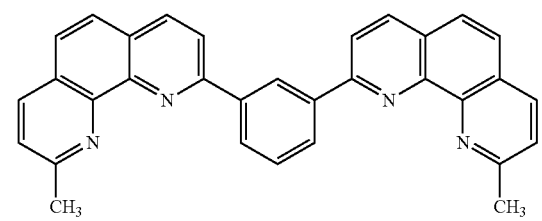
(B-73)
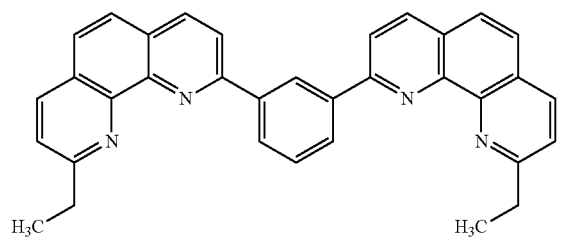
(B-74)
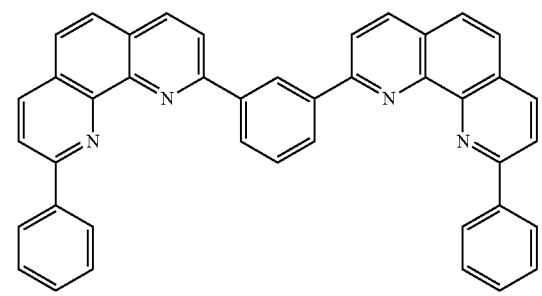
(B-75)

-continued
(B-76)
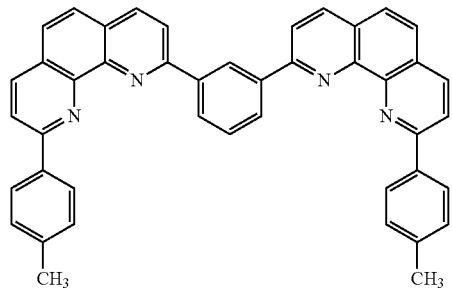
(B-77)
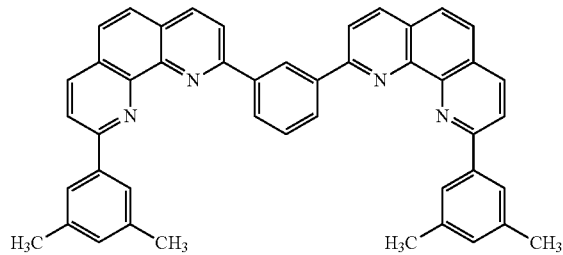
(B-78)
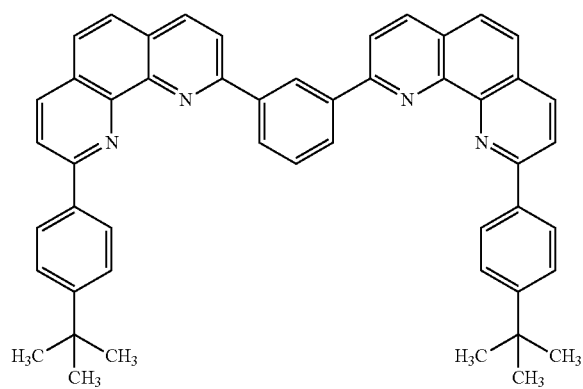
(B-79)
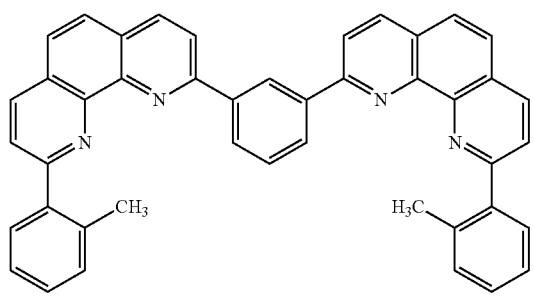
(B-80)
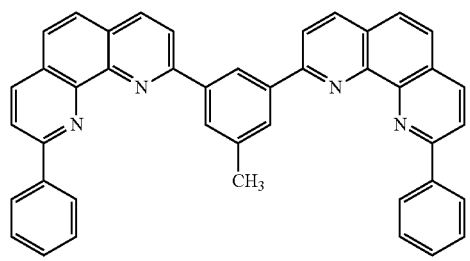
(B-81)
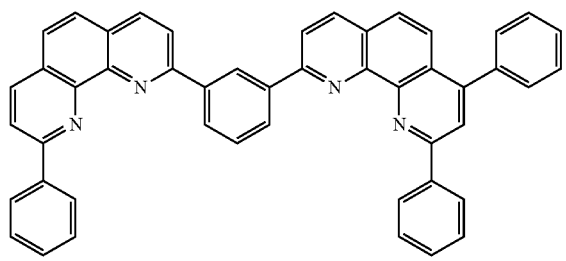
(B-82)
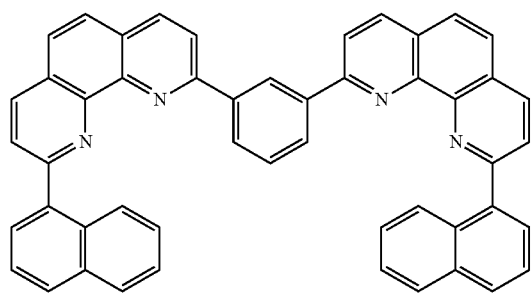
(B-83)
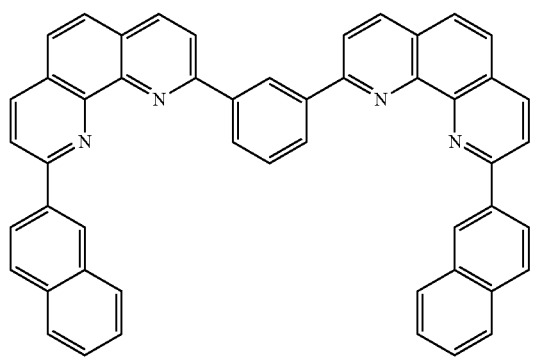

(B-84)
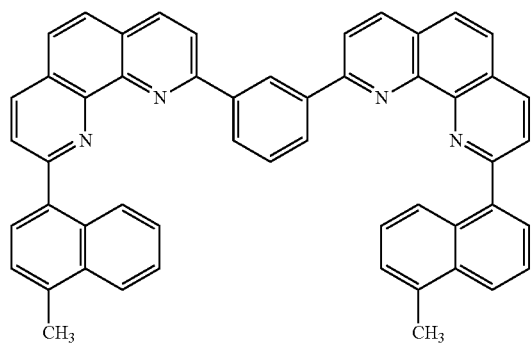
(B-85)
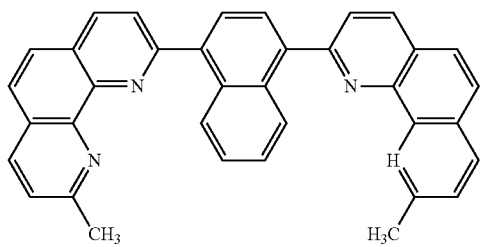
(B-86)
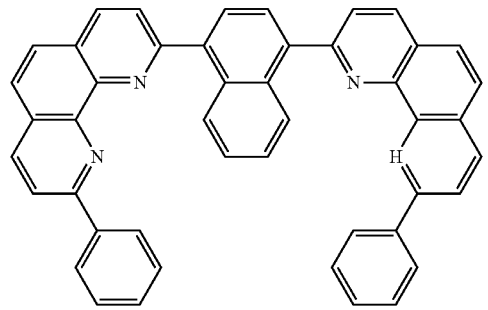
(B-87)
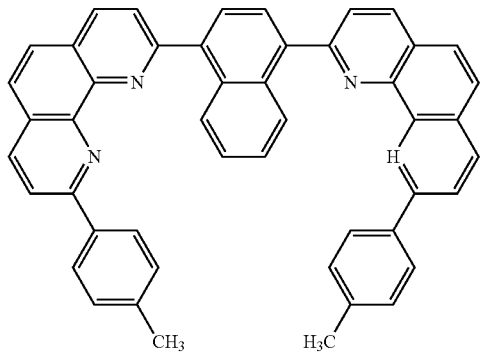
(B-88)
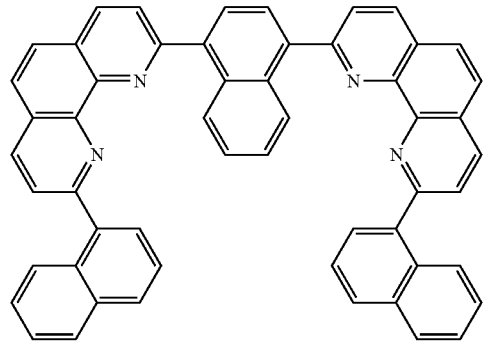
(B-89)
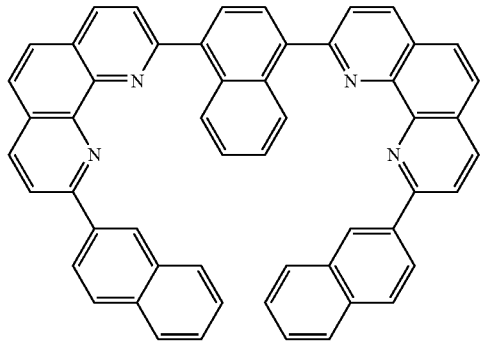
(B-90)
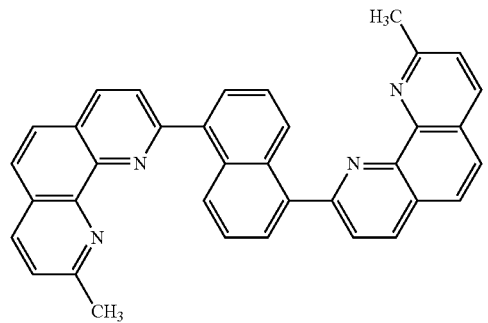
(B-91)
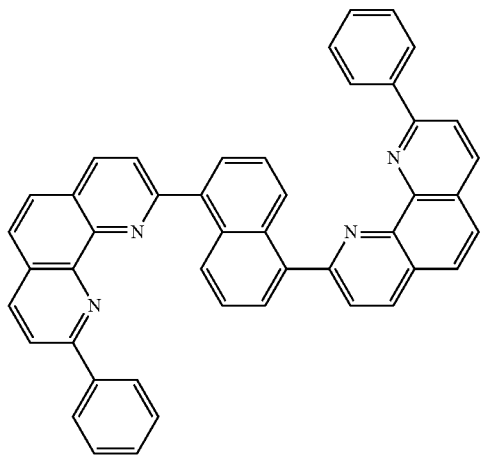

-continued
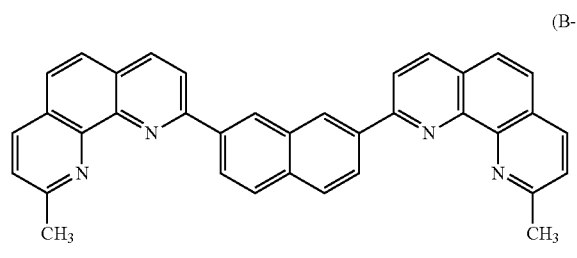
(B-92)
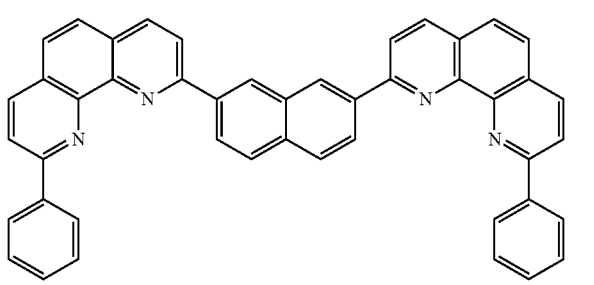
(B-93)
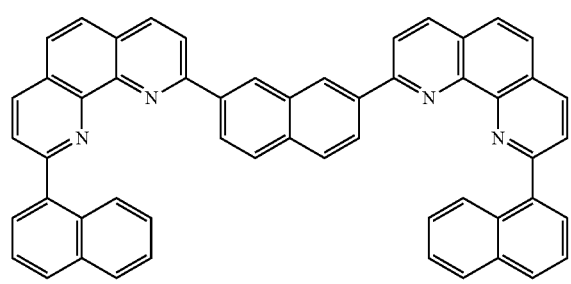
(B-94)
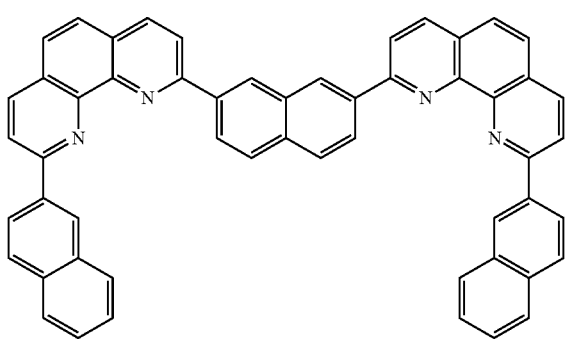
(B-96)
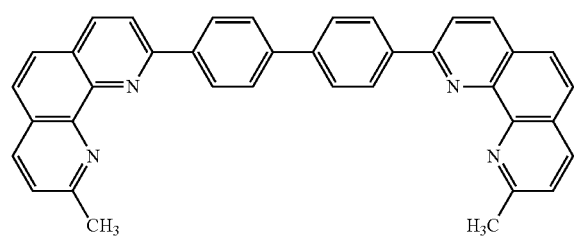
(B-97)
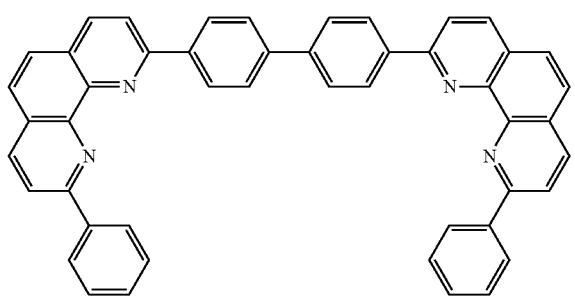
(B-98)
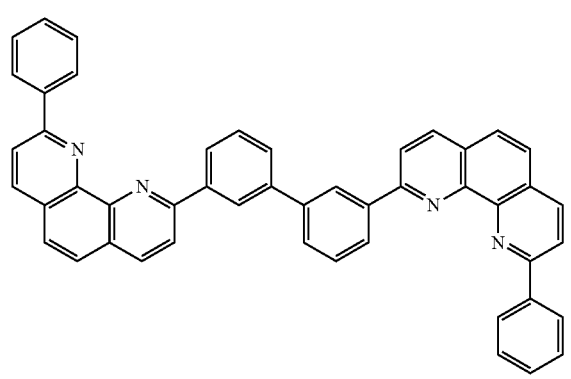
(B-99)
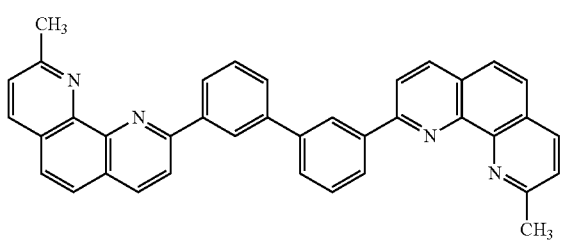
(B-100)

-continued

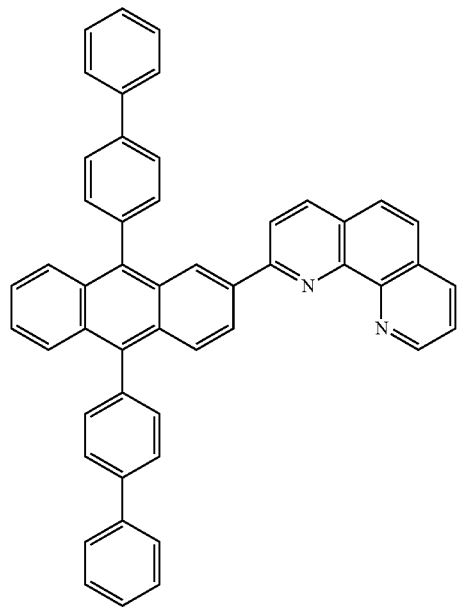
(B-101)

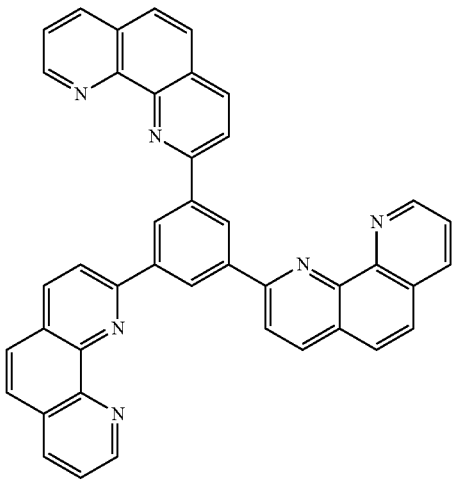
(B-102)

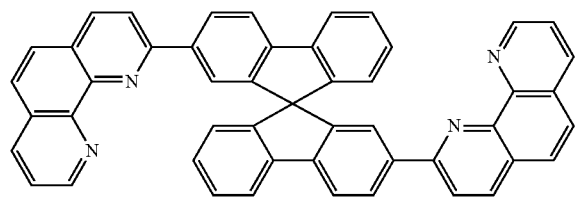
(B-103)

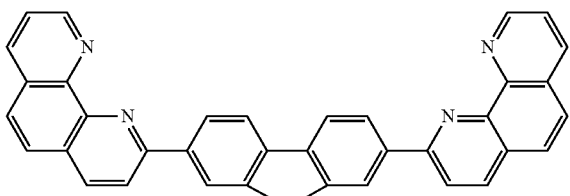
(B-104)

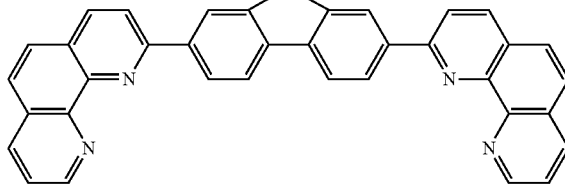
(B-105)

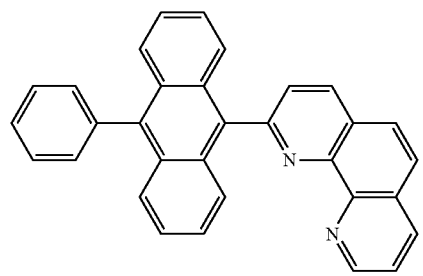

As for the synthesis of the compound represented by the formulas (I) and (II), reference can be made to WO2007/018004, WO2006/64484 and WO2006/021982.

In the invention, it is preferred that the donor-containing layer contain at least one of an electron-donating metal, an electron-donating metal compound and an electron-donating metal complex in addition to the above-mentioned compound represented by the formula (I) or (II).

Specifically, it is preferred that the donor-containing layer be a layer that contain at least one selected from an alkali metal, an alkali metal compound, an organic metal complex containing an alkali metal, an alkaline earth metal, an alkaline earth metal compound, an organic metal complex containing an alkaline earth metal, a rare earth metal, a rare earth metal compound and an organic metal complex containing a rare earth metal. Among these, it is preferred that the donor-containing layer contain at least one of an alkali metal, an alkaline earth metal, a simple substance of a rare earth metal, a compound of a rare earth metal and a complex of a rare earth metal.

As the alkali metal, lithium (Li), sodium (Na), potassium (K), rubidium (Rb), cesium (Cs) and the like can be given. One having a work function of 2.9 eV or less is particularly preferable. Among them, Li, K, Rb and Cs are preferable. Li, Rb or Cs is further preferable. Li is most preferable.

As the alkaline-earth metal, calcium (Ca), magnesium (Mg), strontium (Sr), barium (Ba) and the like can be given. One having a work function of 2.9 eV or less is particularly preferable.

As the rare-earth metal, scandium (Sc), yttrium (Y), cerium (Ce), terbium (Tb), ytterbium (Yb) and the like can be given. One having a work function of 2.9 eV or less is particularly preferable.

Among the above-mentioned metals, preferable metals have a particularly high reducing ability, and hence enable the resulting organic EL device to have an excellent luminance and a prolonged life by adding a relative small amount to an electron-injecting region.

Examples of the alkali metal compound include an alkali oxide such as lithium oxide ($Li_2O$), cesium oxide ($Cs_2O$) or potassium oxide ($K_2O$), and an alkali halide such as lithium fluoride (LiF), sodium fluoride (NaF), cesium fluoride (CsF) or potassium fluoride (KF). Among them, lithium fluoride (LiF), lithium oxide ($Li_2O$) and sodium fluoride (NaF) are preferable.

Examples of the alkaline-earth metal compound include barium oxide (BaO), strontium oxide (SrO), calcium oxide (CaO), and mixtures thereof such as barium strontium acid ($Ba_xSr_{1-x}O$) ($0<x<1$) and barium calcium acid ($Ba_xCa_{1-x}O$) ($0<x<1$). Among them, BaO, SrO and CaO are preferred.

Examples of the rare-earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). Among these, $YbF_3$, $ScF_3$ and $TbF_3$ are preferable.

The organic metal complexes are not particularly limited as long as they contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluoboran, bipyridyl, phenanthroline, phthalocyanine, porphyrin, cyclopentadiene, β-diketones, azomethines, and derivatives thereof.

Regarding the addition form of the metal, the compound and the complex as mentioned above, it is preferred that the metal, the compound and the complex be formed in the shape of a layer or an island in the interfacial region. A preferred method for the formation is a method in which an organic substance as a light emitting material or an electron-injecting material for forming the interfacial region is deposited simultaneously with the deposition of at least one of the metal, the compound and the complex by a resistant heating deposition method, thereby dispersing at least one of the metal, the compound and the complex in the organic substance. The dispersion concentration of the organic substance to the metal, the compound and the complex as mentioned above in terms of thickness ratio is normally 1000:1 to 1:1000, preferably 100:1 to 1:1.

In the case where at least one of the metal, the compound and the complex is formed into the shape of a layer, the light-emitting material or electron-injecting material which serves as an organic layer in the interface is formed into the shape of a layer. After that, at least one of the metal, the compound and the complex is solely deposited by the resistant heating deposition method to form a layer preferably having a thickness of 0.1 nm or more and 15 nm or less.

In the case where at least one of the metal, the compound and the complex is formed into the shape of an island, the light emitting material or the electron-injecting material which serves as an organic layer in the interface is formed into the shape of an island. After that, at least one of the metal, the compound and the complex is solely deposited by the resistant heating deposition method to form an island preferably having a thickness of 0.05 nm or more and 1 nm or less.

In addition, the ratio of the main component to at least one of the metal, the compound and the complex mentioned above in the organic EL device according to one aspect of the invention is preferably the main component: electron-donating dopant and/or the organic metal complex=100:1 to 1:1 in terms of film thickness ratio, with 50:1 to 4:1 being further preferable.

The film thickness of the donor-containing layer is preferably 0.1 nm to 100 nm, with 1 nm to 50 nm being particularly preferable.

It suffices that the organic EL device according to one aspect of the invention uses a compound represented by the formula (I) or (II) in a donor-containing layer. Known elements in this technical field can be appropriately used in other constituting elements such as an anode, an organic thin film layer and a cathode.

Meanwhile, the configuration of the organic emitting device according to one aspect of the invention is not limited to one shown in FIG. 1. For example, a hole-transporting layer and a hole-injecting layer can be omitted since they are optional layers. It is possible to provide an electron-transporting layer or the like between an emitting layer and a donor-containing layer. A hole-transporting layer, a hole-injecting layer, an emitting layer, an electron-transporting layer and the like correspond to the organic thin film layer according to one aspect of the invention.

Also, a buffer layer can be formed between a cathode and an acceptor-containing layer. Reference can be made to Japanese Patent No. 4392050 concerning the buffer layer.

Moreover, the organic emitting device of the invention can be used in an organic EL device (MPE device) having a configuration in which a plurality of emitting units each comprising organic layers including at least an emitting layer are stacked with a charge-generating layer being disposed between an anode and a cathode.

The organic EL device according to one aspect of the invention may be of top-emission type or bottom-emission type. In both cases, light is outcoupled through a cathode in the invention. The light-transmissive cathode is defined as a cathode having preferably 10% or more of transmittance of light in the visible range (450 to 650 nm), preferably 30% or more, more preferably 50% or more.

As examples of a material constituting the light-transmissive cathode, ITO, tin oxide (NESA), an alloy of indium oxide and zinc (IZO), zinc oxide (ZnO), IZO/Ag/IZO, ITO/Ag/ITO or the like can be given.

As the acceptor-containing layer, an easy-reducible organic compound can be used.

The easiness of reduction of a compound can be measured by a reduction potential. In the invention, in terms of a reduction potential obtained by using a saturated calomel electrode (SCE) as a reference electrode, it is preferable to use a compound having a reduction potential of −0.8V or more, more preferably −0.3V or more. It is particularly preferable to use a compound having a reduction potential larger than that of tetracyanoquinodimethane (TCNQ) (about 0V).

In the invention, as the acceptor-containing layer, a layer comprising a compound represented by the following formula (III) can be given. This compound is resistant to damage caused by sputtering, and, due to its high adhesiveness (contact properties) with the donor-containing layer or the cathode, it contributes to prolongation of the life of a device.

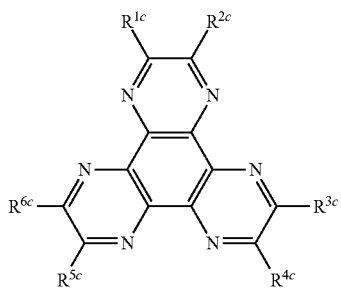

(III)

$R^{1c}$ to $R^{6c}$ in the formula are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 ring carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group substituted with a substituted or unsubstituted aryl group including 6 to 50 ring carbon atoms, a halogen atom, a cyano group, a nitro group, a hydroxyl group or a carboxyl group.

Specific examples of the substituted or unsubstituted aryl group including 6 to 60 ring carbon atoms or the like are the same as the examples of the compound in the formula (I) or the like.

Specific examples of the compound represented by the formula (III) are shown below.

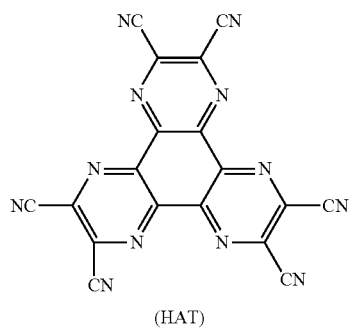

(HAT)

Further, a layer containing the compound represented by the following formula (IV) can be mentioned. By combining the dope-containing layer according to one aspect of the invention and the layer containing the compound represented by the formula (IV), effects of improving properties such as the luminance of a device, lowering in driving voltage and prolongation of a life, etc. become significant.

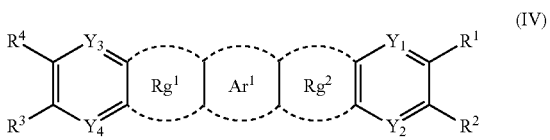

(IV)

In the above formula (IV), $Ar^1$ is an aromatic ring including 6 to 24 ring carbon atoms or a heterocyclic ring including 5 to 24 ring atoms. Preferably, $Ar^1$ is an aromatic ring including 6 to 14 ring carbon atoms or a heterocyclic ring including 5 to 14 ring atoms. As the aromatic ring, a benzene ring, a naphthalene ring, a fluorene ring, a 9,9-dimethylfluorene ring, a 9,9-dioctylfluorene ring and the like can be given. As the heterocyclic ring, a pyrazine ring, a pyridine ring, a quinoxaline ring, a thiophene ring, a benzothiophene ring, a dibenzothiophene ring, a furan ring, a benzofuran ring, a dibenzofuran ring, a phenanthroline ring, a naphthyridine ring, a tetraaza-anthracene ring and the like can be given. The aromatic ring and the heterocyclic ring may be substituted with a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group, as represented by $R^1$ to $R^4$ given below.

In the formula (IV), $R^1$ to $R^4$ may be the same or different from each other, and are a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group. $R^1$ and $R^2$ may be bonded each other to form a ring and $R^3$ and $R^4$ may be bonded each other to form a ring.

Examples of the alkyl group include a methyl group, an ethyl group, an n-propyl group, an isopropyl group, an n-butyl group, an isobutyl group, a tert-butyl group and an octyl group.

As the cycloalkyl group, a cyclopentyl group, a cyclohexyl group or the like can be given.

As the alkenyl group, a vinyl group, a propenyl group (including a regioisomer of a double bond), a butenyl group (including a regioisomer of a double bond), a pentenyl group (including a regioisomer of a double bond) or the like can be given.

As the (substituted) aryl group, a phenyl group, a biphenyl group, a naphthyl group, a fluorophenyl group, a trifluoromethylphenyl group, a (trifluoromethyl)fluorophenyl group, a trifluorophenyl group, a bis(trifluoromethyl)phenyl group, a (trifluoromethyl)difluorophenyl group, a trifluoromethoxyphenyl group, a trifluoromethoxyfluorophenyl group or the like can be given.

As the heterocyclic group, residues of pyridine, pyrazine, furan, imidazole, benzimidazole, thiophene or the like can be given.

As the halogen atom, a fluorine atom, a chlorine atom, a bromine atom or an iodine atom can be mentioned.

As the fluoroalkyl group, a trifluoromethyl group, a pentafluoroethyl group, a perfluorocyclohexyl group, a perfluoroadamantyl group or the like can be mentioned.

As the alkoxy group, a methoxy group, an ethoxy group or the like can be mentioned.

As the fluoroalkoxy group, a trifluoromethoxy group, a pentafluoroethoxy group, a 2,2,2-trifluoroethoxy group, a 2,2,3,3,3-pentafluoropropoxy group, a 2,2,3,3-tetrafluoropropoxy group, a 1,1,1,3,3,3-hexafluoropropane-2-yloxy group or the like can be mentioned.

As the (substituted) aryloxy group, a phenyloxy group, a pentafluorophenyloxy group, a 4-trifluorophenyloxy group or the like can be mentioned.

As the (substituted) aralkyloxy group, a benzyloxy group, a pentafluorobenzyloxy group, a 4-trifluoromethylbenzyloxy group or the like can be mentioned.

As the (substituted) amino group, an amino group, a mono- or dimethylamino group, a mono- or diethylamino group, a mono- or diphenylamino group or the like can be mentioned.

As the (substituted) silyl group, a silyl group, a mono-, di- or trimethylsilyl group, a mono-, di- or triethylsilyl group, a mono-, di- or triphenylsilyl group or the like can be mentioned.

As the examples of the arbitral substituent of $R^1$ to $R^4$, the halogen atom, the cyano group, the alkyl group, the aryl group, the fluoroalkyl group, the fluoroalkoxy group and the heterocyclic group mentioned above can be given.

In the present application, unless otherwise specified, as the examples of the arbitral substituent when referring to the "substituted or unsubstituted", the halogen atom, the cyano group, the alkyl group, the aryl group, the fluoroalkly group, the fluoroalkoxy group and the heterocyclic group given above can be mentioned.

As mentioned above, $R^1$ and $R^2$ may be bonded with each other to form a ring and $R^3$ and $R^4$ may be bonded with each other to form a ring. As examples of the ring, a benzene ring, a naphthalene ring, a pyrazine ring, a pyridine ring, a furan ring or the like can be given.

At least one of $R^1$ to $R^4$ is preferably a fluorine atom, a fluoroalkyl group, a fluoroalkoxy group, a cyano group, or an aryl group or a heterocyclic group having at least one group selected from fluorine, a fluoroalkyl group, a fluoroalkoxy group and a cyano group. By having these groups as a substituent, electron acceptability can be enhanced, an appropriate sublimation temperature can be obtained or crystallization can be suppressed.

The $Rg^1$ and the $Rg^2$ in the formula (IV) may be the same or different from each other and are represented by the following formula (i) or (ii).

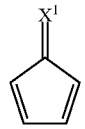

(i)

-continued

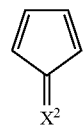

(ii)

In the above formula, $X^1$ and $X^2$ may be the same or different from each other and are any of divalent groups represented by the following (a) to (g). Divalent groups represented by (a), (b) or (c) are preferable in respect of excellent heat resistance, easiness in synthesis or the like.

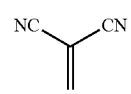

(a)

(b)

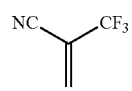

(c)

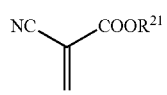

(d)

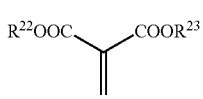

(e)

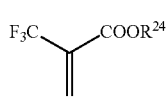

(f)

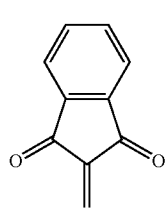

(g)

$R^{21}$ to $R^{24}$ in the above formula may be the same or different from each other, and are a hydrogen atom, a substituted or unsubstituted fluoroalkyl group, a substituted or unsubstituted alkyl group, a substituted or unsubstituted cycloalkyl group, a substituted or unsubstituted aryl group, a substituted or unsubstituted heterocyclic group, and $R^{22}$ and $R^{23}$ may be bonded each other to form a ring. As specific examples of the fluoroalkyl group, the alkyl group, the cycloalkyl group, the aryl group and the heterocyclic group, the groups mentioned above referring to $R^1$ to $R^4$ can be given.

$Y^1$ to $Y^4$ in the formula (IV) may be the same or different from each other, and are N, CH, or $C(R^5)$, wherein $R^5$ is the same as $R^1$ to $R^4$.

It is preferred that at least one of $Y^1$ to $Y^4$ be a nitrogen atom (the same applies to $Y^{21}$ to $Y^{26}$ and $Y^{31}$ to $Y^{38}$ mentioned later). If at least one of $Y^1$ to $Y^4$ is a nitrogen atom, electron acceptability can be enhanced, heat resistance can be increased or crystallization can be suppressed.

The indenofluorenedione derivative of the formula (IV) is preferably represented by the following formula (IV-A) or (IV-B). Symbols such as $Ar^1$ in the following formula (IV-A) have the same meanings as those in the formula (IV). $Ar^2$ in the following formula (IV-B) is the same as $Ar^1$ in the formula (IV). $X^3$ and $X^4$ are the same as $X^1$ and $X^2$ in the formula (IV). $Y^5$ to $Y^8$ are the same as $Y^1$ to $Y^4$ in the formula (IV). $R^1$ to $R^4$ are the same as $R^1$ to $R^4$ in the formula (IV).

(IV-A)
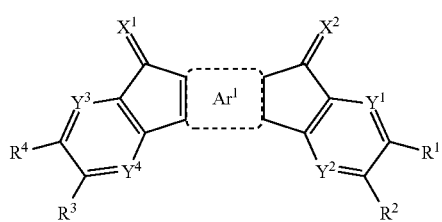

(IV-B)
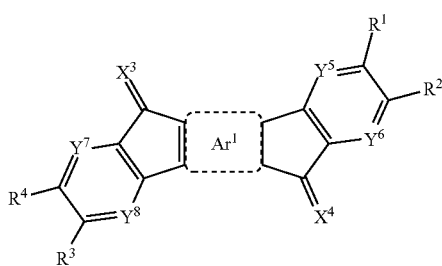

It is further preferred that the indenofluorenedione derivative in the formula (IV) be represented by the following formulas (IVa) to (IVi), (IVa)
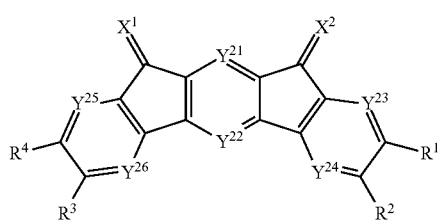

(IVb)
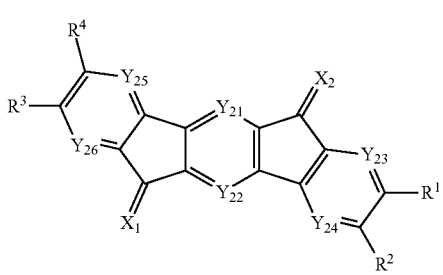

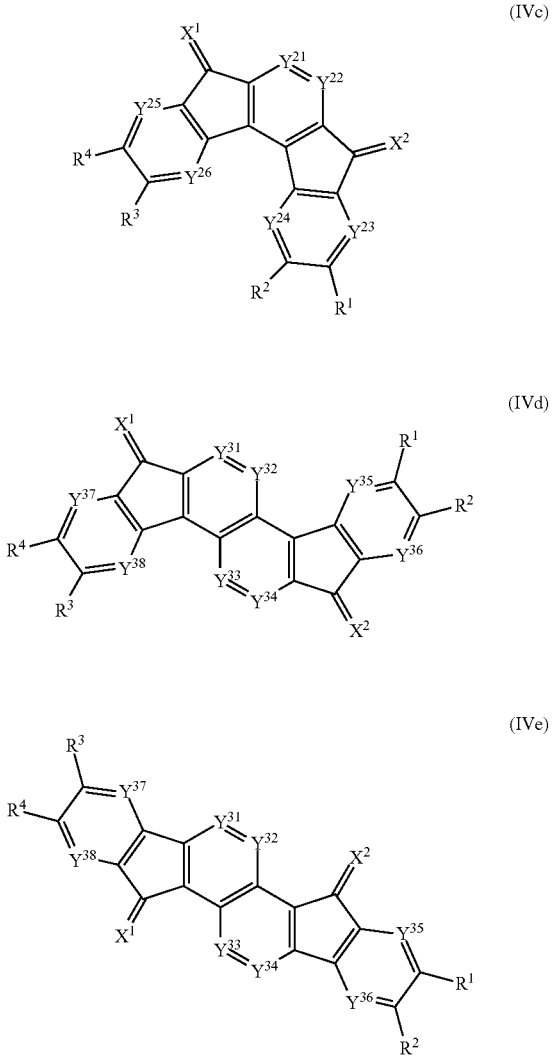

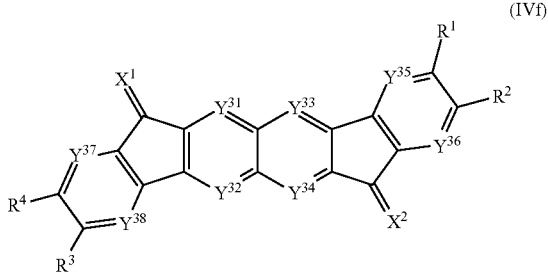

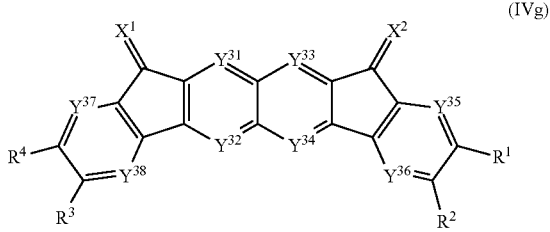

-continued

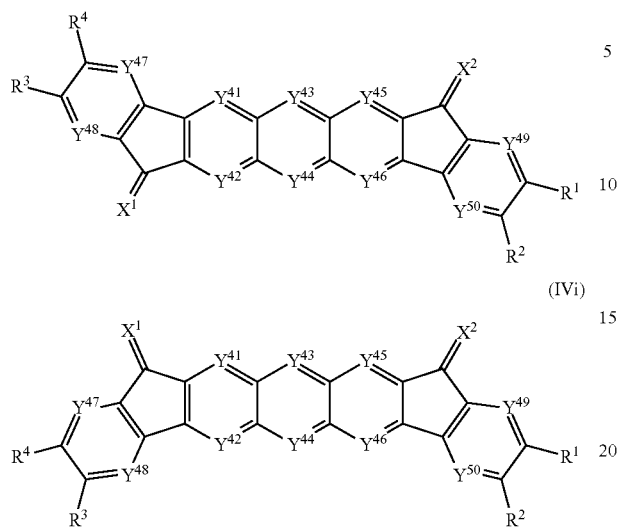
(IVh)

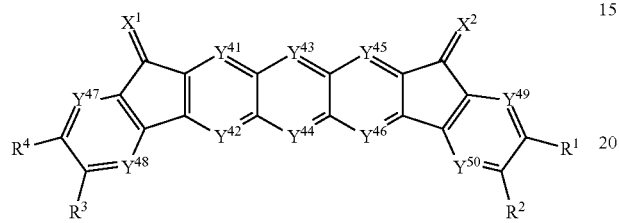
(IVi)

In the above formula, $X^1$ and $X^2$ and $R^1$ to $R^4$ are the same as $X^1$ and $X^2$ and $R^1$ to $R^4$ in the formula (IV) and $Y^{21}$ to $Y^{26}$, $Y^{31}$ to $Y^{38}$ and $Y^{41}$ to $Y^{50}$ are the same as $Y^1$ to $Y^4$ in the formula (IV).

Particularly preferable indenofluorenedione derivatives represented by the formula (IV) are represented by the following formulas (IV-a) to (IV-n). As for the following formula (IV-b), (IV-d), (IV-f), (IV-h), (IV-j), (IV-l), (IV-n), (IV-p) and (IV-r), a plurality of isomers are present due to the steric configuration of the cyano groups of the two cyanoimino groups. The invention is not limited to specific isomers. The derivative of the invention may be a specific isomer alone or may be a mixture of two or larger than two isomers.

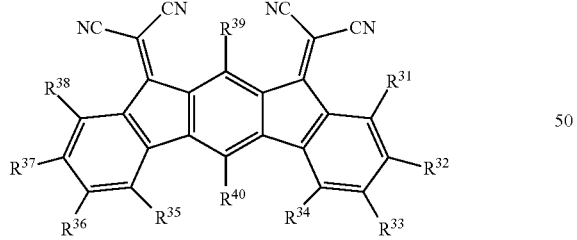
(IV-a)

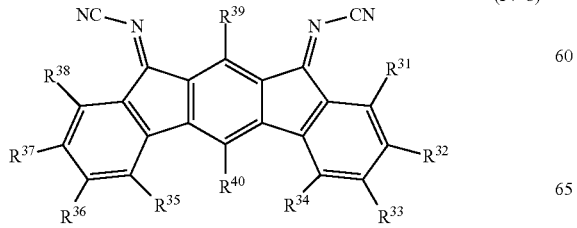
(IV-b)

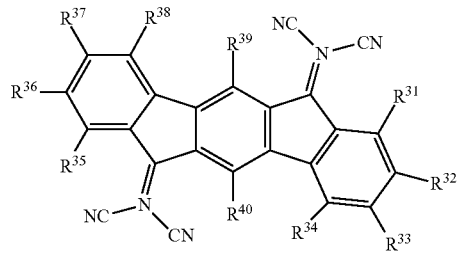
(IV-c)

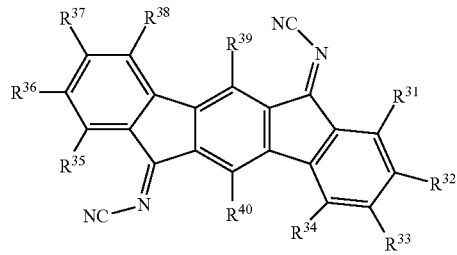
(IV-d)

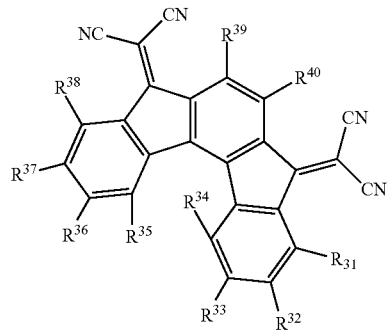
(IV-e)

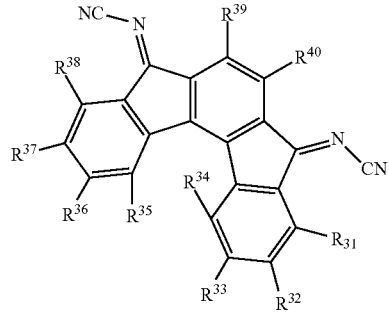
(IV-f)

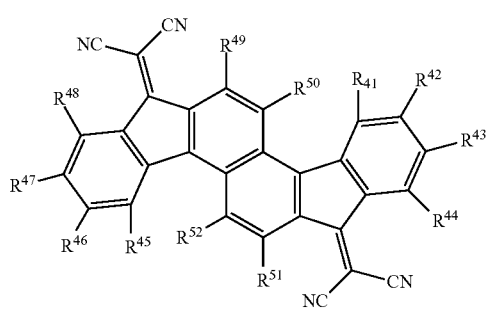
(IV-g)

-continued
(IV-h)
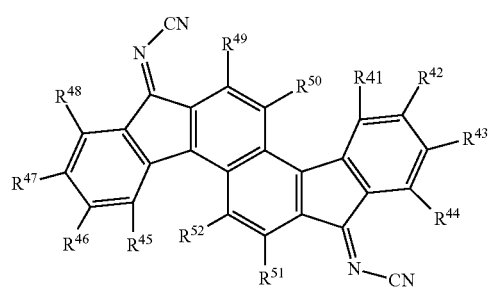
(IV-i)
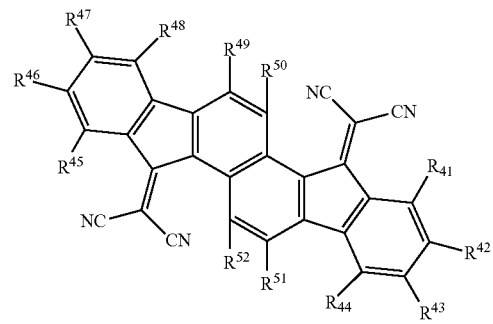
(IV-j)
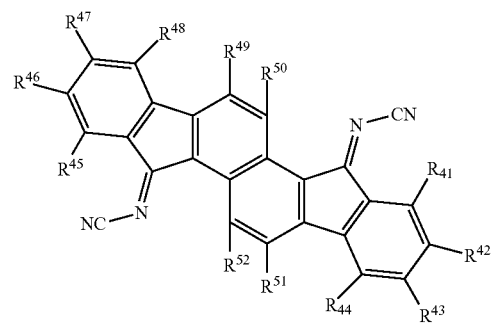
(IV-k)
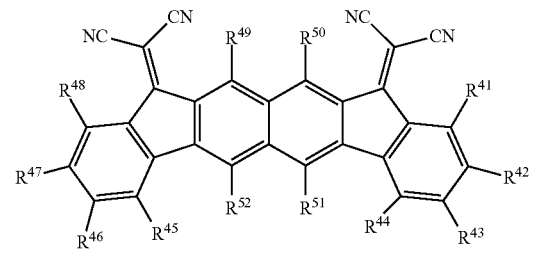
(IV-l)
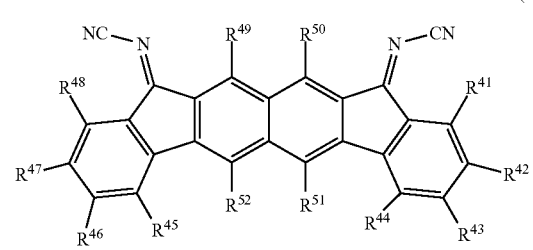
-continued
(IV-m)
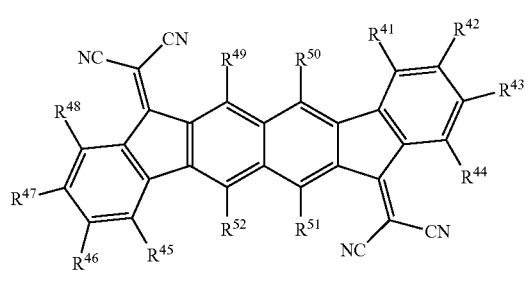
(IV-n)
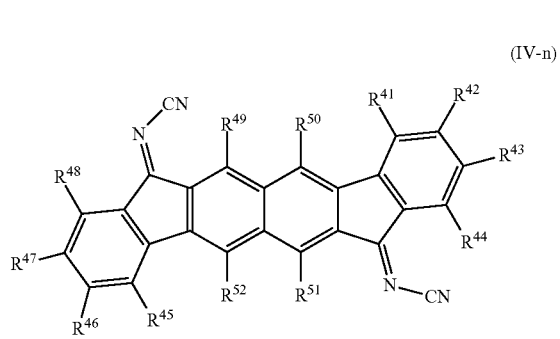
(IV-o)
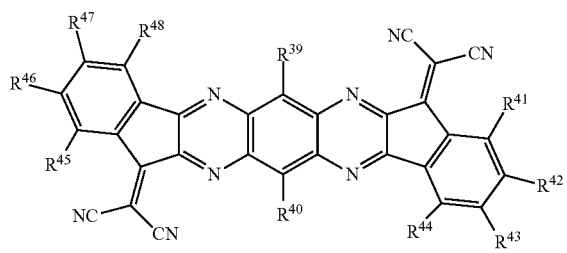
(IV-p)
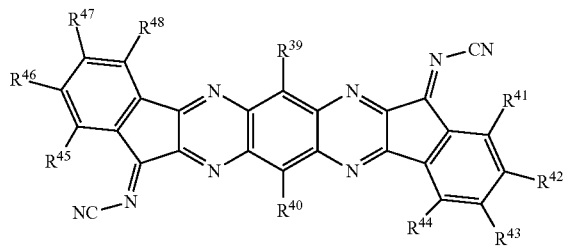
(IV-q)
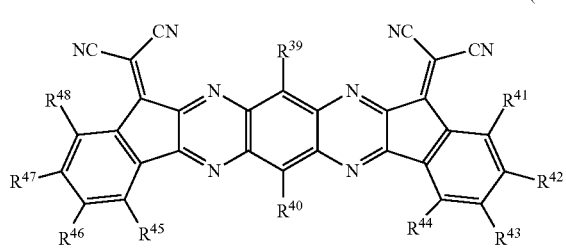

-continued

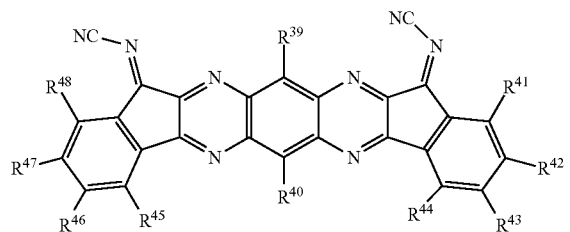
(IV-r)

In the above formulas, $R^{31}$ to $R^{52}$ have the same meanings as $R^1$ to $R^4$ in the formula (IV). Adjacent two of $R^{31}$ to $R^{52}$ may be bonded each other to form a ring. In particular, it is preferred that at least one of $R^{31}$ to $R^{52}$ be a fluorine atom, a fluoroalkyl group, a fluoroalkoxy group, a cyano group or an aryl group or a heterocyclic group having at least one selected from fluorine, a fluoroalkyl group, a fluoroalkoxy group and a cyano group.

Due to the structure represented by each of the above-mentioned formulas, the indenofluorenedione derivative has electron acceptability. Further, since it has excellent heat resistance and a sublimation temperature of about 200° C. or more, the indenofluorenedione derivative is capable of being purified by sublimation, whereby it can have high purity. Further, by using in an organic EL device, the driving voltage of the device can be lowered, and the life thereof can be prolonged. Further, since the sublimation temperature is as high as about 200° C. or more, the derivative does not scatter to the inside of the deposition apparatus at the time of producing a device. Accordingly, there is no fear that the derivative contaminates a film-forming apparatus or an organic EL device.

Specific examples of the indenofluorenedione derivative represented by the formula (IV) are given below. The derivative is not limited thereto.

(A-1)
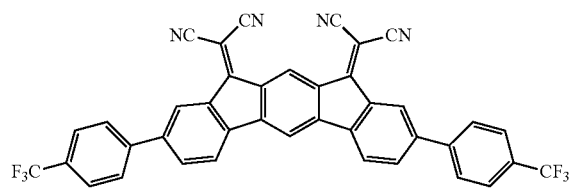

(A-2)
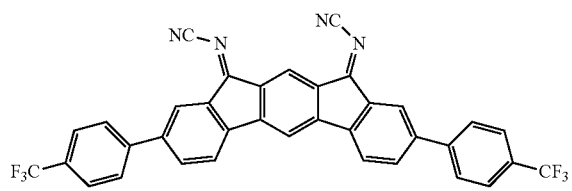

(A-3)
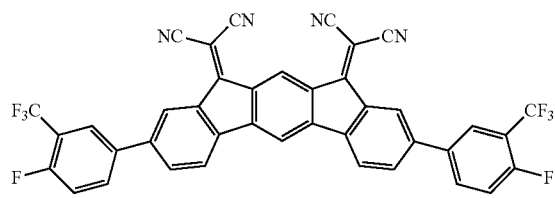

(A-4)
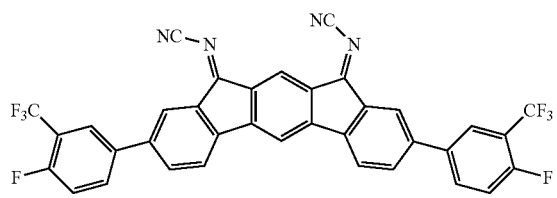

(A-5)
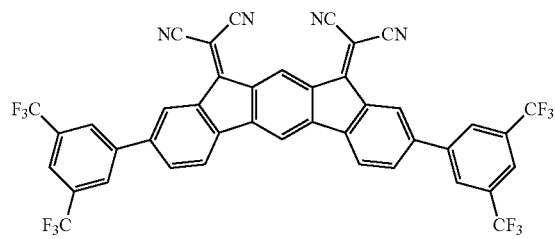

(A-6)
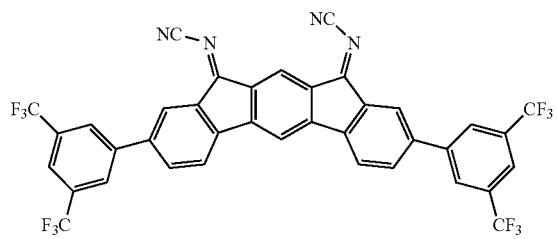

(A-7)
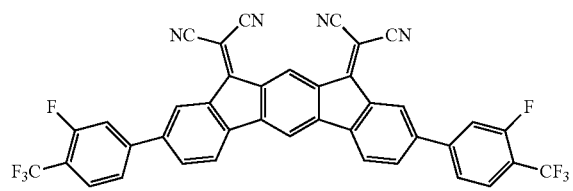

(A-8)
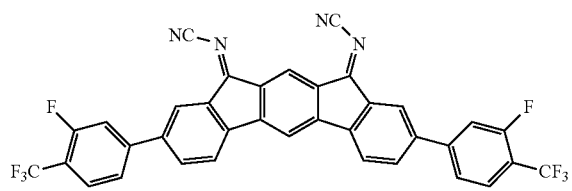

-continued
(A-9)
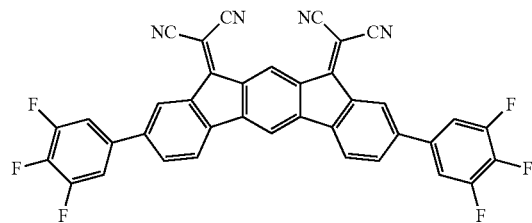
(A-10)
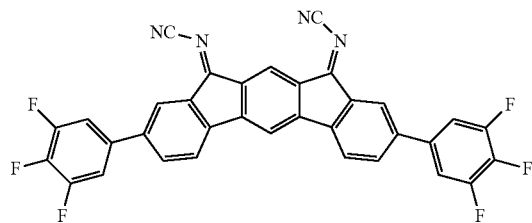
(A-11)
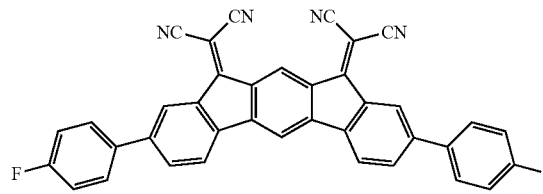
(A-12)
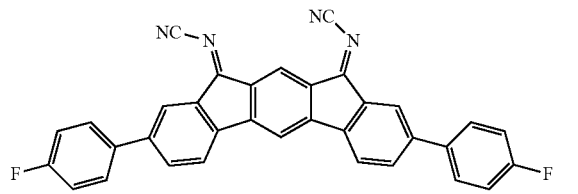
(A-13)
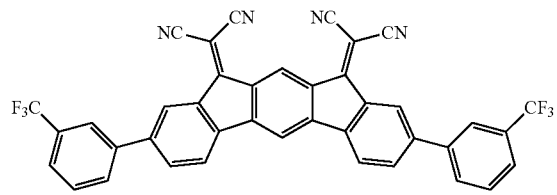
(A-14)
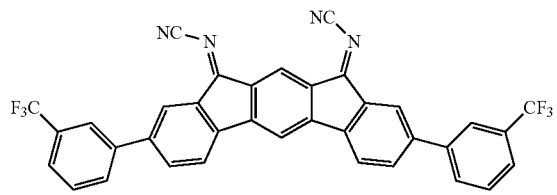
(A-15)
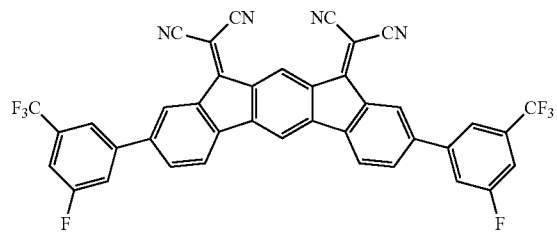
(A-16)
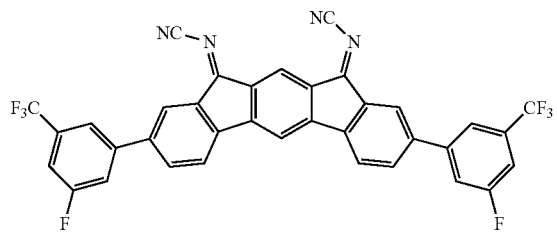
(A-17)
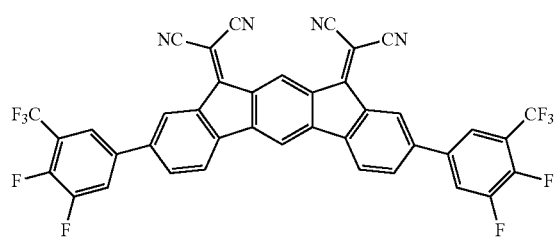
(A-18)
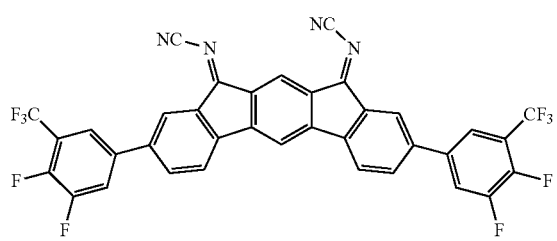
(A-19)
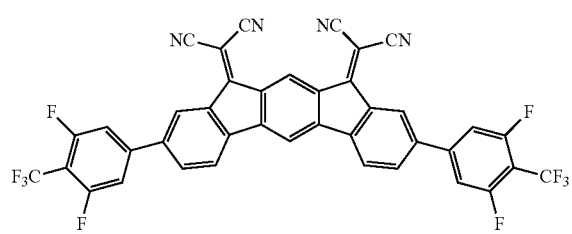
(A-20)
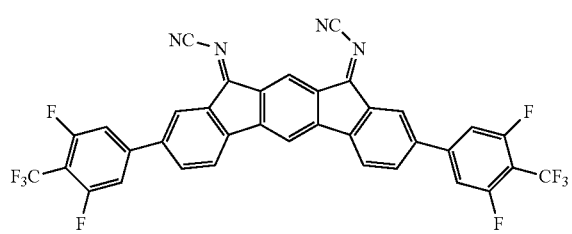

-continued
(A-21)
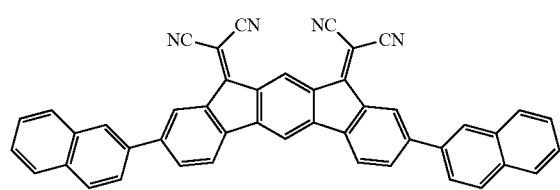
(A-22)
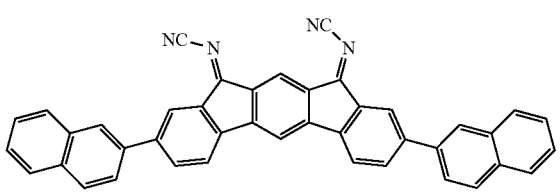
(A-23)
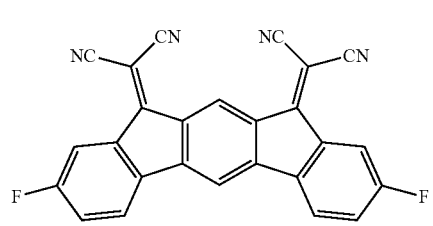
(A-24)
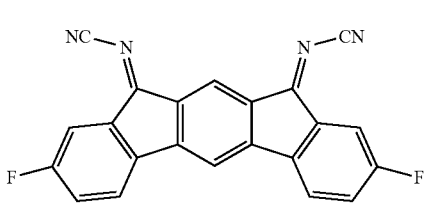
(A-25)
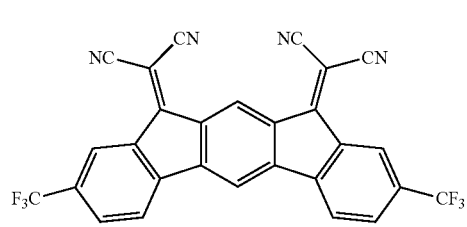
(A-26)
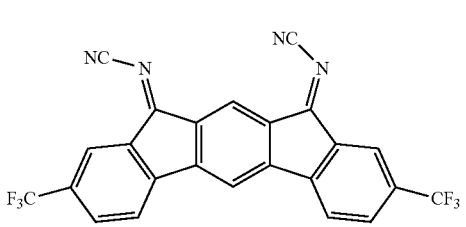
(A-27)
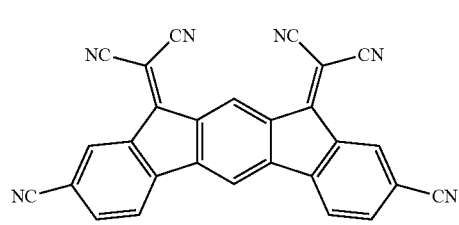
(A-28)
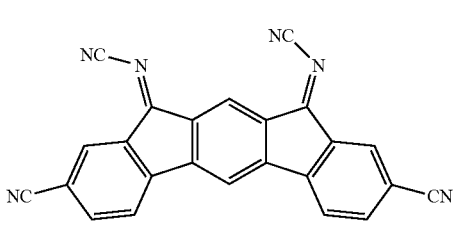
(A-29)
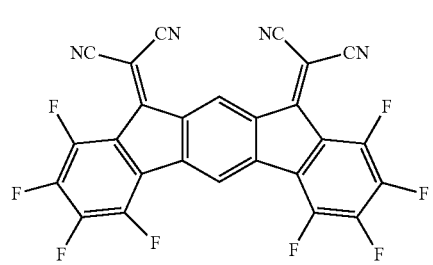
(A-30)
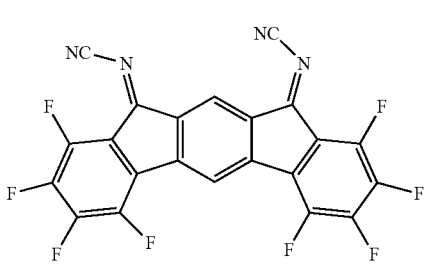
(A-31)
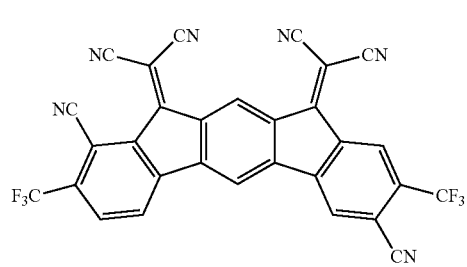
(A-32)
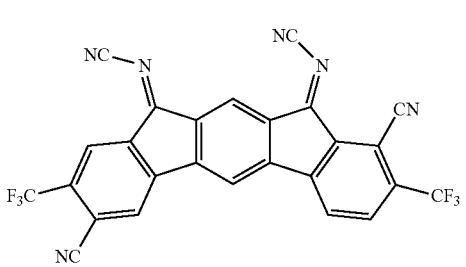

-continued
(A-33)
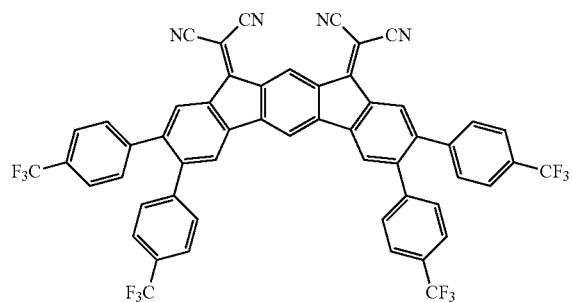
(A-34)
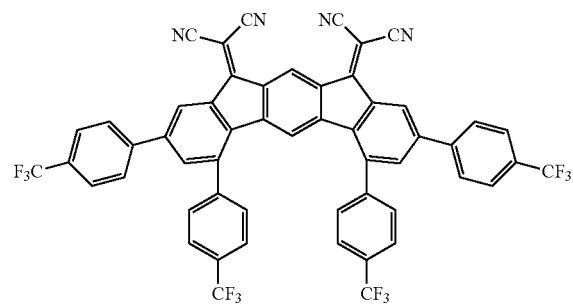
(A-35)
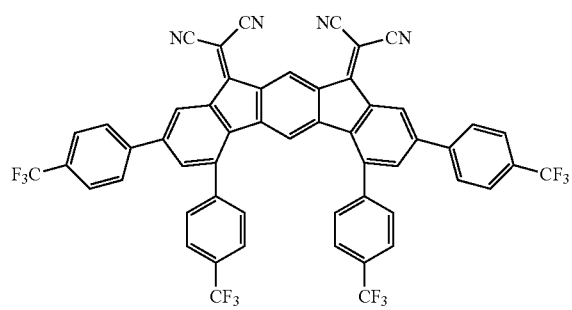
(A-36)
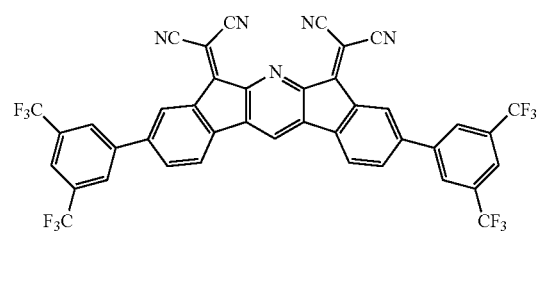
(A-37)
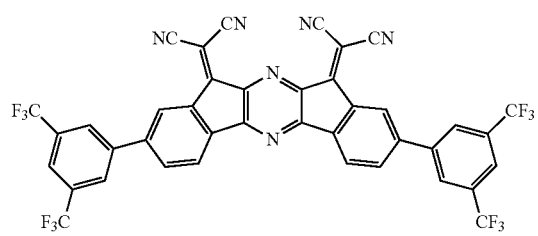
(A-38)
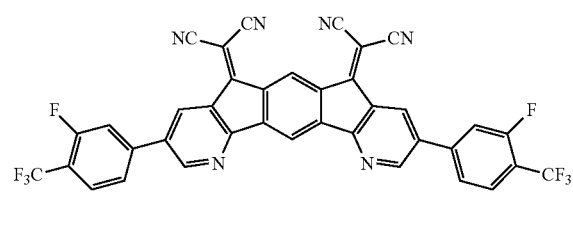
(A-39)
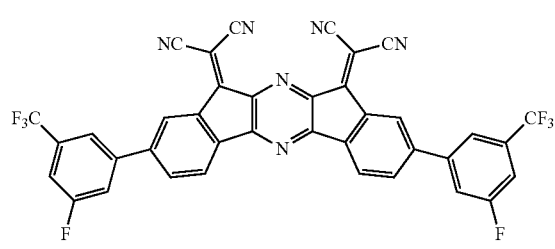
(A-40)
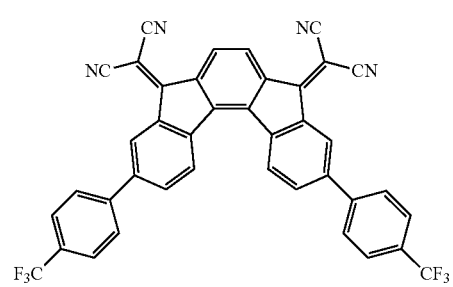
(A-41)
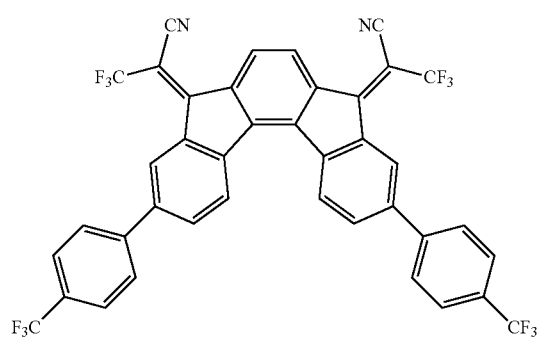
(A-42)
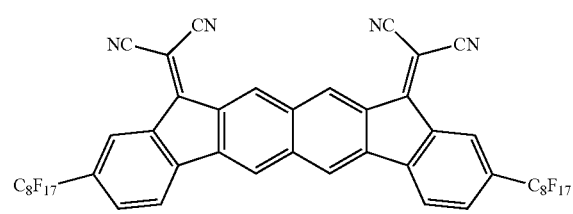

-continued
(A-43)
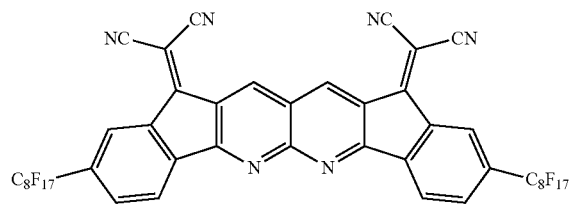
(A-44)
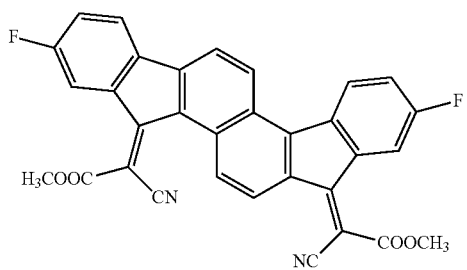
(A-45)
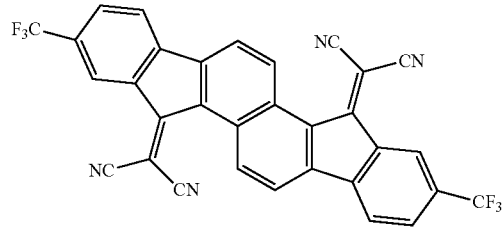
(A-46)
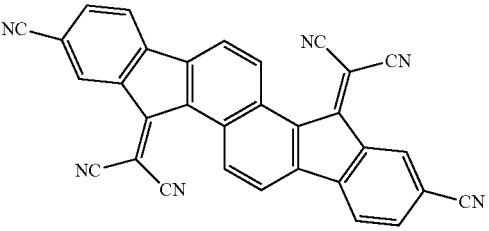
(A-47)
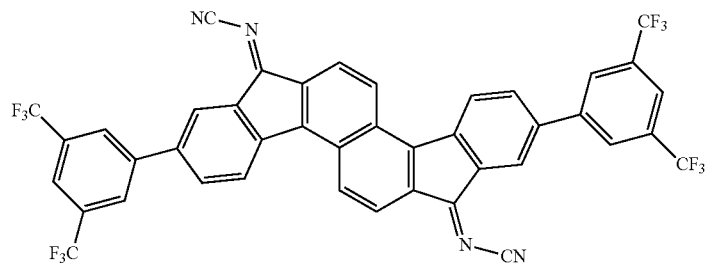
(A-48)
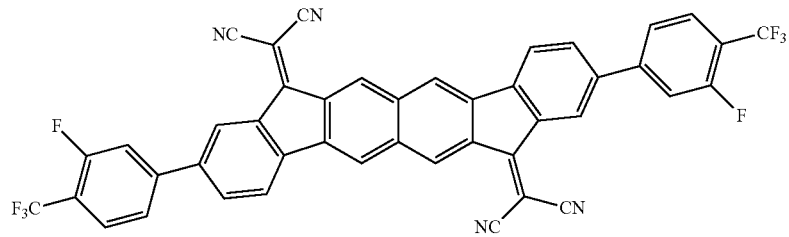
(A-49)
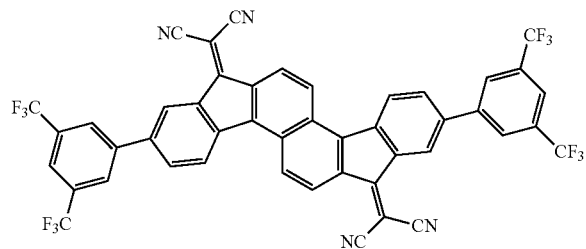
(A-50)
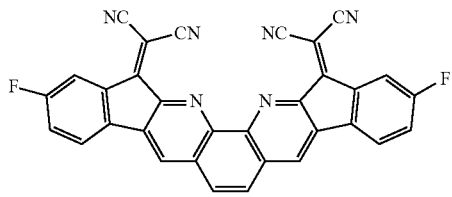
(A-51)
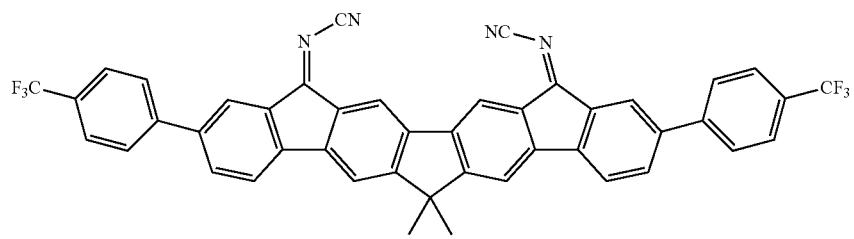

-continued
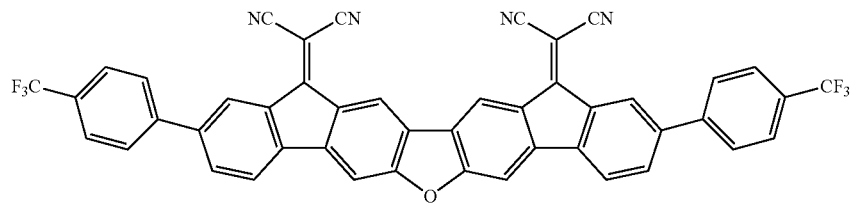
(A-52)
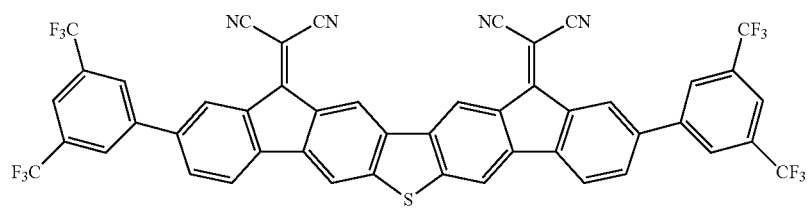
(A-53)
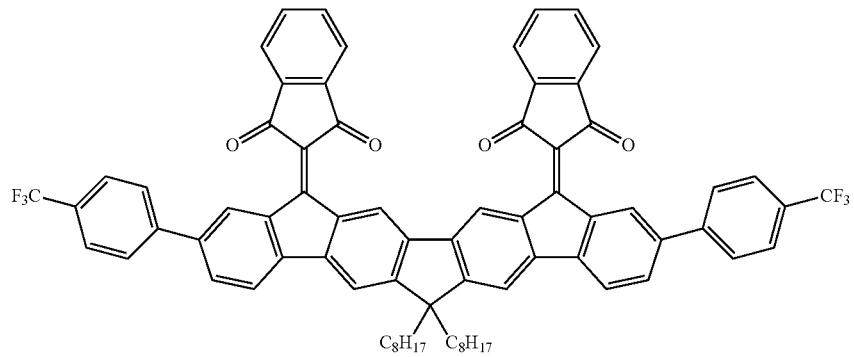
(A-54)
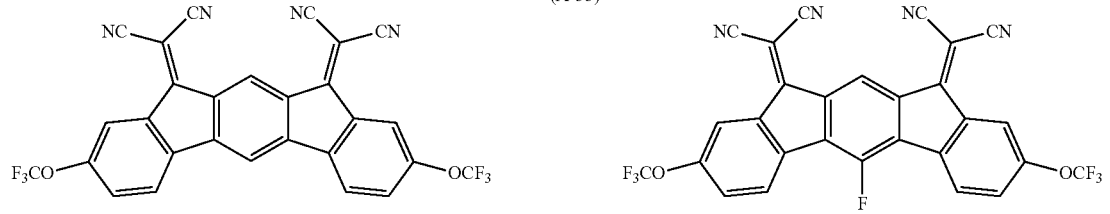
(A-55) (A-56)
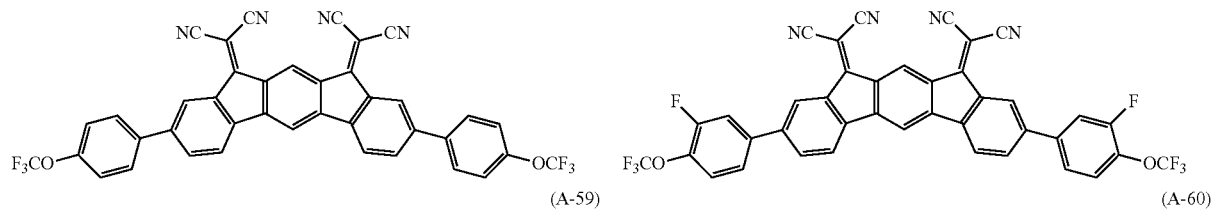
(A-57) (A-58)
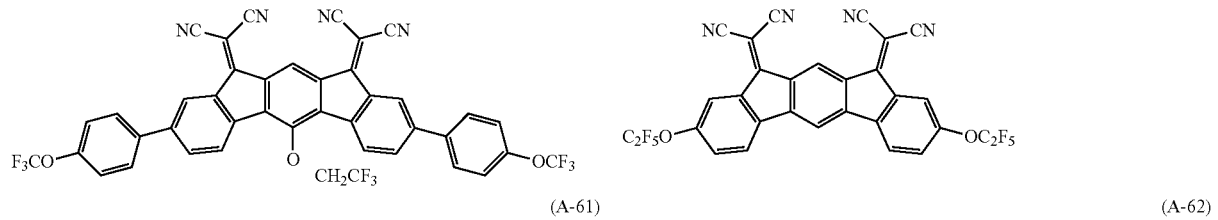
(A-59) (A-60)
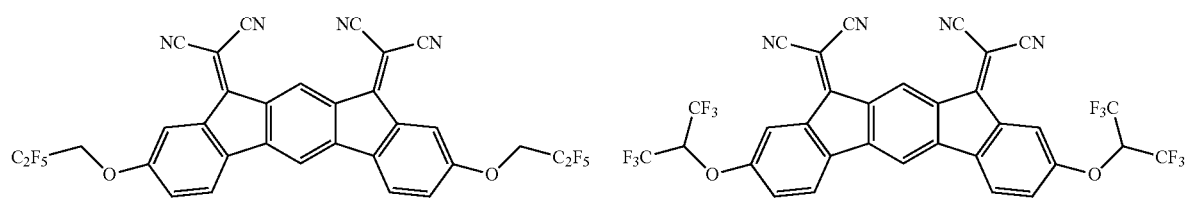
(A-61) (A-62)

-continued
(A-63)
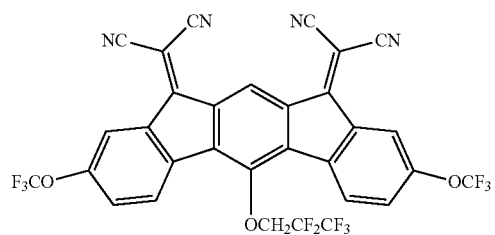
(A-64)
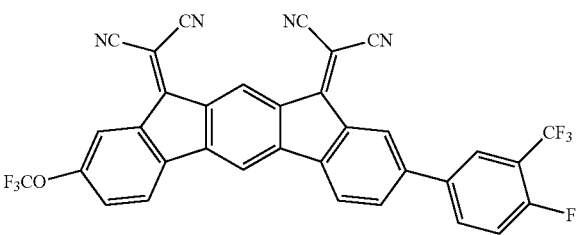
(A-65)
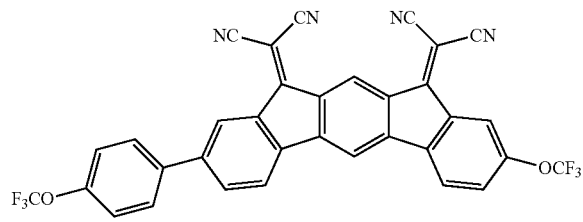
(A-66)
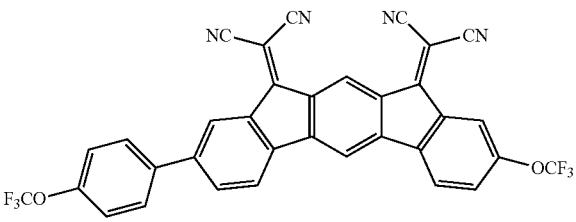
(A-67)
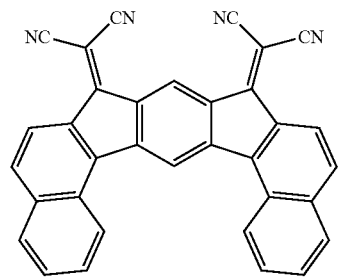
(A-68)
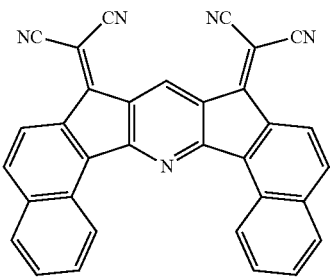
(A-69)
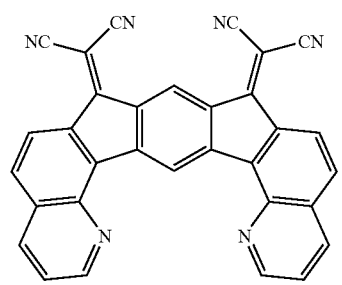
(A-70)
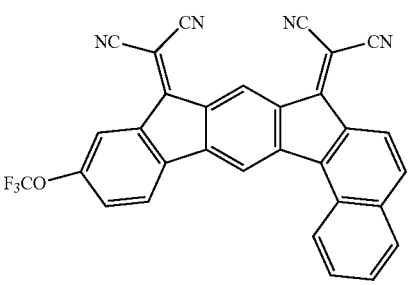
(A-71)
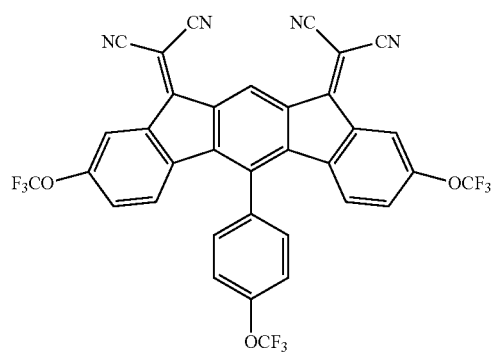
(A-72)
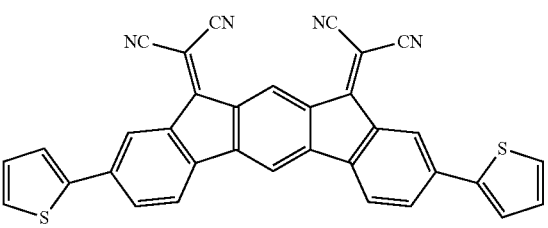
(A-73)
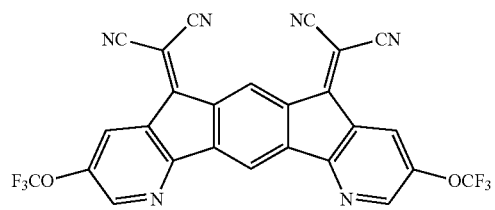
(A-74)

-continued
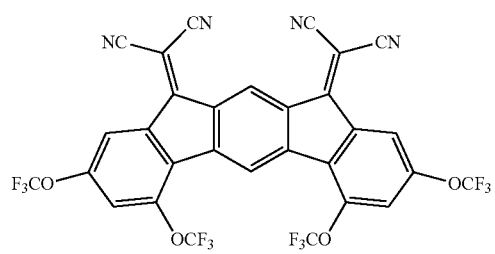
(A-75)
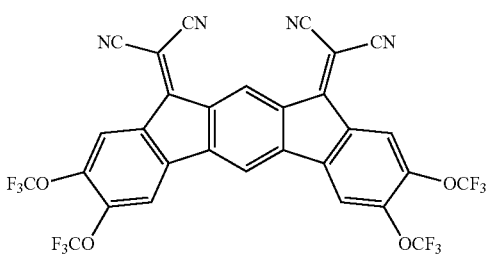
(A-76)
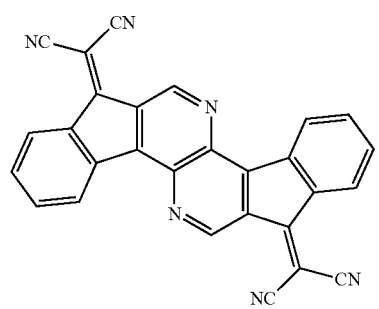
(A-77)
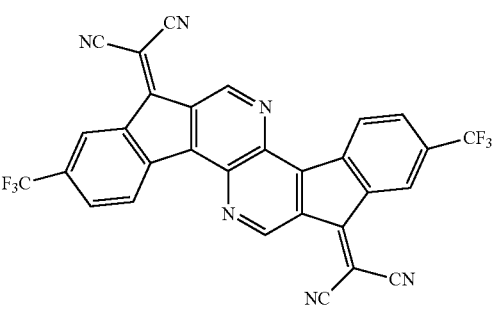
(A-78)
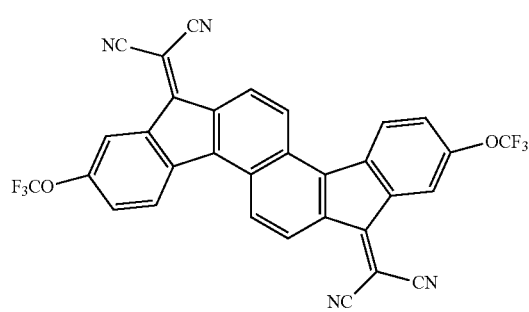
(A-79)
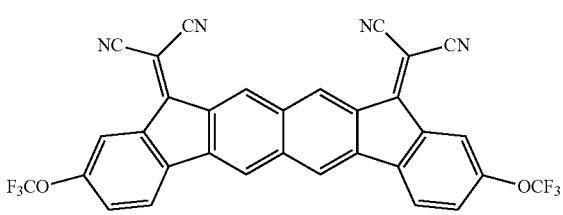
(A-80)
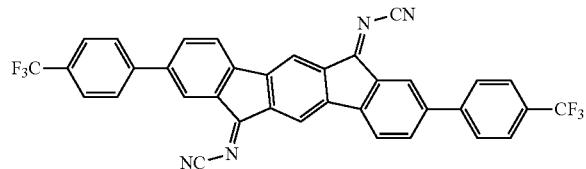
(A-81)
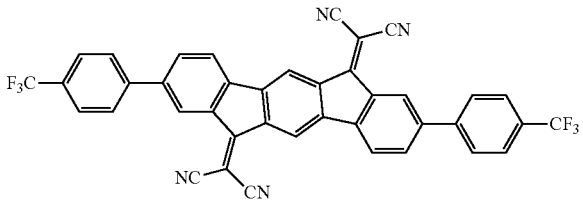
(A-82)
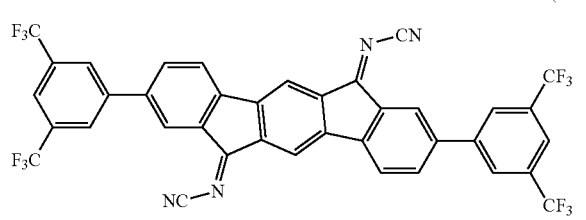
(A-83)
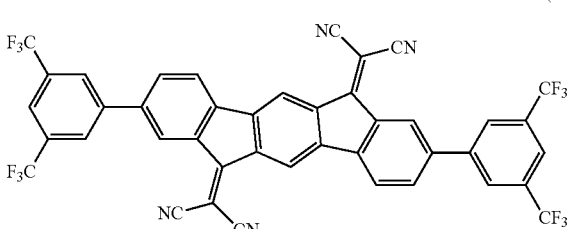
(A-84)
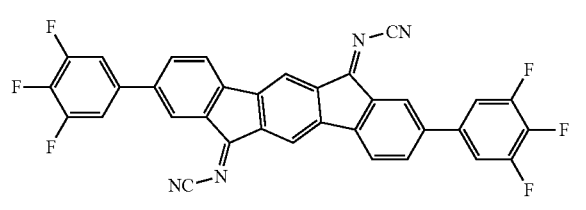
(A-85)
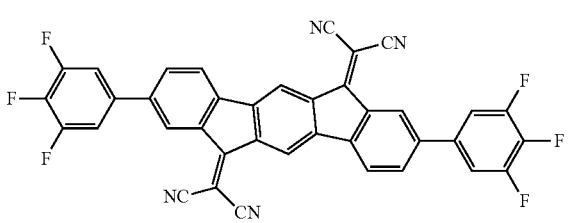
(A-86)

-continued
(A-87)
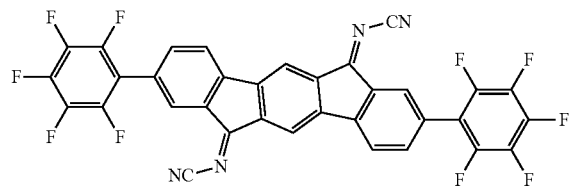
(A-88)
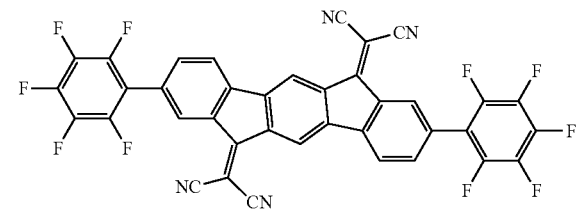
(A-89)
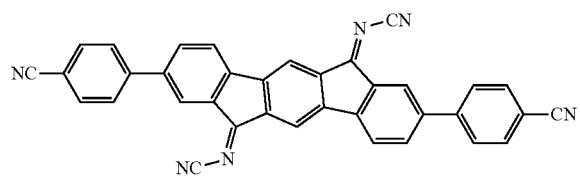
(A-90)
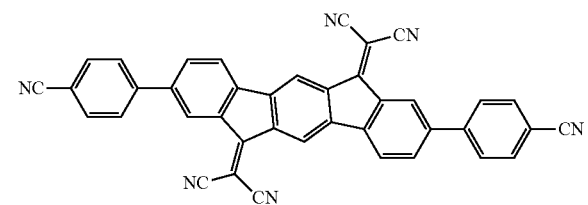
(A-91)
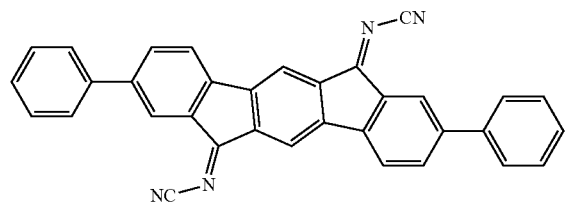
(A-92)
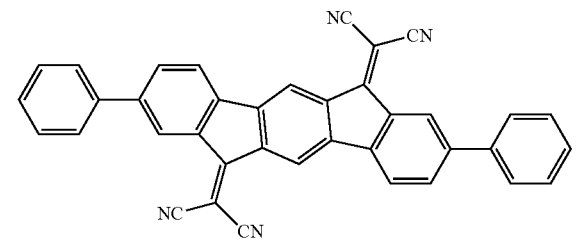
(A-93)
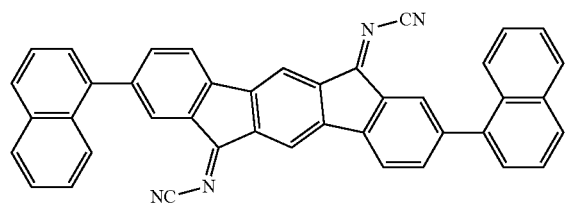
(A-94)
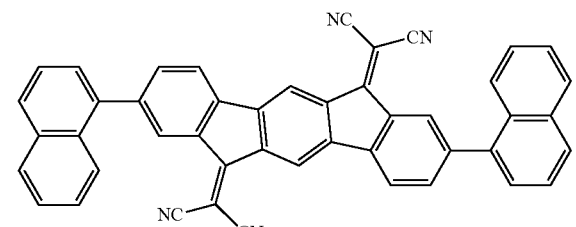
(A-95)
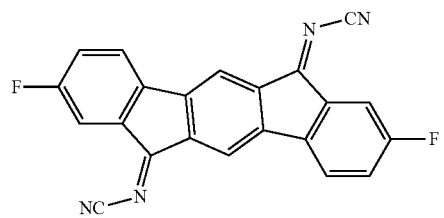
(A-96)
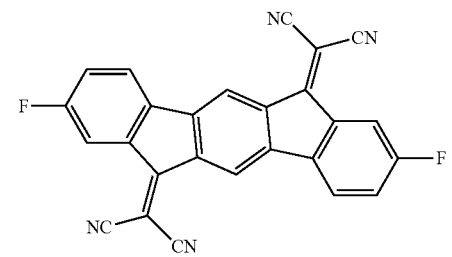
(A-97)
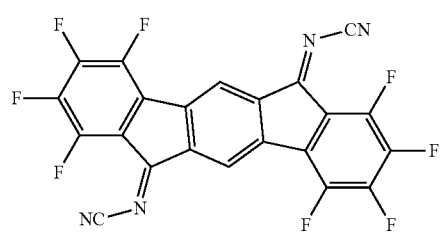
(A-98)
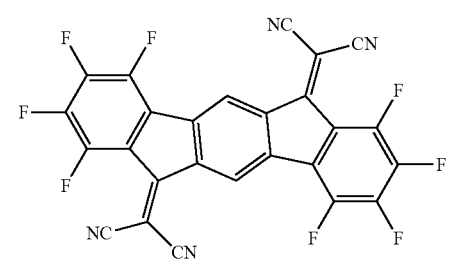

-continued
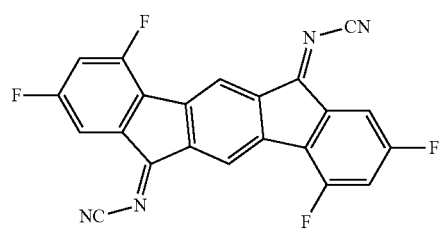 (A-99)
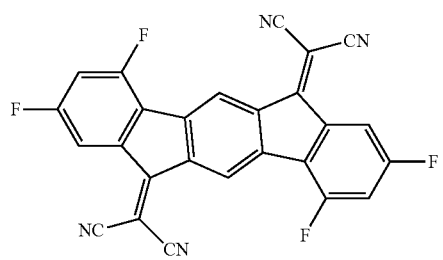 (A-100)
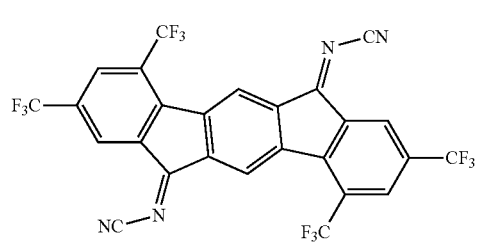 (A-101)
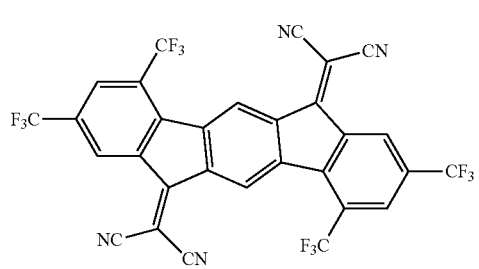 (A-102)
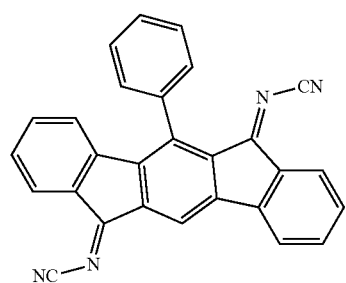 (A-103)
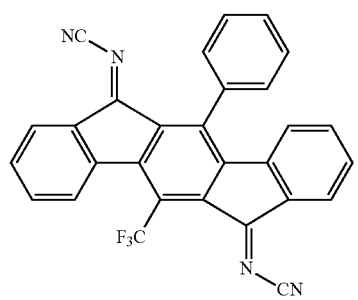 (A-104)
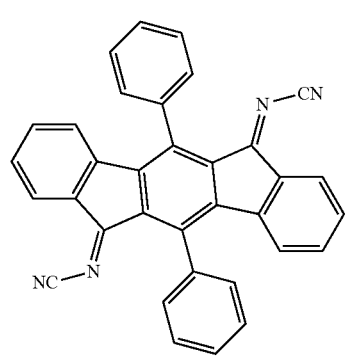 (A-105)
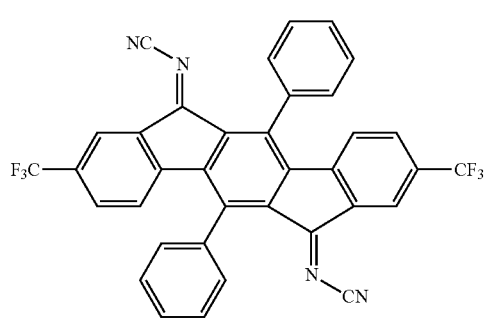 (A-106)
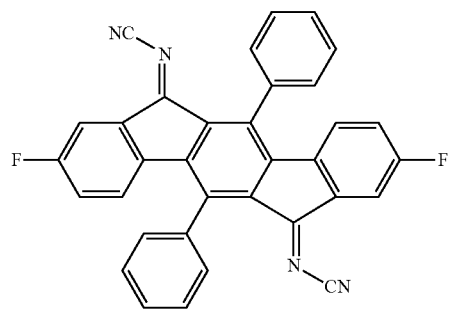 (A-107)
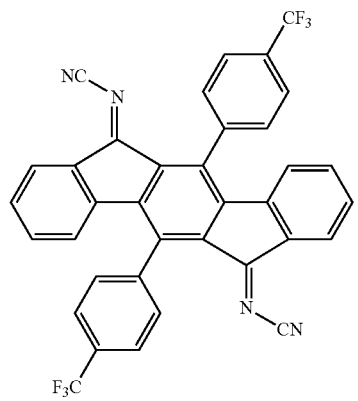 (A-108)

-continued
(A-109)
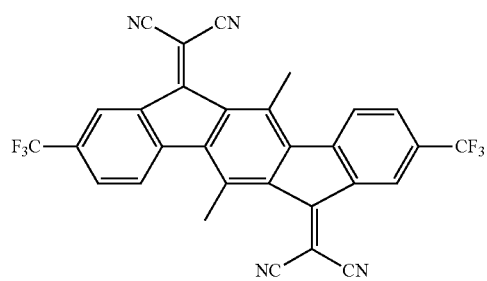
(A-110)
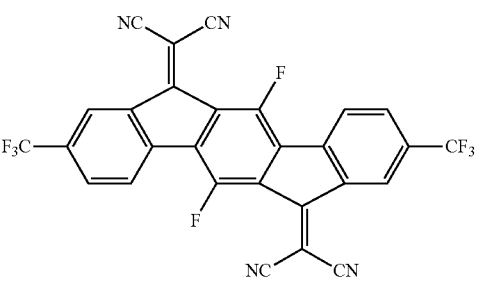
(A-111)
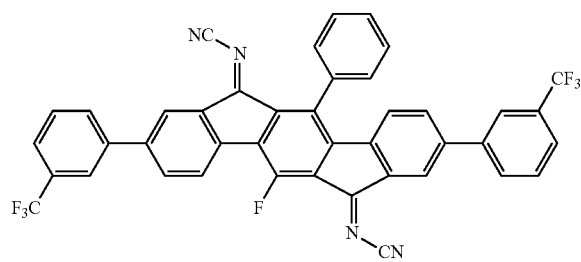
(A-112)
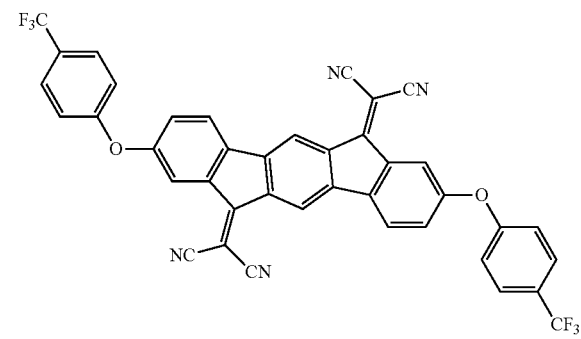
(A-113)
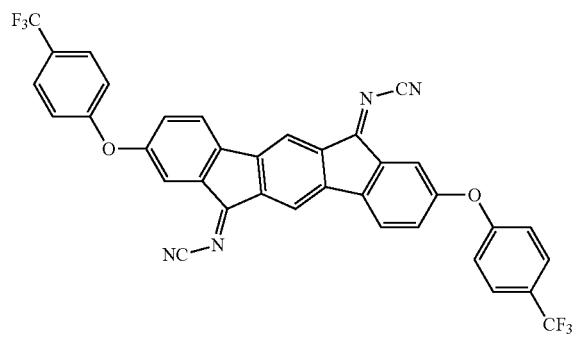
(A-114)
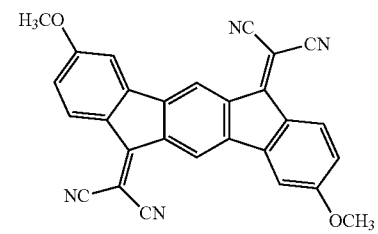
(A-115)
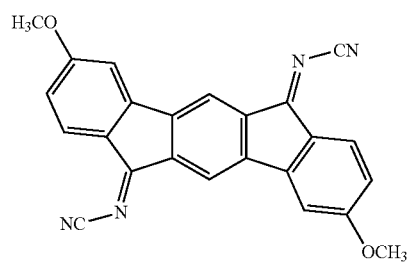
(A-116)
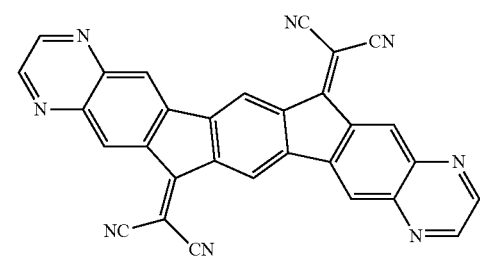
(A-117)
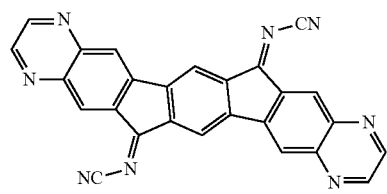
(A-118)
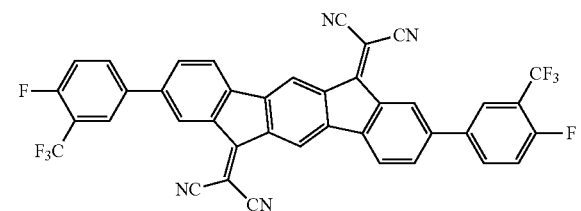

-continued
(A-119)
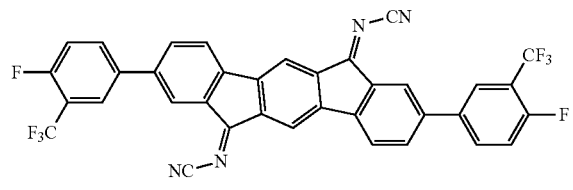
(A-120)
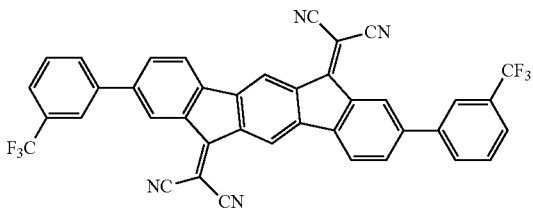
(A-121)
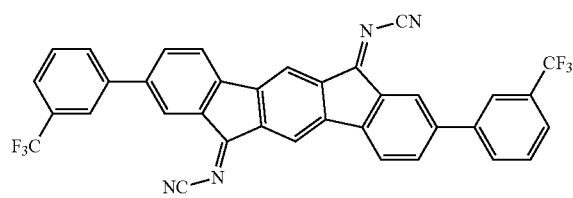
(A-122)
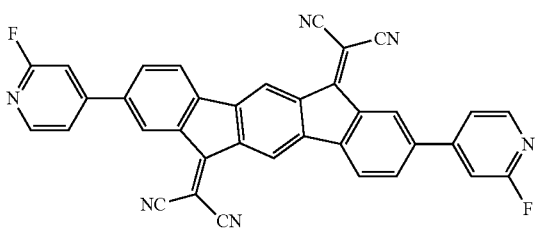
(A-123)
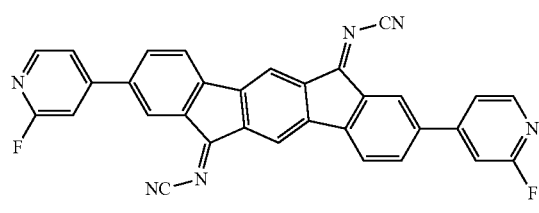
(A-124)
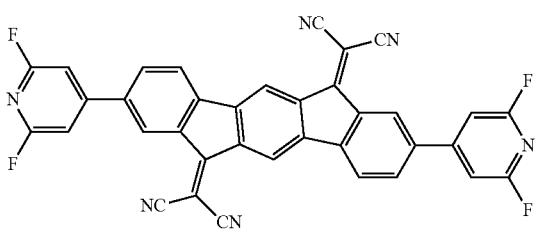
(A-125)
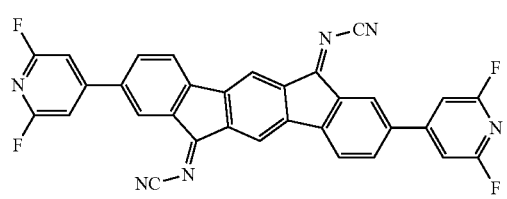
(A-126)
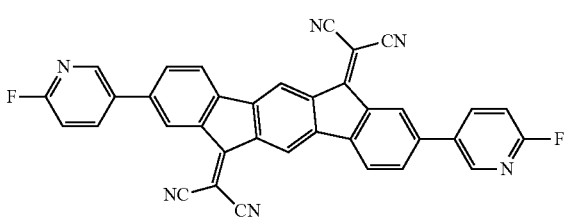
(A-127)
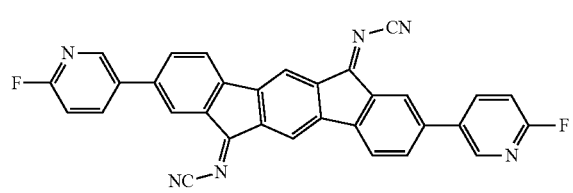
(A-128)
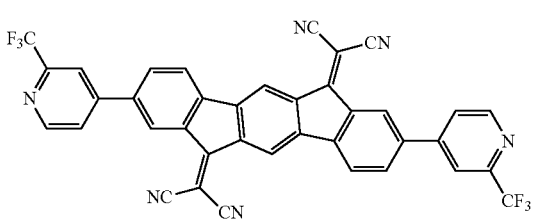
(A-129)
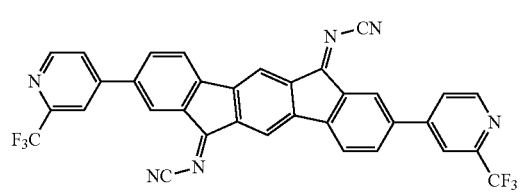
(A-130)
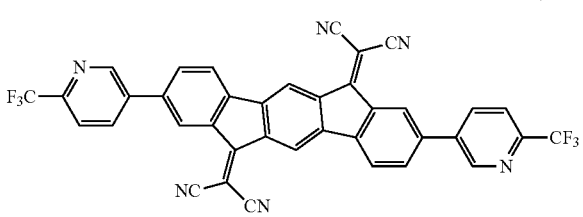

-continued
(A-131)
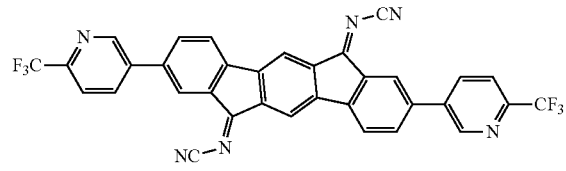
(A-132)
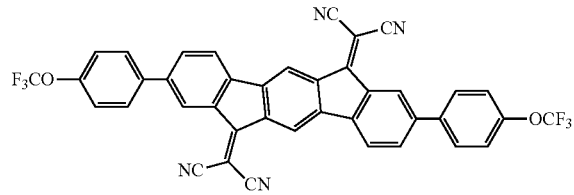
(A-133)
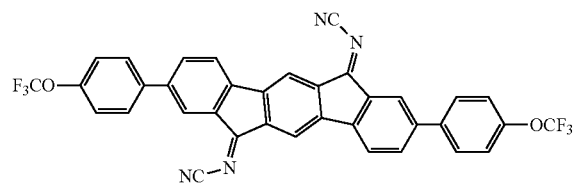
(A-134)
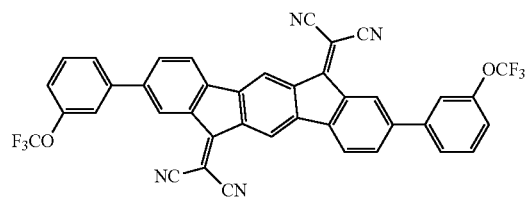
(A-135)
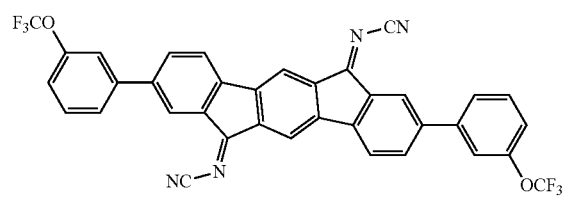
(A-136)
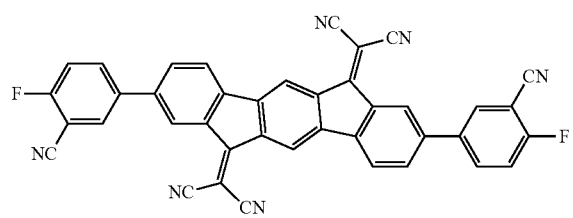
(A-137)
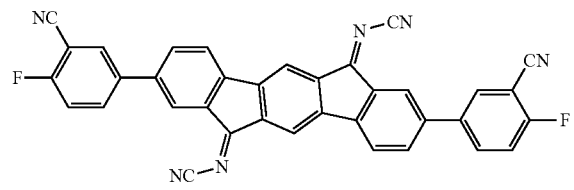
(A-138)
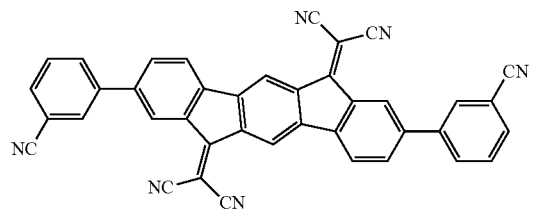
(A-139)
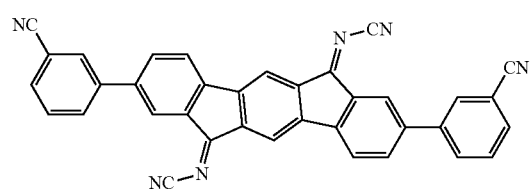
(A-140)
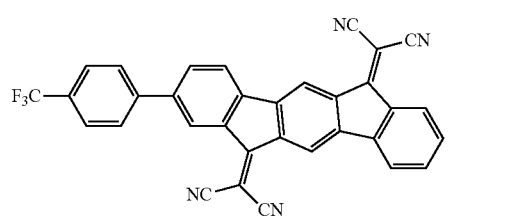
(A-141)
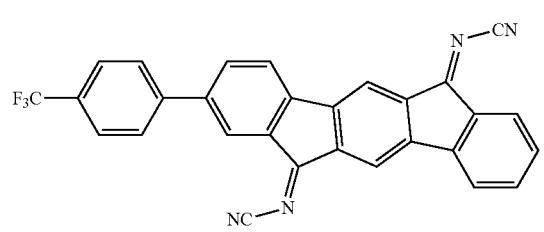
(A-142)
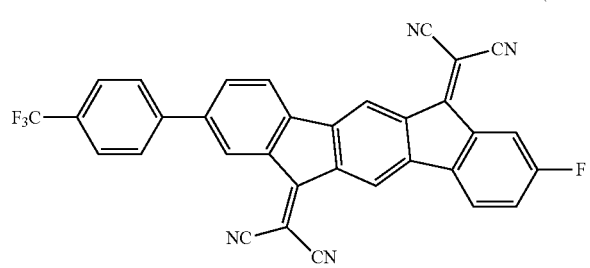

-continued
(A-143)
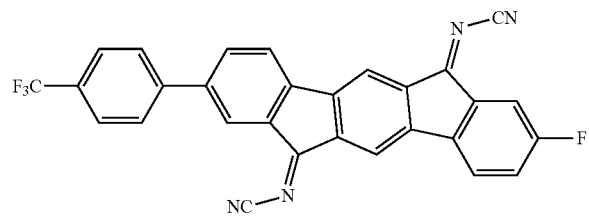
(A-144)
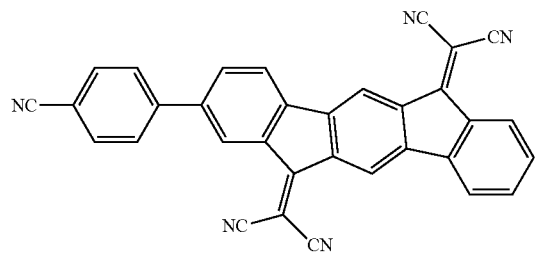
(A-145)
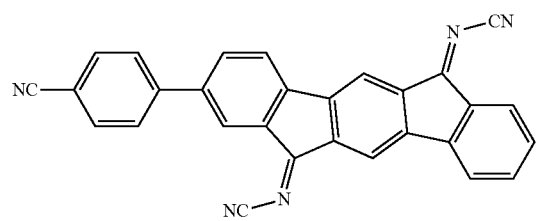
(A-146)
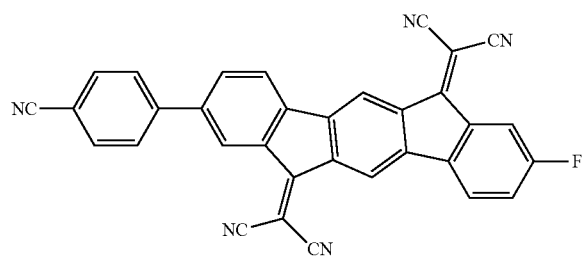
(A-147)
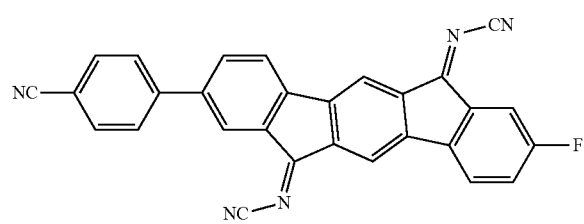
(A-148)
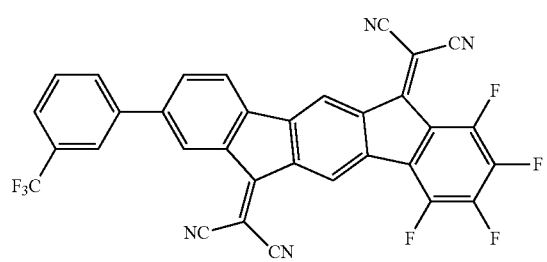
(A-149)
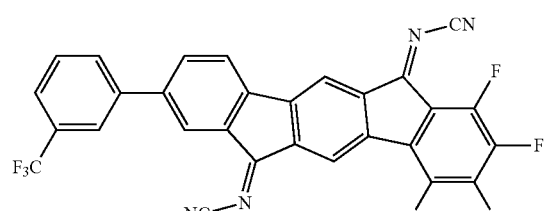
(A-150)
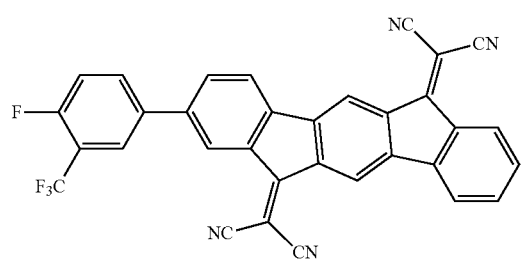
(A-151)
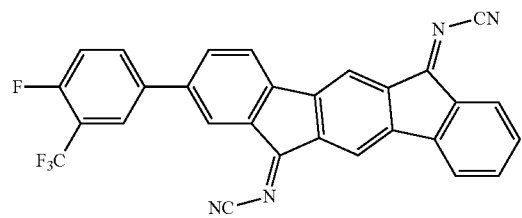
(A-152)
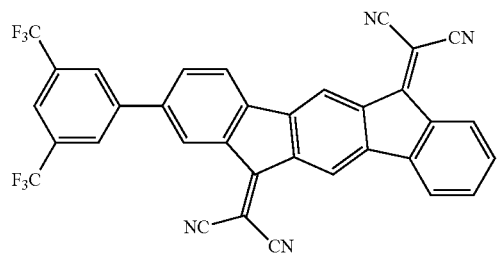
(A-153)
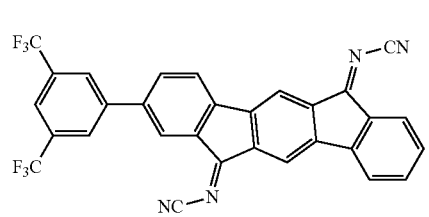
(A-154)
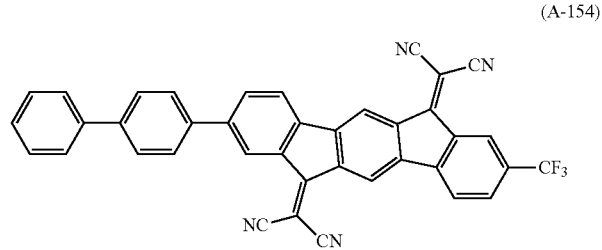

-continued
(A-155)
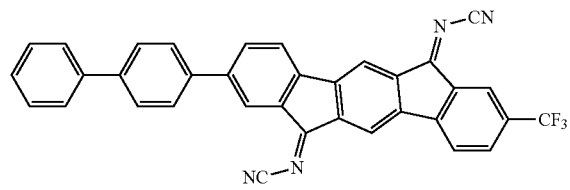
(A-156)
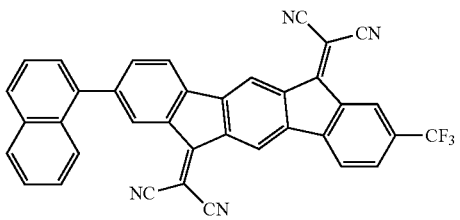
(A-157)
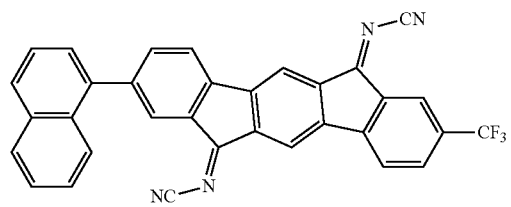
(A-158)
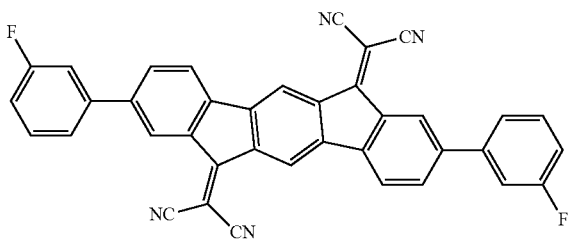
(A-159)
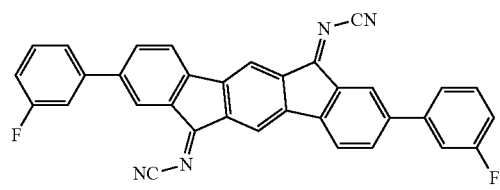
(A-160)
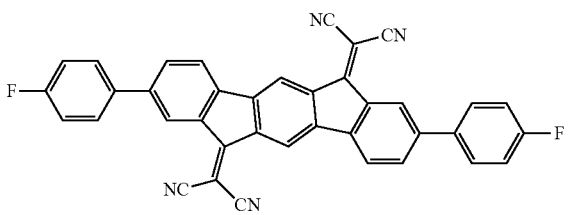
(A-161)
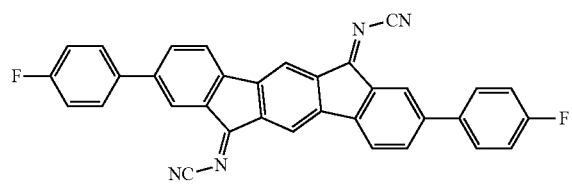
(A-162)
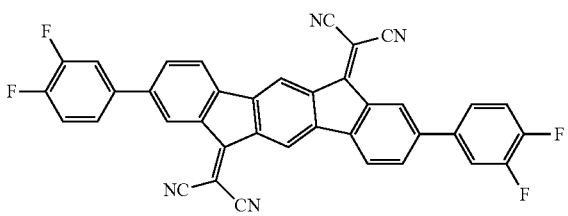
(A-163)
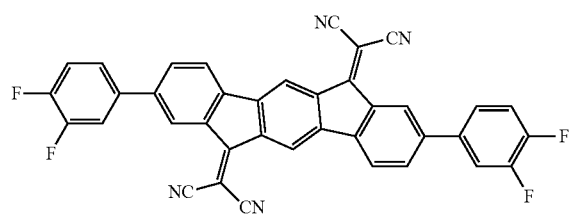
(A-164)
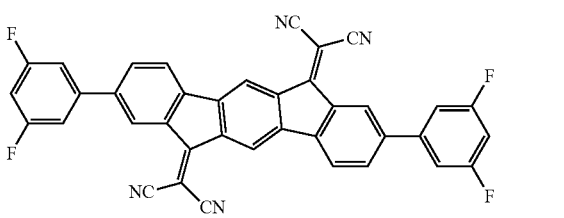
(A-165)
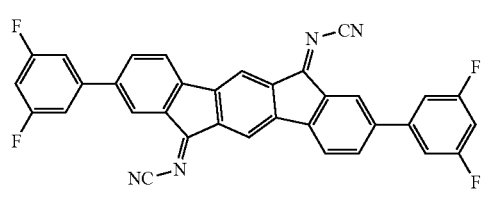
(A-166)
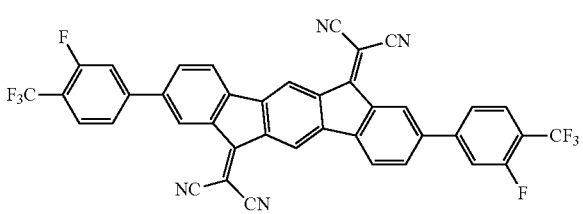

-continued
(A-167)
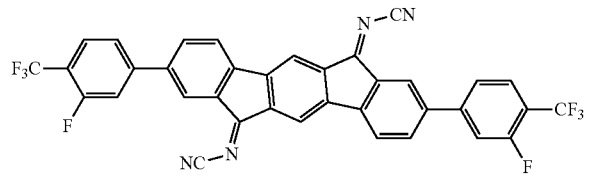
(A-168)
(A-169)
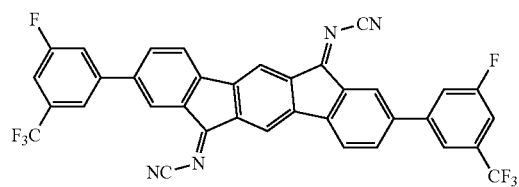
(A-171)
(A-172)
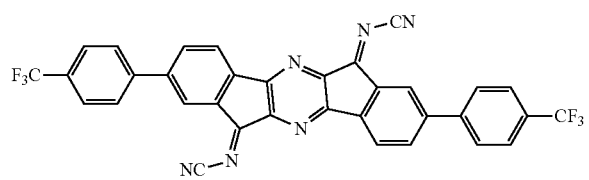
(A-173)
(A-174)
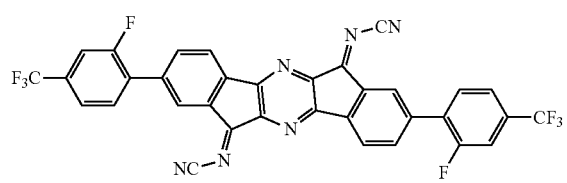
(A-175)
(A-176)
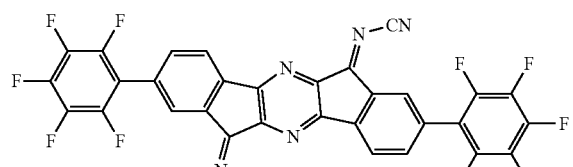
(A-177)
(A-178)
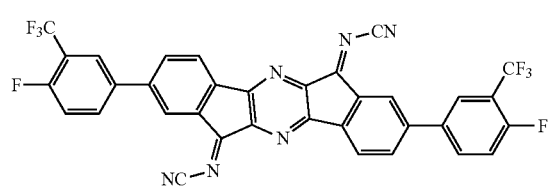
(A-179)
(A-180)
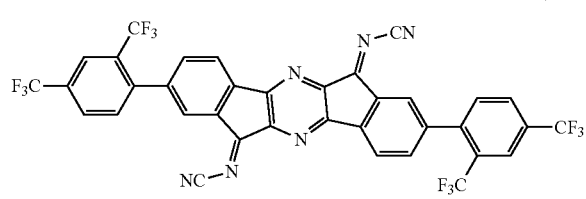
(A-181)
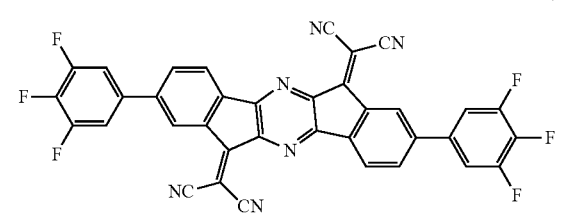

-continued
(A-182)
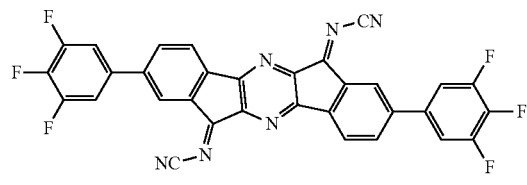
(A-183)
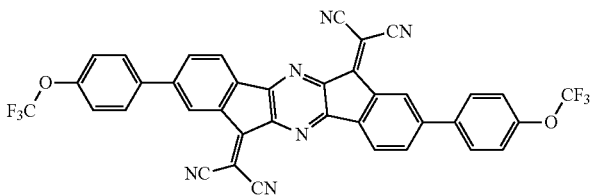
(A-184)
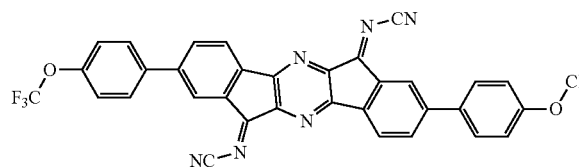
(A-185)
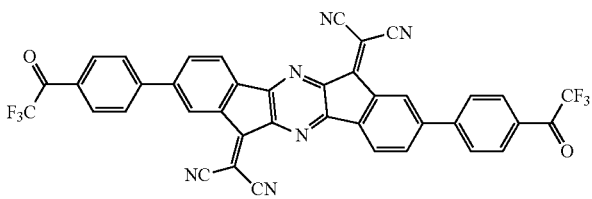
(A-186)
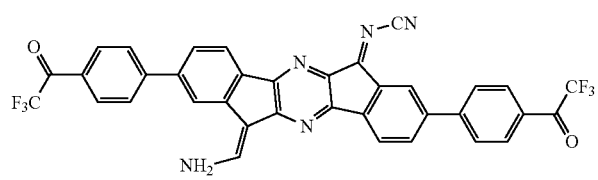
(A-187)
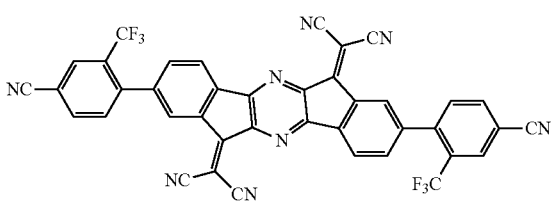
(A-188)
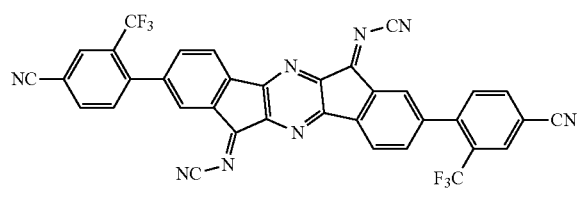
(A-189)
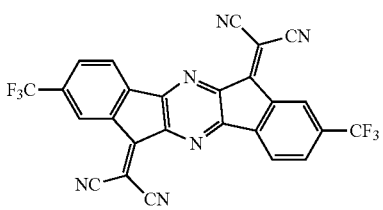
(A-190)
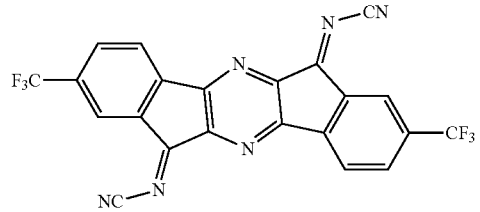
(A-191)
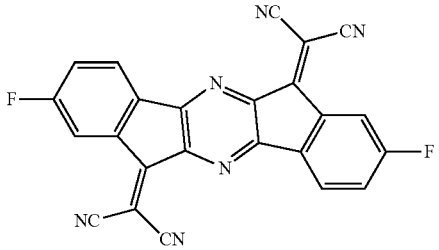
(A-192)
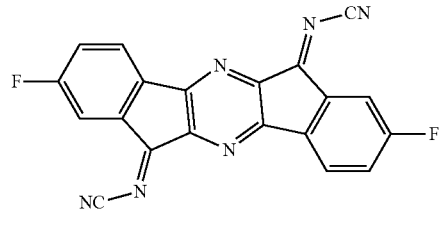
(A-193)
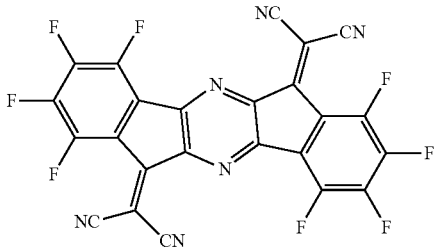

-continued
(A-194)
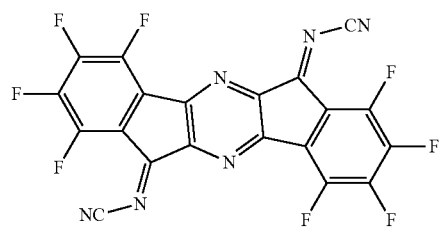
(A-195)
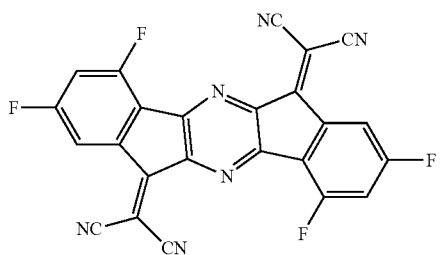
(A-196)
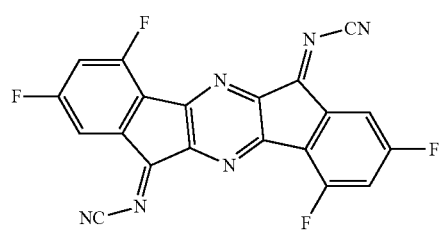
(A-197)
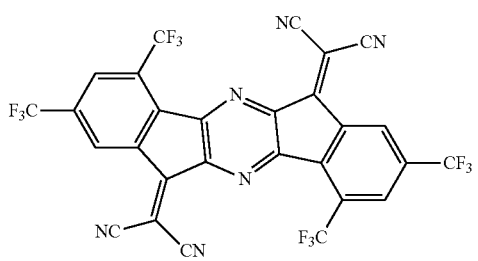
(A-198)
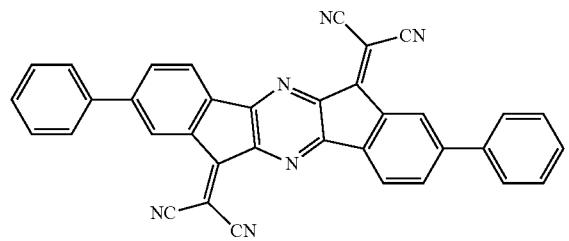
(A-199)
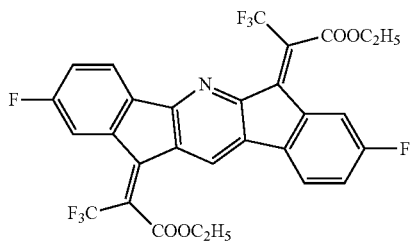
(A-200)
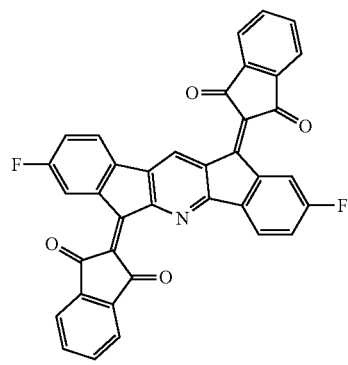
(A-201)
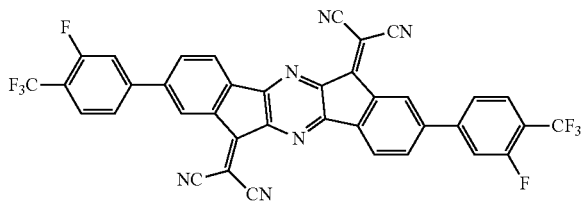
(A-202)
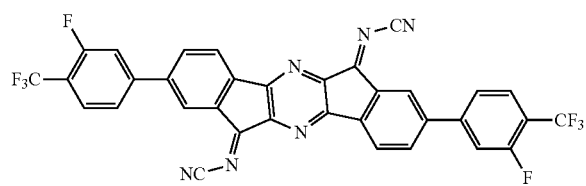
(A-203)
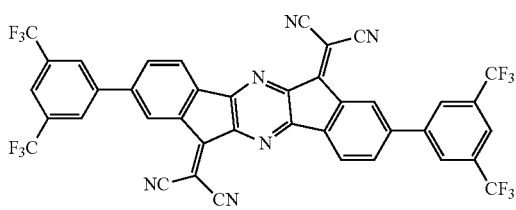
(A-204)
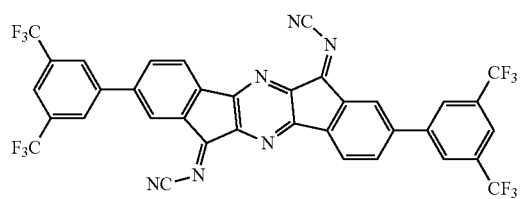
(A-205)
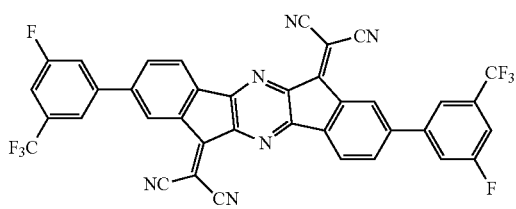

-continued
(A-206)
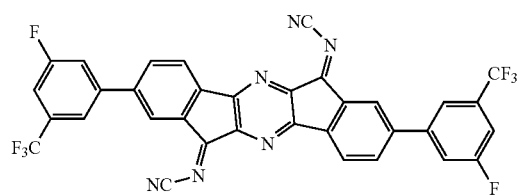
(A-207)
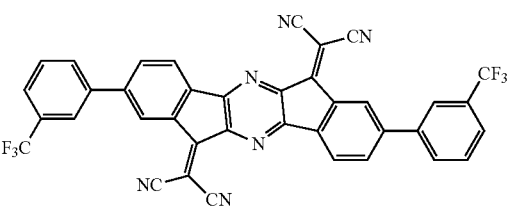
(A-208)
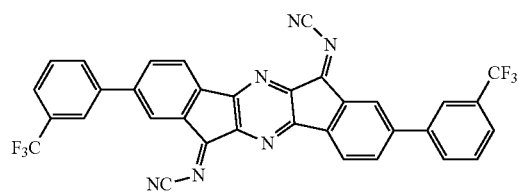
(A-209)
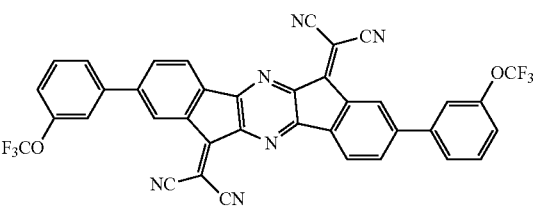
(A-210)
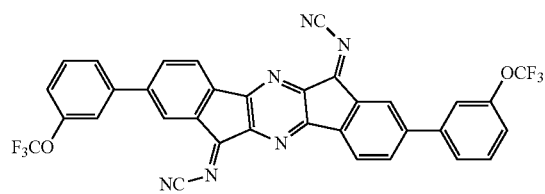
(A-211)
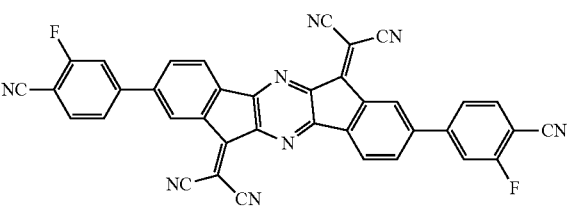
(A-212)
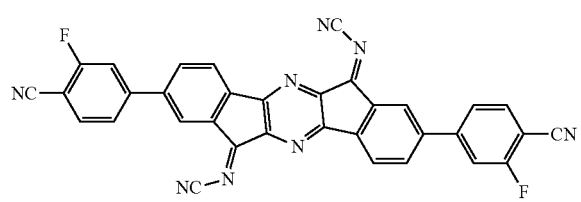
(A-213)
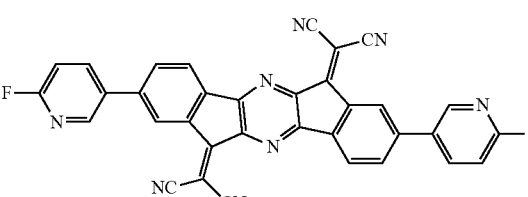
(A-214)
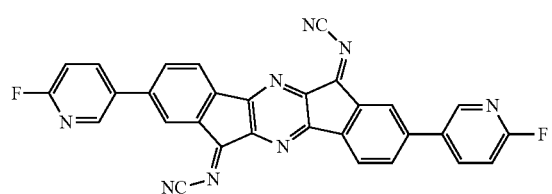
(A-215)
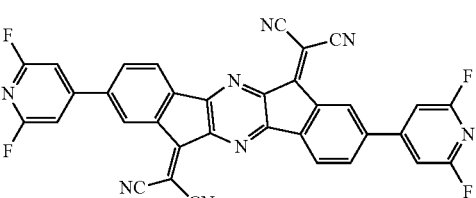
(A-216)
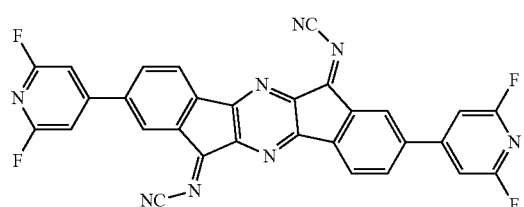
(A-217)
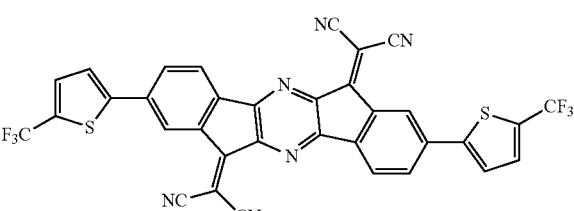
(A-218)
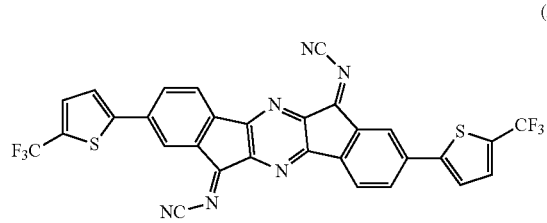
(A-219)
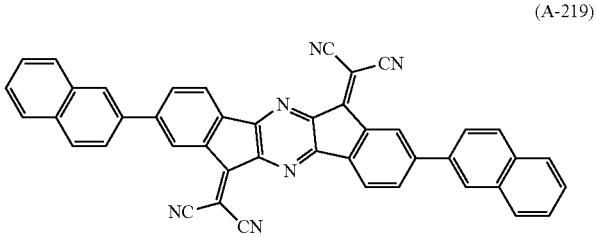

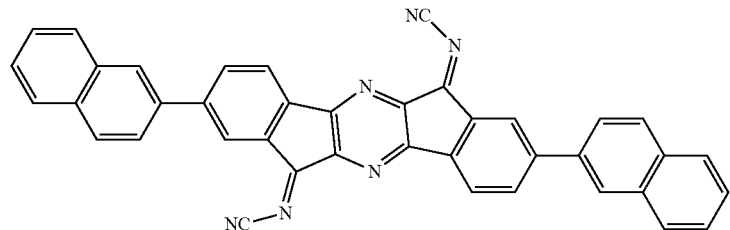
(A-220)
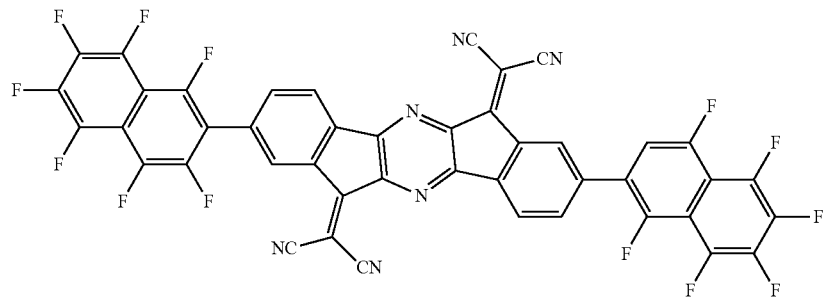
(A-221)
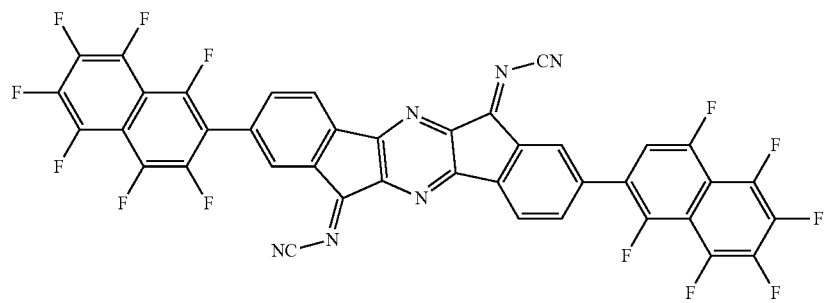
(A-222)
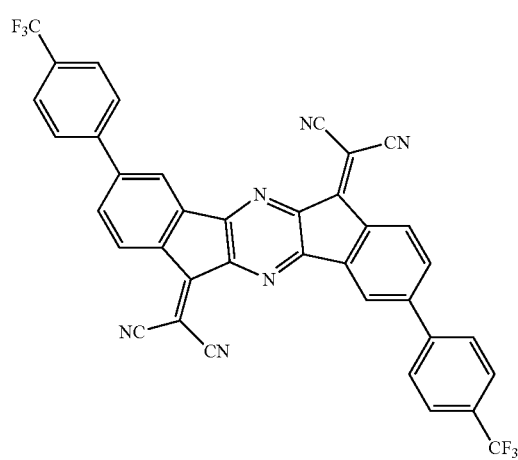
(A-223)
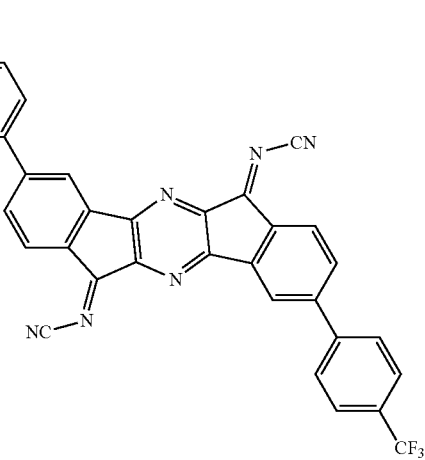
(A-224)

-continued
(A-225)
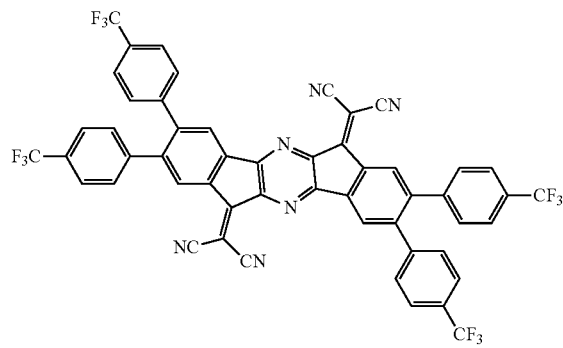
(A-226)
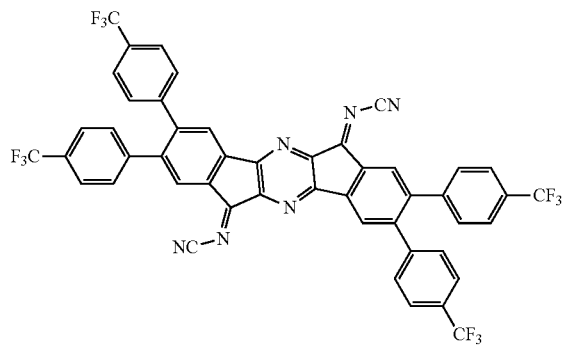
(A-227)
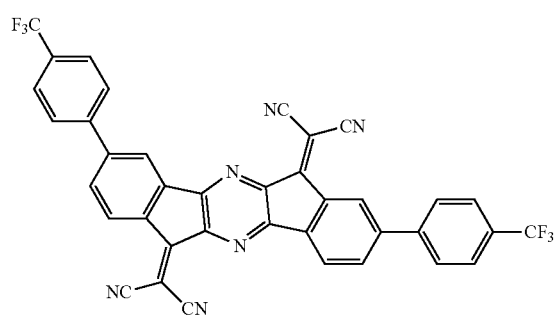
(A-228)
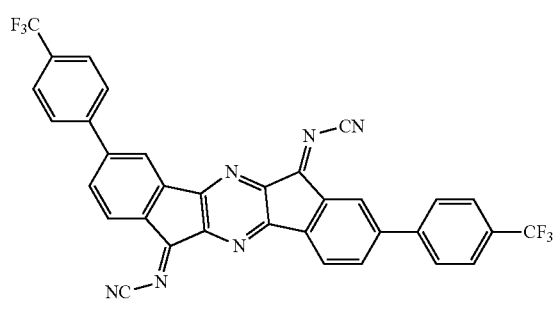
(A-229)
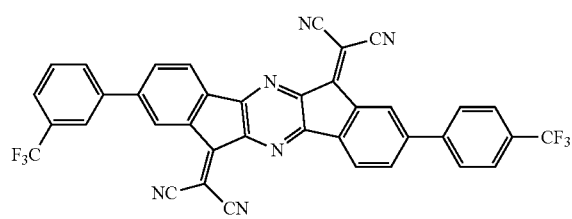
(A-230)
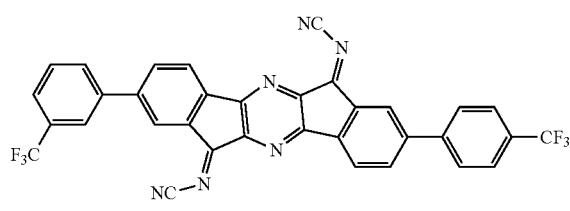
(A-231)
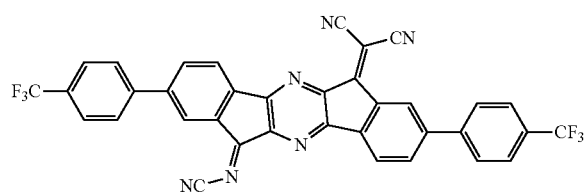
(A-232)
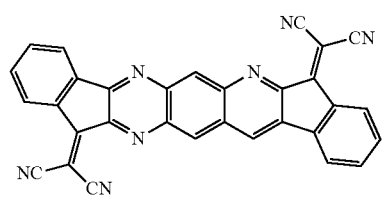
(A-233)
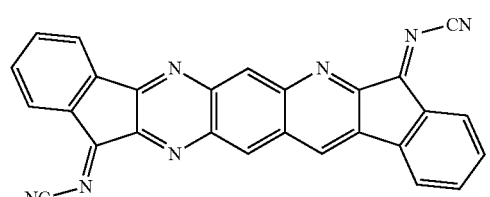
(A-234)
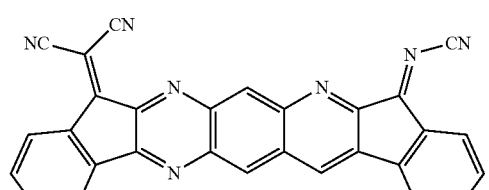
(A-235)
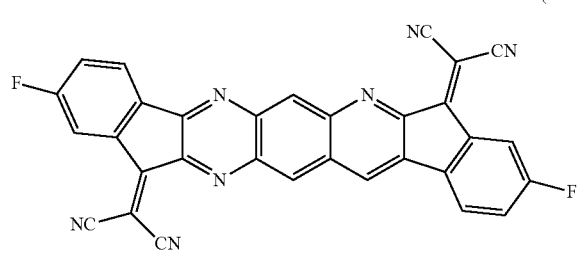
(A-236)
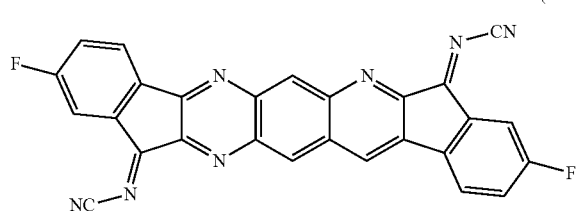

-continued
(A-237)
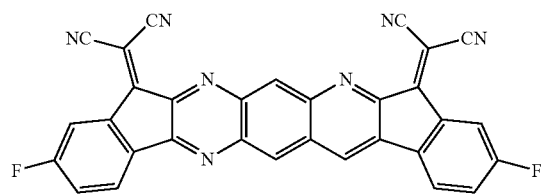
(A-238)
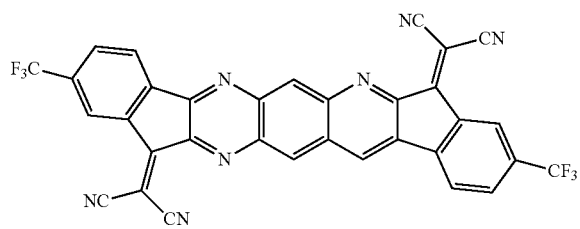
(A-239)
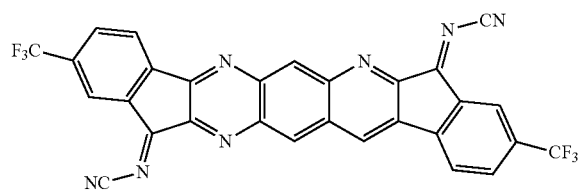
(A-240)
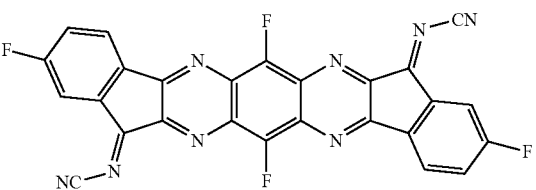
(A-241)
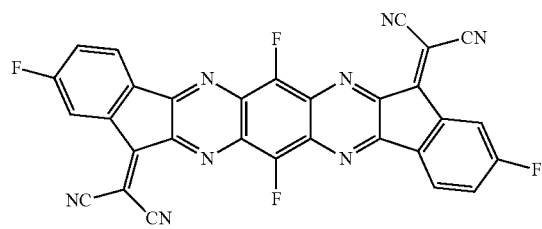
(A-242)
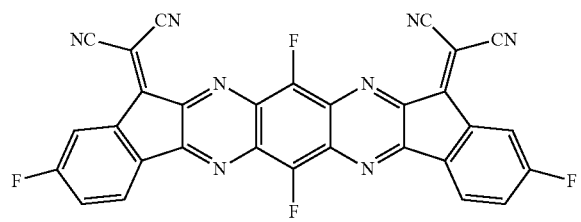
(A-243)
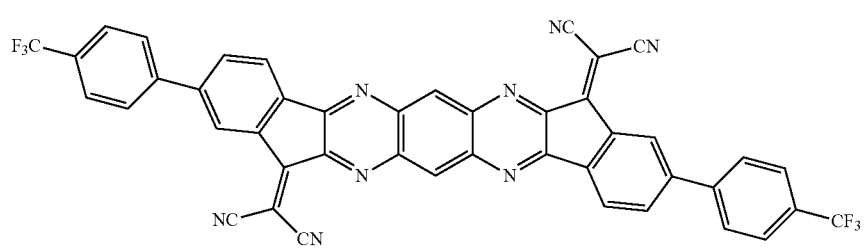
(A-244)
(A-245)
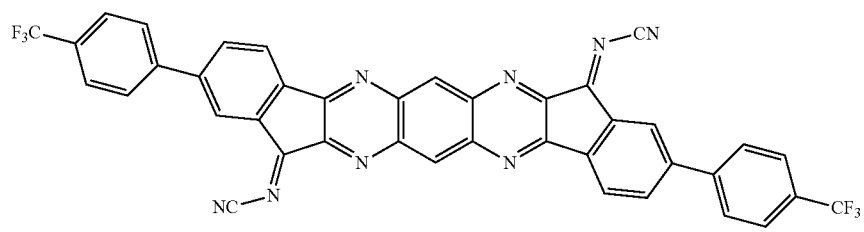

-continued

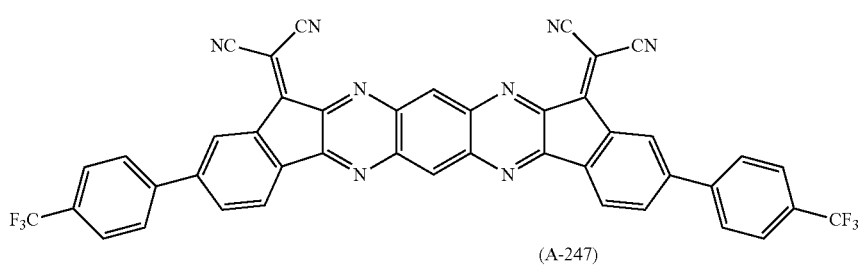

(A-246)

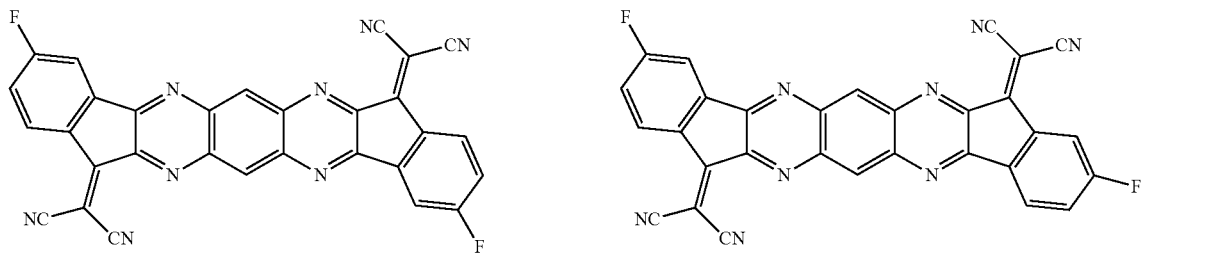

(A-247)　　(A-248)

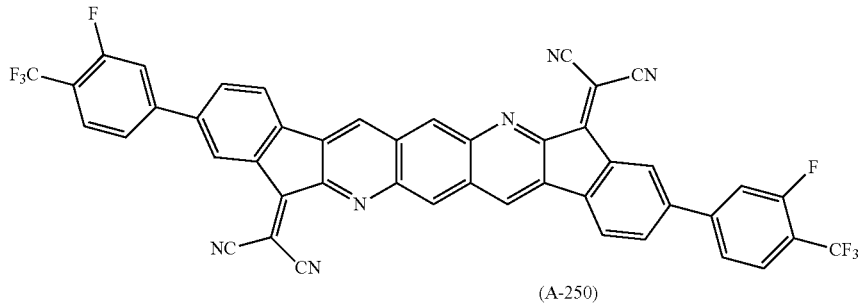

(A-249)

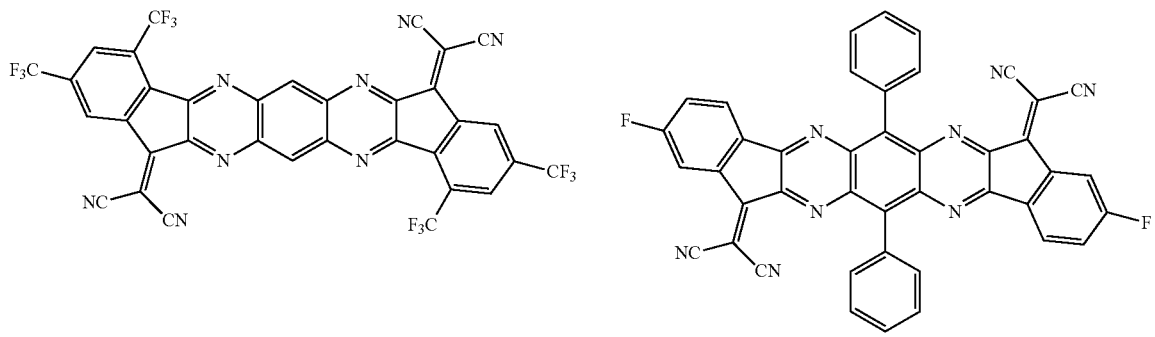

(A-250)　　(A-251)

As for the synthesis of the compound represented by the formula (IV), reference can be made to WO2010/064655 and WO2009/011327.

The acceptor-containing layer may be a layer comprising only the compound represented by the formula (IV) or may be a layer comprising a mixture of this compound with other materials. In the invention, it is preferred that the acceptor-containing layer be a layer that comprises the compound represented by the formula (IV) and at least one hole-transporting material. As the hole-transporting material, a material used in a hole-transporting layer or the like can be used. Among them, an aromatic tertiary amine compound is preferable.

The content of the compound represented by the formula (IV) in the acceptor-containing layer is preferably 0.1 wt % to 100 wt %, with 10 wt % to 70 wt % being particularly preferable.

The film thickness of the acceptor-containing layer is preferably 1 nm to 50 nm, with 5 nm to 20 nm being particularly preferable.

The organic EL device according to one aspect of the invention can be fabricated by a known method. Specifically, the anode or the cathode can be formed by a method such as deposition and sputtering. Each of the organic thin film layers such as the emitting layer can be formed by the vacuum deposition method, the spin coating method, the casting method, the LB method or the like.

Hereinabove, the morphology of the organic EL device according to one aspect of the invention was explained with reference to the organic EL device 1 shown in FIG. 1. The invention is, however, not limited to the morphology of the organic EL device 1. The constitution of the organic EL device according to one aspect of the invention is not restricted to the above-mentioned embodiment, and other known configurations can be used. For example, the organic EL device of the invention may be a stacked multi-photon emission (MPE) device in which two or more emitting units are disposed between the anode and the light-transmissive electrode and a charge-generating layer is disposed between emitting units.

Figure 2:
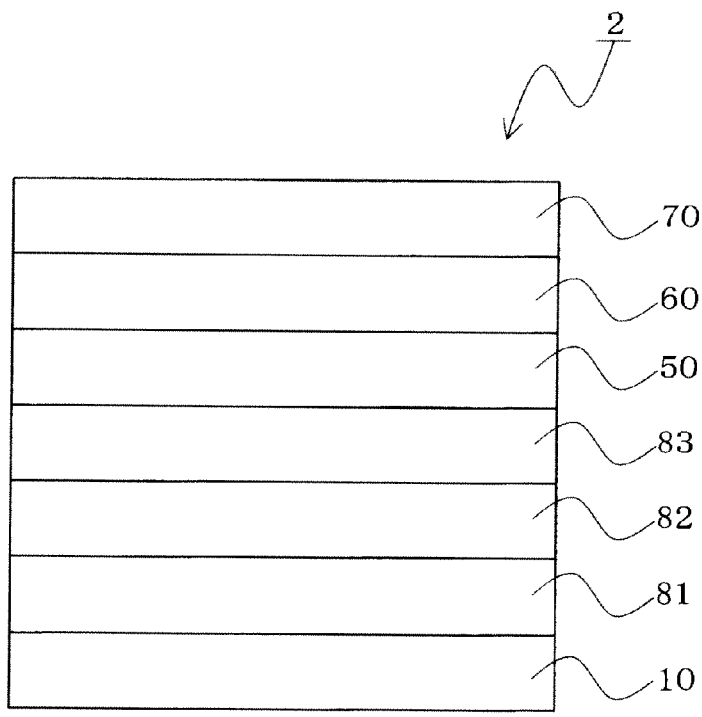
FIG. 2 is a view showing a layer configuration of another embodiment of the organic EL device according to one aspect of the invention.

FIG. 2 is a schematic cross-sectional view of another embodiment of the organic EL device according to one aspect of the invention.

In the organic EL device 2 of this embodiment, on a substrate 10, the anode 20, a first emitting unit 81, a charge-generating layer 82, a second emitting unit 83, a donor-containing layer 50, an acceptor-containing layer 60 and a light-transmissive electrode 70 in this sequence.

The two emitting units respectively have a single-layer structure or a stacked layer structure that at least includes an emitting layer.

For example, it is preferred that the emitting unit have a multi-layer film structure in which a hole-transporting layer, an emitting layer and an electron-transporting layer are stacked from the side of the anode.

As for the constituent elements of an MPE device, such as a charge-generating layer, reference can be made to JP-A-H11-329748, JP-A-2006-173550 or the like.

The organic EL device 2 has the same configuration as that of the organic EL device 1 shown in FIG. 1, except that two emitting units were formed. In other words, the organic EL device 1 has a device configuration in which one emitting unit having the hole-injecting layer 20, the hole-transporting layer 30 and the emitting layer 40 is provided.

In this embodiment, for example, by changing the emission color of each emitting unit, that is, by changing the material of the emitting layer, a white-emitting organic EL device can be obtained.

In each of the emitting units of this embodiment, as a layer formed between the emitting layer and the charge-generating layer, the donor-containing layer and the acceptor-containing layer mentioned above may be used. For example, in the organic EL device 2, the first emitting unit 81 may have a configuration in which the hole-transporting layer, the emitting layer, the donor-containing layer and the acceptor-containing layer are stacked from the anode side.

EXAMPLES

Examples 1 to 15

On a glass substrate having a dimension of 30 mm×30 mm, ITO was formed in a thickness of 240 nm as an anode. Subsequently, by deposition of SiO$_2$, a cell for an organic EL device in which other parts than emitting regions of 2 mm×2 mm were masked by an insulating film was fabricated.

On the anode, as a hole-injecting layer, hexanitrileazatriphenylene ((HAT) represented by the following formula) was formed in a thickness of 10 nm.

On the hole-injecting layer, a hole-transporting layer, a blue-emitting layer and an electron-transporting layer were formed in this sequence.

Specifically, as the hole-transporting layer, the compound represented by the following formula (α-NPD) was formed into a 90 nm-thick film by the vacuum vapor deposition method (deposition speed: 0.2 to 0.4 nm/sec).

Subsequently, on the hole-transporting layer, the blue-emitting layer was formed. As the host for the emitting layer, the compound represented by the following formula (1) was used, and as the dopant for the emitting layer, the compound represented by the following formula (2) was used. Vacuum vapor deposition was conducted such that the amount of the dopant added became 5% in terms of film thickness ratio, whereby an emitting layer having a film thickness of 30 nm was formed.

Then, on the blue-emitting layer, as the electron-transporting layer, (Alq3) of the following formula was formed into a 30 nm-thick film.

Subsequently, on the electron-transporting layer, a donor-containing layer and an acceptor-containing layer were formed in this sequence by using the compounds shown in Table 1. The donor-containing layer is a mixture layer of the compound shown in Table 1 and Li (the "%" in Table 1 is a value relative to the film thickness ratio).

On the acceptor-containing layer, the cathode shown in Table 1 (ITO or IZO: film thickness 20 nm) was formed by sputtering, whereby an organic EL device was fabricated.

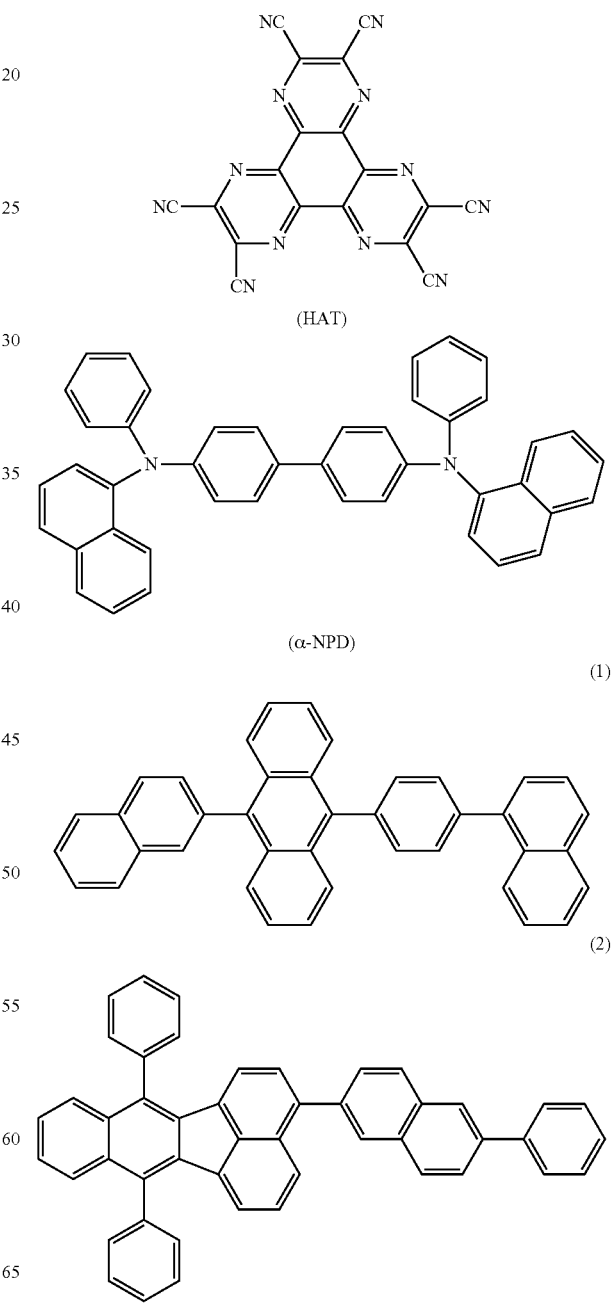

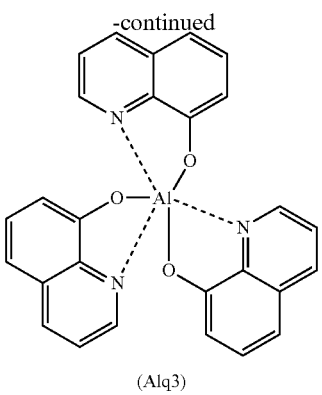

(Alq3)

For the organic EL devices fabricated, the voltage (V), the luminous efficiency (cd/m$^2$) at 10 mA cm$^{-2}$, and the relative luminance value after 300-hour driving at 50 mA/cm$^{-2}$ were measured.

The results are shown in Table 1.

electron-injecting layer. Then, a cathode (ITO: 200 nm) was formed on the LiF film, whereby an organic EL device was fabricated. Evaluation was conducted in the same manner as in the Example, and the results are shown in Table 1.

Comparative Example 3

An organic EL device was fabricated and evaluated in the same manner as in Comparative Example 2, except that the material of the cathode was changed from ITO to an Mg—Ag alloy, and the thickness of the cathode was changed to 10 nm. The results are shown in Table 1.

Comparative Example 4

An organic EL device was fabricated and evaluated in the same manner as in Comparative Example 2, except that a stacked body of a 10 nm-film of a cupper phthalocyanine complex (CuPc) and a 1 nm-thick Li film was used instead of the LiF layer. The results are shown in Table 1.

TABLE 1

| | Donor-containing layer : Film thickness | Acceptor-containing layer Film thickness | Electron-injecting layer : Film thickness | Cathode : Film thickness | Voltage (V) | Efficiency (cd/A) | Relative luminance value |
|---|---|---|---|---|---|---|---|
| Ex. 1 | (B-1) + Li(2%) 20 nm | (A-55) 20 nm | — | ITO 200 nm | 3.2 | 9.5 | 97% |
| Ex. 2 | (B-1) + Li(2%) 20 nm | (A-57) 20 nm | — | ITO 200 nm | 3.2 | 9.4 | 96% |
| Ex. 3 | (B-1) + Li(2%) 20 nm | (A-84) 20 nm | — | ITO 200 nm | 3.1 | 9.5 | 97% |
| Ex. 4 | (B-1) + Li(2%) 20 nm | (A-177) 20 nm | — | ITO 200 nm | 3.2 | 9.4 | 96% |
| Ex. 5 | (B-1) + Li(2%) 20 nm | HAT 10 nm | — | ITO 200 nm | 3.3 | 9.2 | 95% |
| Ex. 6 | (B-2) + Li(2%) 20 nm | (A-55) 20 nm | — | ITO 200 nm | 3.2 | 9.4 | 97% |
| Ex. 7 | (B-2) + Li(2%) 20 nm | (A-57) 20 nm | — | ITO 200 nm | 3.1 | 9.3 | 96% |
| Ex. 8 | (B-2) + Li(2%) 20 nm | (A-84) 20 nm | — | ITO 200 nm | 3.2 | 9.4 | 97% |
| Ex. 9 | (B-2) + Li(2%) 20 nm | (A-177) 20 nm | — | ITO 200 nm | 3.3 | 9.2 | 96% |
| Ex. 10 | (B-2) + Li(2%) 20 nm | HAT 10 nm | — | ITO 200 nm | 3,2 | 9.4 | 95% |
| Ex. 11 | (B-75) + Li(2%) 20 nm | (A-55) 20 nm | — | ITO 200 nm | 3.1 | 9.0 | 92% |
| Ex. 12 | (B-75) + Li(2%) 20 nm | HAT 10 nm | — | ITO 200 nm | 3.4 | 9.3 | 96% |
| Ex. 13 | (B-75) + Li(2%) 20 nm | (A-55) 20 nm | — | ITO 200 nm | 3.1 | 9.0 | 93% |
| Ex. 14 | (B-75) + Li(2%) 20 nm | (A-55) 20 nm | — | IZO 200 nm | 3.4 | 8.9 | 95% |
| Ex. 15 | (B-75) + Ca(10%) 20 nm | (A-55) 20 nm | — | IZO 200 nm | 4.2 | 8.7 | 90% |
| Comp. Ex.1 | Alq3 + Mg(2%) 40 nm | — | — | ITO 200 nm | 9.0 | 1.2 | 42% |
| Comp. Ex.2 | — | — | LiF 1 nm | ITO 200 nm | Not emit | — | — |
| Comp. Ex.3 | — | — | LiF 1 nm | MgAg 10 nm | 3.1 | 5.0 | 89% |
| Comp. Ex.4 | — | — | CuPc10 nm/Li 1 nm | ITO 200 nm | 8.0 | 2.3 | 68% |
| Comp. Ex.5 | Alq3 + Mg(2%) 20 nm/Al 2 nm | MoO$_3$ 10 nm | — | ITO 200 nm | 7.0 | 3.8 | 58% |
| Comp. Ex.6 | Bphen + Li(2%) 20 nm | HAT 20 nm | — | IZO 200 nm | 4.7 | 8.9 | 30% |
| Comp. Ex.7 | (3) + Ca(10%) 20 nm | HAT 20 nm | — | IZO 200 nm | 6.0 | 7.0 | 72% |

Comparative Example 1

Fabrication of an organic EL device was conducted in the same manner as in Example 1 until the electron-transporting layer (Alq3 layer) was formed. Thereafter, as the donor-containing layer, a mixture layer of Alq3 and Mg (Mg: 2%) was formed in a film thickness of 40 nm.

On the donor-containing layer, a cathode (ITO: 200 nm) was formed, whereby an organic EL device was fabricated. Evaluation was conducted in the same manner as in the Example, and the results are shown in Table 1.

Comparative Example 2

Fabrication of an organic EL device was conducted in the same manner as in Example 1 until the electron-transporting layer (Alq3 layer) was formed. Thereafter, without forming the donor-containing layer and the acceptor-containing layer, LiF was formed in a thickness of 1 nm as the Comparative Example 5

Fabrication of an organic EL device was conducted in the same manner as in Example 1 until the electron-transporting layer (Alq3 layer) was formed. Thereafter, a mixture layer of Alq3 and Mg (Mg: 2%) was formed into a film of 20 nm. Then, an Al layer was formed in a thickness of 2 nm. Further, an MoO$_3$ layer was formed thereon in a thickness of 10 nm. Then, a cathode (ITO: 200 nm) was formed on the MoO$_3$ layer, whereby an organic EL device was fabricated. Evaluation was conducted in the same manner as in the Example, and the results are shown in Table 1.

Comparative Example 6

An organic EL device was fabricated in the same manner as in Example 1, except that a mixture layer of the following Bphen and Li (Li: 2%) was used as the donor-containing layer and HAT was used as the acceptor-containing layer, and the material of the cathode was changed to IZO. The results are shown in Table 1.

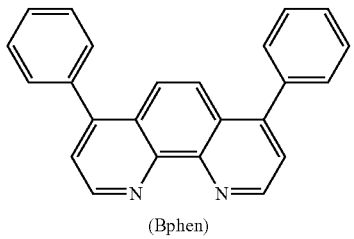 [SMILES: c1ccc(-c2ccnc3c2ccc2c(-c4ccccc4)ccnc23)cc1]

(Bphen)

Comparative Example 7

An organic EL device was fabricated and evaluated in the same manner as in Comparative Example 6, except that a mixture layer of the compound represented by the following formula (3) and Ca (Ca: 10%) was used as the donor-containing layer. The results are shown in Table 1.

(3)

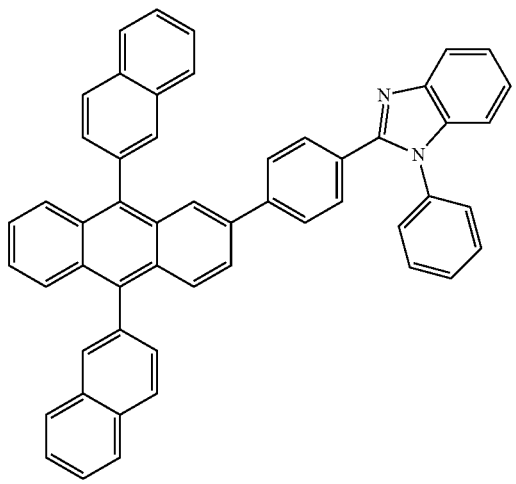

From the results of evaluation, it can be confirmed that, in Examples 1 to 15, a stable device that has a high efficiency, can be driven at a low voltage and suffers only less deterioration can be obtained.

On the other hand, as for Comparative Examples 1, 2 and 4, due to the absence of the donor-containing layer and the acceptor-containing layer according to one aspect of the invention, electron supply shortage and damage at the time of forming a cathode occurred, resulting in an increase in driving voltage, a lowering in efficiency and shortening of the life of the device. In Comparative Example 3, lowering in efficiency of the device occurred by absorption of emission by the MgAg electrode.

In Comparative Example 5, since an Al metal layer was inserted, absorption of emission occurred. As a result, efficiency of the device was lowered, and an increase in driving voltage and shortening in life of the device occurred due to the electron supply shortage by the acceptor-containing layer.

In Comparative Examples 6 and 7, since the compound of the donor-containing layer was unstable, the life of the device was shortened. In addition, due to insufficient electron withdrawal properties, an increase in driving voltage occurred.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and a Japanese application on the basis of which the present application claims Paris convention priority are incorporated herein by reference in its entirety.

The invention claimed is:

1. An organic electroluminescence device comprising:
an anode;
one or more organic thin film layers including an emitting layer;
a donor-containing layer;
an acceptor-containing layer that transfers electrons into the donor-containing layer; and
a light-transmissive cathode in this order,
wherein the donor-containing layer comprises a compound represented by the following formulas (I) or (II):

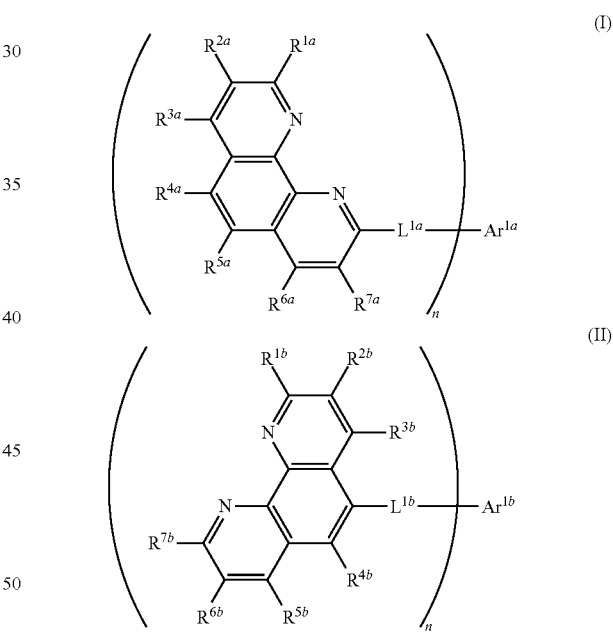

wherein in the formulas,
$R^{1a}$ to $R^{7a}$ and $R^{1b}$ to $R^{7b}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 ring carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group that is substituted with a substituted or unsubstituted aryl group including 6 to 50 ring carbon atoms, a halogen atom, a cyano group, a nitro group, a hydroxyl group or a carboxyl group, and adjacent groups of $R^{1a}$ to $R^{7a}$ or adjacent groups of $R^{1b}$ to $R^{7b}$ may be bonded each other to form a ring;

$L^{1a}$ and $L^{1b}$ are independently a single bond or a linkage group;

$Ar^{1a}$ and $Ar^{1b}$ are independently a substituted or unsubstituted aromatic group including 6 to 60 carbon atoms; and n is an integer of 1 to 4, and when n is 2 or more, the groups having a phenanthroline skeleton in parentheses may be the same or different from each other.

2. The organic electroluminescence device according to claim 1, wherein the compound represented by the formula (I) or (II) is a compound represented by the following formula (I-a), (I-b), (II-a) or (II-b):

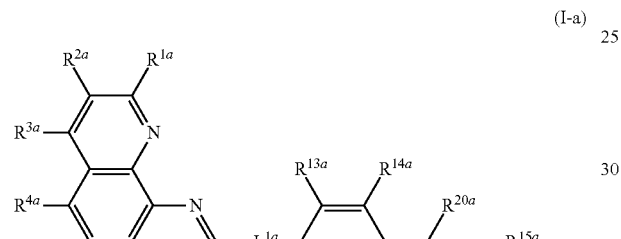

(I-a)

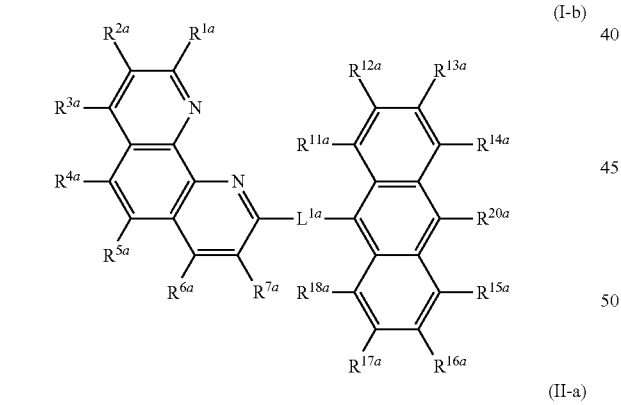

(I-b)

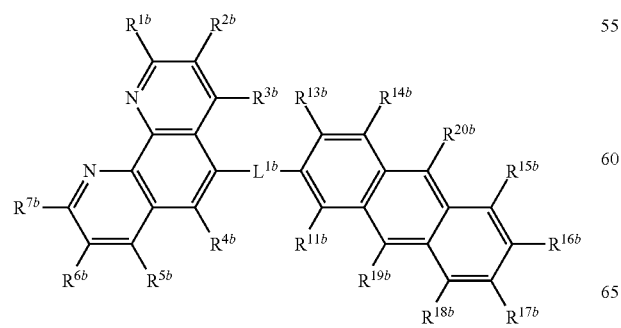

(II-a)

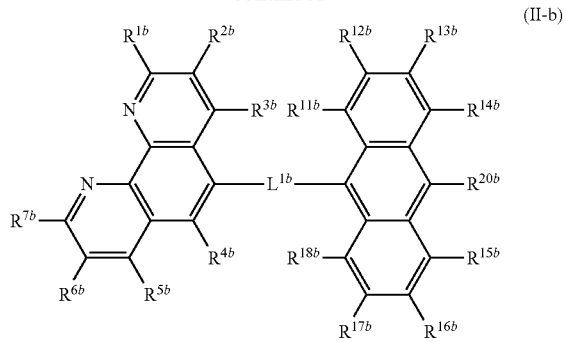

(II-b)

wherein in the formulas (I-a), (I-b), (II-a) or (II-b), $R^{1a}$ to $R^{7a}$ and $R^{1b}$ to $R^{7b}$ are the same as those in the formulas (I) and (II);

$R^{11a}$ to $R^{20a}$ and $R^{11b}$ to $R^{20b}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 ring carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 5 to 50 ring carbon atoms, a substituted or unsubstituted alkoxycarbonyl group including 2 to 50 carbon atoms, an amino group that is substituted with a substituted or unsubstituted aryl group including 6 to 50 ring carbon atoms, a halogen atom, a cyano group, a nitro group, a hydroxyl group or a carboxyl group, and adjacent groups of $R^{1a}$ to $R^{20a}$ or adjacent groups of $R^{11b}$ to $R^{20b}$ may be bonded each other to form a ring; and $L^{1a}$ and $L^{1b}$ are independently a single bond or a linkage group.

3. The organic electroluminescence device according to claim 1, wherein the donor-containing layer comprises at least one of an electron-donating metal, an electron-donating metal compound and an electron-donating metal complex.

4. The organic electroluminescence device according to claim 3, wherein the donor-containing layer comprises at least one of an alkali metal, an alkali earth metal, a simple substance of a rare earth metal, a compound of a rare earth metal and a complex of a rare earth metal.

5. The organic electroluminescence device according to claim 1, wherein the acceptor-containing layer comprises a compound represented by the following formula (III):

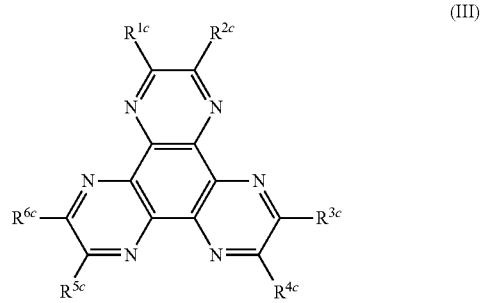

(III)

wherein in the formula (III), $R^{1c}$ to $R^{6c}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 ring carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group that is substituted with a substituted or unsubstituted aryl group including 6 to 50 ring carbon atoms, a halogen atom, a cyano group, a nitro group, a hydroxyl group or a carboxyl group.

6. The organic electroluminescence device according to claim 1, wherein the acceptor-containing layer comprises a compound represented by the following formula (IV):

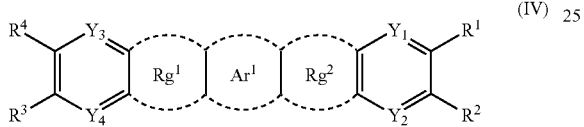
(IV)

wherein in the formula (IV), AO is an aromatic ring including 6 to 24 ring carbon atoms, or a heterocyclic ring including 5 to 24 ring atoms, and $Rg^1$ and $Rg^2$ may be the same or different from each other and are represented by the following formula (i) or (ii):

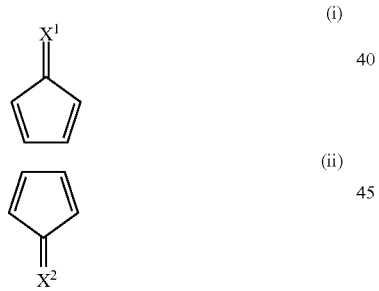

wherein $X^1$ and $X^2$ may be the same or different from each other and are represented by any of divalent groups represented by the following (a) to (g):

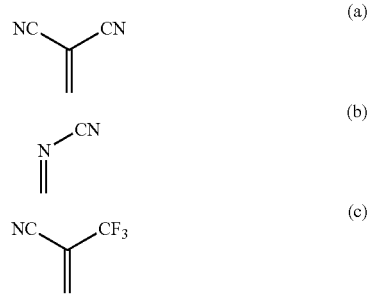
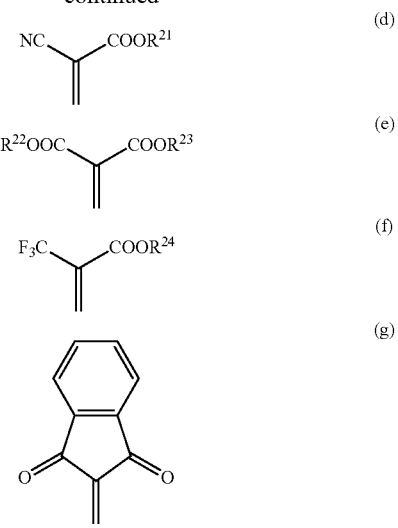

wherein $R^{21}$ to $R^{24}$ may be the same or different from each other, and are a hydrogen atom, a substituted or unsubstituted fluoroalkyl group, a substituted or unsubstituted alkyl group, a substituted or unsubstituted aryl group or a substituted or unsubstituted heterocyclic group, and $R^{22}$ and $R^{23}$ may be bonded each other to form a ring;

$R^1$ to $R^4$ may be the same or different from each other, and a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group, and $R^1$ and $R^2$ may be bonded each other to form a ring and $R^3$ and $R^4$ may be bonded each other to form a ring; and $Y^1$ to $Y^4$ may be the same or different from each other, and are independently N, CH, or $C(R^5)$, and $R^5$ is the same as $R^1$ to $R^4$.

7. The organic electroluminescence device according to claim 1, wherein the one or more organic thin film layers including the emitting layer constitute two or more emitting units that are stacked with a charge-generating layer being disposed therebetween.

8. The organic electroluminescence device according to claim 7, wherein at least one of materials constituting the emitting units is different from a material constituting the emitting layer(s) of the other emitting unit(s).

9. The organic electroluminescence device according to claim 1, wherein the organic electroluminescence device emits white light.

10. The organic electroluminescence device according to claim 1, wherein $L^{1a}$ and $L^{1b}$ each exclude an arylene group, a pyridinylene group, a quinolinylene group, and a fluorenylene group.

11. The organic electroluminescence device according to claim 1, wherein at least one of $L^{1a}$ and $L^{1b}$ is a benzene ring group.

12. The organic electroluminescence device according to claim 1, wherein at least one of $L^{1a}$ and $L^{1b}$ is a naphtalene ring group.

13. The organic electroluminescence device according to claim 1, wherein at least one of $L^{1a}$ and $L^{1b}$ is a methylene ring group.

14. The organic electroluminescence device according to claim 1, wherein at least one of $L^{1a}$ and $L^{1b}$ is a pyridine ring group.

* * * * *